US007527934B2

(12) United States Patent
Ying et al.

(10) Patent No.: US 7,527,934 B2
(45) Date of Patent: May 5, 2009

(54) LABELED SUBSTRATE CONJUGATES FOR IDENTIFYING ENZYME INHIBITORS

(75) Inventors: Laiqiang Ying, Eugene, OR (US); Jacquelyn Gervay-Hague, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 280 days.

(21) Appl. No.: 11/190,076

(22) Filed: Jul. 25, 2005

(65) Prior Publication Data
US 2006/0057658 A1 Mar. 16, 2006

Related U.S. Application Data

(60) Provisional application No. 60/591,414, filed on Jul. 26, 2004.

(51) Int. Cl.
*G01N 33/53* (2006.01)
*G01N 33/567* (2006.01)
*C12Q 1/34* (2006.01)
(52) U.S. Cl. .............................. 435/7.1; 435/7.2; 435/18
(58) Field of Classification Search .................... None
See application file for complete search history.

(56) References Cited

U.S. PATENT DOCUMENTS

| | | | | | |
|---|---|---|---|---|---|
| 4,355,102 | A | * | 10/1982 | Quash ............................ | 435/5 |
| 4,501,692 | A | * | 2/1985 | Gibbons et al. .......... | 530/391.5 |
| 5,453,533 | A | * | 9/1995 | Luo et al. .................... | 560/142 |
| 6,512,100 | B1 | * | 1/2003 | Johnson et al. ............ | 536/17.2 |

FOREIGN PATENT DOCUMENTS

WO   WO 99/31280   *   6/1999

OTHER PUBLICATIONS

Ying et al. (2005) One Bead One Inhibitor One Substrate Screening of Neuraminidase Activity. ChemBioChem 6: 1857-1865.*
Amann, F. et al. "New Potent Sialyltransferase Inhibitors—Synthesis of Donor and of Transition-State Analogues of Sialyl CMP-Neu5Ac," *Chem. Eur. J.*, 1998, vol. 4, No. 6, pp. 1106-1115.
Andrews, D.M. et al. "Synthesis and Influenza Virus Sialidase Inhibitory Activity of Analogues of 4-Guanidino-Neu5Ac2en (Zanamivir) Modified in the Glycerol Side-Chain," *Eur. J. Med. Chem.*, 1999, vol. 34, pp. 563-574.
Armstrong, J.I. et al. "Discovery of Carbohydrate Sulfotransferase Inhibitors from a Kinase-Directed Library," *Agnew. Chem. Int. Ed.*, 2000, vol. 39, No. 7, pp. 1303-1306.
Babu, Y.S. et al. "BCX-1812 (RWJ-270201): Discovery of a Novel, Highly Potent, Orally Active, and Selective Influenza Neuraminidase Inhibitor Through Structure-Based Drug Design," *J. Med. Chem.*, 2000, vol. 43, No. 19, pp. 3482-3486.
Bernatowicz, M.S. et al. "Urethane Protected Derivatives of 1-Guanylpyrazole for the Mild and Efficient Preparation of Guanidines," *Tetrahedron Letters*, 1993, vol. 34, No. 21, pp. 3389-3392.

Blixt, O. et al. "Efficient Preparation of Natural and Synthetic Galactosides with a Recombinant β-1,4-Galactosyltransferase-/UDP-4'-Gal Epimerase Fusion Protein," *J. Org. Chem.*, 2001, vol. 66, No. 7, pp. 2442-2448.
Brossmer, R. et al., "Fluorescent and Photoactivatable Sialic Acids," *Methods in Enzymology*, 1994, vol. 247, pp. 177-193.
Burmeister, W.P. et al. "The 2.2 Å Resolution Crystal Structure of Influenza B Neuraminidase and Its Complex with Sialic Acid," *The EMBO Journal*, 1992, vol. 11, No. 1, pp. 49-56.
Cambron, L.D. et al. "Inhibition of CMP-N-Acetylneuraminic Acid: Lactosylceramide Sialyltransferase by Nucleotides, Nucleotide Sugars and Nucleotide Dialdehydes," *Biochemical and Biophysical Research Communications*, Jun. 15, 1993, vol. 193, No. 2, pp. 585-590.
Chagas, J.R. et al. "Intramolecularly Quenched Fluorogenic Tetrapeptide Substrates for Tissue and Plasma Kallikreins," *Analytical Biochemistry*, 1991, vol. 192, pp. 419-425.
Chand, P. et al. "Systematic Structure-Based Design and Steroselective Synthesis of Novel Multisubstituted Cyclopentane Derivatives with Potent Antiinfluenza Activity," *J. Med. Chem.*, 2001, vol. 44, No. 25, pp. 4379-4392.
Chernyak, A. Y. et al. "2-Azidoethyl Glycosides: Glycosides Potentially Useful for the Preparation of Neoglycoconjugates," *Carbohydrate Research*, 1992, vol. 223, pp. 303-309.
Chong, A.K.J. et al. "Characterisation of an Ionisable Group Involved in Binding and Catalysis by Sialidase from Influenza Virus," *Biochemistry International*, May 1991, vol. 24, No. 1, pp. 165-171.
Clarke, D.J. et al. "Synthesis of Thio- and Oxo-Analogues of Isopsoralen," *Tetrahedron*, 2002, vol. 58, pp. 2831-2837.
Cohen, S.B. et al. "Synthesis and Characterization of an Anomeric Sulfur Analogue of CMP-Sialic Acid," *J. Org. Chem.*, 2000, vol. 65, No. 19, pp. 6145-6152.
Colman, P.M. "Neuraminidase: Enzyme and Antigen," Chapter 4 In *The Influenza Viruses*, Klug, R.M., ed., Plenum Press: NY, 1989, pp. 175-218.
Compain, P. et al. "Carbohydrate Mimetics-Based Glycosyltransferase Inhibitors," *Bioorganic Medicinal Chemistry*, 2001, vol. 9, pp. 3077-3092.
Copeland, G.T. et al. "Selection of Enantioselective Acyl Transfer Catalysts from a Pooled Peptide Library Through a Fluorescence-Based Activity Assay: An Approach to Kinetic Resolution of Secondary Alcohols of Broad Structural Scope," *J. Am. Chem. Soc.*, 2001, vol. 123, pp. 6496-6502.

(Continued)

*Primary Examiner*—Lisa J Hobbs
(74) *Attorney, Agent, or Firm*—Townsend and Townsend and Crew LLP

(57) ABSTRACT

This invention provides labeled-substrate conjugates for assaying enzymes, particularly neuraminidases. Also provided are assays that are useful for identifying compounds that inhibit sialyltransferases or neuraminidases and may be useful in treating subjects with influenza. In particular, the present invention relates to methods of using such labeled substrate conjugates to screen for enzyme inhibitors, particularly in a high-throughput format.

25 Claims, 20 Drawing Sheets

OTHER PUBLICATIONS

Corfield, A.P. et al. "Role of Sialic Acids and Sialidases in Molecular Recognition Phenomena," *In Conference Philippe Laudat* Institute National de la Sante et de la Racherche Medicale (INSERM), 1992, pp. 113-134, pp. 135-159 French version, pp. 159-166 references, pp. 167-175, conference program in both English and French.

Corfield, T. "Bacterial Sialidases—Roles in Pathogenicity and Nutrition," *Glycobiology*, 1992, vol. 2, No. 6, pp. 509-521.

Crennell, S. et al. "Crystal Structure of *Vibrio cholerae* Neuraminidase Reveals Dual Lectin-Like Domains in Addition to the Catalytic Domain," *Structure*, Jun. 15, 1994, vol. 2, No. 6, pp. 535-544.

Crennell, S.J. et al. "The Structures of *Salmonella typhimurium* :LT2 Neuraminidase and Its Complexes with Three Inhibitors at High Resolution," *J. Mol. Biol.*, 1996, vol. 259, p. 264-280.

Demant, E.J.F. "Covalent Complexes Between Serum Albumin and 7-hydroxycoumarin-4-Acetic Acid: Synthesis and Applications in the Spectrophotometric Detection of Long-Chain Fatty Acids," *Biochimica et Biophysica Acta*, 1996, vol. 1304, pp. 43-55.

Dufner, G. et al. "Base- and Sugar-Modified Cytidine Monophosphate N-Acetylneuraminic Acid (CMP-Neu5Ac) Analogues—Synthesis and Studies with α(2-6)- Sialytransferase from Rat Liver," *Eur. J. Org. Chem.*, 2000, pp. 1467-1482.

Feizi, T., "Carbohydrate-Mediated Recognition Systems in Innate Immunity," *Immunological Reviews*, 2000, vol. 173, pp. 79-88.

Fukuda, M. et al., eds. "Roles of Cell Surface Carbohydrates" Chapter 5 *In Molecular and Cellular Glycobiology*, Oxford University Press: NY, 2000, pp. 33-44.

Gerber, S.A. et al. "Design and Synthesis of Substrate and Internal Standard Conjugates for Profiling Enzyme Activity in the Sanfilippo Syndrome by Affinity Chromatography/Electrospray Ionization Mass Spectrometry," *Bioconjugate Chem.*, 2001, vol. 12, No. 4, pp. 603-615.

Grieco, P. et al. "Preparation of 'side-chain-to-side-chain' cyclic peptides by Allyl and Alloc Strategy: Potential for Library Synthesis," *J. Peptide Research*, 2001, vol. 57, pp. 250-256.

Gross, H.J. et al. "Transfer of Synthetic Sialic Acids Analogues to N- and O-Linked Glycoprotein Glycans Using Four Different Mammalian Sialytransferases," *Biochemistry*, 1989, vol. 28, No. 18, pp. 7386-7392.

Gross, H.J. et al. "A Highly Sensitive Fluorometric Assay for Sialytransferase Activity Using CMP-9-Fluoresceinyl-NeuAc as Donor," *Analytical Biochemistry*, 1990, vol. 186, pp. 127-134.

Gubareva, L.V. et al. "Influenza Virus Neuraminidase Inhibitors," *The Lancet*, Mar. 4, 2000, vol. 355, pp. 827-835.

Gubareva, L.V. et al. "Comparison of the Activities of Zanamivir, Oseltamivir, and RWJ-270201 Against Clinical Isolates of Influenza Virus and Neuraminidase Inhibitor-Resistant Variants," *Antimicrobial Agents and Chemotherapy*, Dec. 2001, vol. 45, No. 12, pp. 3403-3408.

Harduin-Lepers, A. et al., "The Human Sialytransferase Family," *Biochimie*, 2001, vol. 83, pp. 727-737.

Harris, R.F. et al. "A Polymeric and Fluorescent Gel for Combinatorial Screening of Catalysts," *J. Am. Chem. Soc.*, 2000, vol. 122, No. 45, pp. 11270-11271.

Hatanaka, Y. et al. "A Carbene-Generating Biotinylated Lactosylceramide Analog as Novel Photoreactive Substrate for $GM_3$ Synthase," *Bioorganic & Medicinal Chemistry Letters*, 1995, vol. 5, No. 23, pp. 2859-2862.

Hochgürtel, M. et al., "Target-Induced Formation of Neuraminidase Inhibitors from in vivo Virtual Combinatorial Libraries," *Proc. Natl. Acad. Sci. USA*, Mar. 19, 2002, vol. 99, No. 6, pp. 3382-3387.

Holzer, C.T. et al. "Inhibition of Sialidases from Viral, Bacterial and Mammalian Sources by Analogues of 2-deoxy-2,3-didehydro-N-acetylneuraminic Acid Modified at the C-4 Position," *Glycoconjugate Journal*, 1993, vol. 10, pp. 40-44.

Honda, T. et al. "Synthesis and Anti-Influenza Virus Activity of 4-Guanidino-7-Substituted Neu5Ac2en Derivatives," *Bioorganic & Medicinal Chemistry Letters*, 2002, vol. 12, pp. 1921-1924.

Horita, K. et al. "On the Selectivity of Deprotection of Benzyl, MPM (4-Methoxybenzyl) and DMPM (3,4-Dimethoxybenzyl) Protecting Groups for Hydroxy Functions", *Tetrahedron*, 1986, vol. 42, No. 11, pp. 3021-3028.

Hughes, R.C. "Galectins as Modulators of Cell Adhesion," *Biochimie*, 2001, vol. 83, pp. 667-676.

Ikeda, K. et al. "Lipid A and Related Compounds. XXVI. [1)] Synthesis of Biologically Active Penta-O-acetyl-N-gly-coloylneuraminyl- and Penta-O-acetyl-3-deoxy-D-glycero-D-galacto-2-nonulopyransonic Acid-(α 2 →6)-D-glucosamine-4-phosphate Analogs of Lipid A," *Chem. Pharm. Bull.*, May 1991, vol. 39, No. 5, pp. 1305-1309.

Ikeda, K. et al. "Use of Phenyl 2-α-Selenoglycosides of N-Acetylneuraminic Acid as a Glycosyl Donor for the Glycosylation Reactions," *Bioorganic & Medicinal Chemistry Letters*, 2002, vol. 12, pp. 2309-2311.

Imamura, M. et al. "Synthesis of Novel CMP-NeuNAc Analogues Having a Glycosyl Phosphonate Structure," *Tethrahedron Letters*, 1996, vol. 37, No. 9, pp. 1451-1454.

Jarvo, E.R. et al. "Fluorescence-Based Screening of Asymmetric Acylation Catalysts Through Parallel Enantiomer Analysis. Identification of a Catalyst for Tertiary Alcohol Resoulution," *J. Org. Chem.*, 2001, vol. 66, pp. 5522-5527.

Jeanloz, R.W. et al. "Synthesis of Various Glycosides of 2-Amino-3-O-($_D$-1-Carboxyethyl)-2-Deoxy-D-Glucopyranose (Muramic Acid)," *Carbohydrate Research*, 1968, vol. 6, pp. 184-196.

Juliano, L. et al. "A Selective Assay for Endooligopeptidase a Based on the Cleavage of Fluorogenic Substrate Structurally Related to Enkephalin," *Biochemical and Biophysical Research Communications*, Dec. 14, 1990, vol. 173, No. 2, pp. 647-652.

Kaifu, R. et al. "Synthesis of O-β-D-Galactopyranosyl-(1→4)-O-(2-Acetamido-2-Deoxy-β-D-Glucopyranosyl)-(1→2)-D-Mannose and Its Interaction with Various Lectines," *Carbohydrate Research*, 1976, vol. 52, pp. 179-185.

Kajihara, Y. et al. "Characterization of Inhibitory Activities and Binding Mode of Synthetic 6'-Modified Methyl N-Acetyl-β-Lactosaminide Toward Rat Liver CMP-D-Neu5Ac: D-Galactoside-(2→6)-α-D-Sialytransferase," *Carbohydrate Research*, 1993, vol. 247, pp. 179-193.

Kajihara, Y. et al. "Synthesis of Methyl 6'-Deoxy- and 6'-Thio-Lactosaminides and Their Inhibitory Activity Toward AMP-NeuNAc:D-Galactoside-(2→6)-α-D- Sialytransferase," *J. Carbohydrate Chemistry*, 1993, vol. 12, No. 7, pp. 991-995.

Kiefel, M.J. et al. "Recent Advances in the Synthesis of Sialic Acid Derivatives and Sialymimetics as Biological Probes," *Chem. Rev.*, 2002, vol. 102, No. 2, pp. 471-490.

Kijima-Suda, I. et al. "Inhibition of Experimental Pulmonary Metastasis of Mouse Colon Adenocarcinoma 26 Sublines by a Sialic Acid:Nucleoside Conjugate Having Sialytransferase Inhibiting Activity," *Cancer Research*, Feb. 1986, vol. 46, pp. 858-862.

Kim, C.U. et al. "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," *J. Am. Chem. Soc.*, 1997, vol. 119, No. 4, pp. 681-690.

Kirchner, E. et al. "Studies on the Glycosylation of N-Acetylneuraminic Acid," *J. Carbohydrate Chemistry*, 1988, vol. 7, No. 2, pp. 453-486.

Klohs. W.D. et al. "Effects of Nucleotides and Nucleotide:Analogs on Human Serum Sialytransferase," *Cancer Research*, Apr. 1979, vol. 39, pp. 1231-1238.

Lam, K.S. et al. "A New Type of Synthetic Peptide Library for Identifying Ligand-Binding Activity," *Nature*, Nov. 7, 1991, vol. 354, pp. 82-84.

Lam, K.S. et al. "The 'One-Bead-One-Compound' Combinatorial Library Method," *Chem. Rev.*, 1997, vol. 97, No. 2, pp. 411-448.

Lee, K-Y. et al. "The Hexapeptide Inhibitor of Galβ1,3GalNAc-specific α2,3-Sialytransferase as a Generic Inhibitor of Sialytransferases," *The Journal of Biological Chemistry*, Dec. 20, 2002, vol. 277, No. 51, pp. 49341-49351.

Limberg, G. et al. "A New Assay for Sialytransferases Using Fluorescein-Labelled Acceptors," *Liebigs Ann.*, 1996, pp. 1773-1784.

Liu, C. et al. "Influenza Type A Virus Neuraminidase Does Not Play a Role in Viral Entry, Replication, Assembly, or Budding," *Journal of Virology*, Feb. 1995, vol. 69, No. 2, pp. 1099-1106.

Liu, R. et al. "A Novel Peptide-Based Encoding System for 'One-Bead One-Compound' Peptidomimetic and Small Molecule Combinatorial Libraries," *J. Am. Chem. Soc.*, 2002, vol. 124, No. 26, pp. 7678-7680.

Marra, A. et al. "Acetylation of N-Acetylneuraminic Acid and Its Methyl Ester," *Carbohydrate Research*, 1989, vol. 190, pp. 317-322.

Martin T.J. et al. "A Convenient Synthesis of Nucleoside Monophosphate-N-Acetylneuraminic Acids (NMP-Neu5Ac)[1]," *Bioorganic & Medicinal Chemistry*, 1994, vol. 2, No. 11, pp. 1203-1208.

Masuda, T. et al. "Synthesis and Anti-Influenza Evaluation of Orally Active Bicyclic Ether Derivatives Related to Zanamivir," *Bioorganic & Medicinal Chemistry Letters*, 2003, vol. 13, pp. 669-673.

Matta, K.L. et al. "Synthesis of p-Nitrophenyl 2-Acetamido-2-Deoxy-O-β-D-Galactopyranosyl-β-D-Glucopyranosides," *Carbohydrate Research*, 1975, vol. 43, pp. 299-304.

McKimm-Breschkin, J.L. "Resistance of Influenza Viruses to Neuraminidase Inhibitors—a Review," *Antiviral Research*, 2000, vol. 47, pp. 1-17.

Meldal, M. et al. "Pega: A Flow Stable Polyethylene Glycol Dimethyl Acrylamide Copolymer for Solid Phase Synthesis," *Tetrahedron Letters*, 1992, vol. 33, No. 21, pp. 3077-3080.

Meldal, M et al. "Portion-Mixing Peptide Libraries of Quenched Fluorogenic Substrates for Complete Subsite Mapping of Endoprotease Specificity," *Proc. Natl. Acad. Sci. USA*, Apr. 1994, vol. 91, pp. 3314-3318.

Meldal, M. "The One-Bead Two-Compound Assay for Solid Phase Screening of Combinatorial Libraries," *Biopolymers*, 2002, vol. 66, pp. 93-100.

Mohan, H. et al. "Efficient Synthesis of Spacer-Linked Dimers of N-Acetyllactosamine Using Microwave-Assisted Pyridinium Triflate-promoted Glycosylations with Oxazoline Donors," *Synlett*, 2003, vol. 9, pp. 1255-1256.

Müller, B. et al. "Efficient Sialyltransferase Inhibitors Based on Transition-State Analogues of the Sialyl Donor," *Agnew. Chem. Int. Ed.*, 1998, vol. 37, No. 20, pp. 2893-2897.

Müller, B. et al. "Synthesis of Phosphonate Analogues of CMP-Neu5Ac Determination of $\alpha(2\text{-}6)$-Sialyltransferase Inhibition," *Tetrahedron Letters*, 1998, vol. 39, pp. 509-512.

Nefzi, A. et al. "The Current Status of Heterocyclic Combinatorial Libraries," *Chem. Rev.*, 1997, vol. 97, No. 2, pp. 449-472.

Nordlander, J.E. et al. "Friedel-Crafts Acylation with N-(Trifluroacetyl)-α-amino Acid Chlorides. Application to the Preparation of β-Arylalkylamines and 3-Substituted 1,2,3,4-Tetrahydroisoquinolines," *The Journal of Organic Chemistry*, Nov. 2, 1984, vol. 49, No. 22, pp. 4107-4111.

Palese, P. et al. "Inhibitors of Viral Neuraminidase as Potential Antiviral Drugs" Chapter 6 *In Chemoprophylaxis and Virus Infections of the Respiratory Tract vol. 1*, Oxford, J.S. ed., 1977, CRC Press, Inc.: Cleveland, OH, pp. 189-205.

Paul, P. et al. "Synthesis and Characterization of a New Class of Inhibitors of Membrane-associated UDP-Glycosyltransferases," *The Journal of Biological Chemistry*, Jun. 15, 1993, vol. 268, No. 17, pp. 12933-12938.

Paulson, J.C. et al. "Enzymatic Properties of β-D-Galactoside $\alpha 2 \rightarrow 6$ Sialyltransferase from Bovine Colostrum," *The Journal of Biological Chemistry*, Apr. 10, 1977, vol. 252, No. 7, pp. 2363-2371.

Pirrung, M.C. et al. "Spatially Addressable Combinatorial Libraries," *Chem. Rev.*, 1997, vol. 97, No. 2, pp. 473-488.

Platt, F.M. et al. "Prevention of Lysosomal Storage in Tay-Sachs Mice Treated with N-Butyldeoxynojirimycin," *Science*, Apr. 18, 1997, vol. 276, pp. 428-431.

Potier, M. et al. "Fluorometric Assay of Neuraminidase with a Sodium (4-Methylumbelliferyl-α-D-N-Acetylneuraminate) Susbstrate," *Analytical Biochemistry*, 1979, vol. 94, pp. 287-296.

Rana, S.S. et al. "A Facile Synthesis of Benzyl 2-Acetamido-6-O-Acetyl-4-O-(6-O-Acetyl-3,4-O-Isopropylidene-β-D-Galactopyranosyl)-2-Deoxy-β-D-Glucopyranoside, a Key Intermediate for the Synthesis of O-α-L-Fucopyranosyl-1-(1→2)-O-β-D-Galactopyranosyl-(1→4)-O-[α-L-Funcopyranosyl-(1→3)]-2-Acetamido-2-Deoxy-D-Glucopyranose," *Carbohydrate Research*, 1983, vol. 113, pp. C18-C21.

Rosenberg, A. et al. "Sialidases," Chapter 10 *In Biological Roles of Sialic Acids*, Plennum Press: N.Y., 1976, pp. 295-359.

Rostovtsev, V.V. et al. "A Stepwise Huisgen Cycloaddition Process: Copper (I)-Catalyzed Regioselective 'Ligation' of Azides and Terminal Alkynes," *Agnew Chem. Int. Ed.*, 2002, vol. 41, No. 14, pp. 2596-2599.

Saidi, M.R. et al. "Microwave and $BF_3$ Promoted Rearrangement of Allyloxycoumarins to Allylcoumarins and Dihydrofurocoumarins," *Heterocycles*, 2001, vol. 55, No. 9, pp. 1805-1812.

Schaub, C. et al. "New Sialyltransferase Inhibitors Based on CMP-Quinic Acid: Development of a New Sialyltransferase Assay," *Glycoconjugate Journal*, 1998, vol. 15, pp. 345-354.

Schauer, R. "Chemistry, Metabolism, and Biological Functions of Sialic Acids," *Advances in Carbohydrate Chemistry Biochemistry*, 1982, vol. 40, pp. 131-234.

Schmidt, A.C. "Antiviral Therapy for Influenza: A Clinical and Economic Comparative Review," *Drugs*, 2004, vol. 62, No. 18, pp. 2031-2046.

Schröder, P.N. et al. "From Substrate to Transition State Analogues: The First Potent Inhibitor of Sialyltransferases," *Agnew. Chem. Int. Ed.*, 1999, vol. 38, No. 10, pp. 1379-1380.

Schwörer, R. et al. "Efficient Sialyltransferase Inhibitors Based on Glycosides of N-Acetylglucosamine," *J. Am. Chem. Soc.*, 2002, vol. 124, No. 8, pp. 1632-1637.

Stefanova, H.I. et al. "Reactivity of Lysyl Residues on the ($Ca^{2+}$-$Mg^{2+}$)-ATPase to 7-Amino-4-methylcoumarin-3-acetic Acid Succinimidyl Ester," *Biochemistry*, 1993, vol. 32, No. 1, pp. 356-362.

Sun, H. et al. "Synthesis of a New Transition-State Analog of the Sialyl Donor. Inhibition of Sialyltransferases," *Tetrahedron Letters*, 2001, vol. 42, pp. 2451-2453.

Sun, X-L. et al. "Glycosaminoglycan Mimetic Biomaterials. 4. Synthesis of Sulfated Lacotse-Based Glycopolymers That Exhibit Anticoagulant Activity," *Biomacromolecules*, 2002, vol. 3, pp. 1065-1070.

Taliani, M. et al. "An Improved Solid-Phase Synthesis of Resonance Energy Transfer Fluorescent Peptides and Depsipeptides Employing the EDANS/DABCYL Donor-Acceptor Pair," *Letters in Peptide Science*, 1997, vol. 4, pp. 101-106.

Taylor, N.R. et al. "Dihydropyrancarboxamides Related to Zanamivir: A New Series of Inhibitors of Influenza Virus Sialidases. 2. Crystallographic and Molecular Modeling Study of Complexes of 4-Amino-4H-pyran-6-carboxamides and Sialidase from Influenza Virus Types A and B," *J. Med. Chem.*, 1998, vol. 41, No. 6, pp. 798-807.

Varghese, J.N. et al. "Structure of the Influenza Virus Glycoprotein Antigen Neuraminidase at 2.9 Å Resolution," *Nature*, May 5, 1983, vol. 303, pp. 35-40.

Varghese, J.N. et al. "Three-Dimensional Structure of the Neuraminadase of Influenza Virus A/Tokyo/3/67 at 2-2 Å Resolution," *J. Mol. Biol.*, 1991, vol. 221, pp. 473-486.

Varghese, J.N. et al. "Three-Dimensional Structure of the Complex of 4-Guanidino-Neu5Ac2en and Influenza Virus Neuraminidase," *Protein Science*, 1995, vol. 4, pp. 1081-1087.

Varghese, J.N. "Development of Neuraminidase Inhibitors as Anti-Influenza Virus Drugs," *Drug Development Research*, 1999, vol. 46, pp. 176-196.

von Itzstein, M. et al. "Rational Design of Potent Sialidase-Based Inhibitors of Influenza Virus Replication," *Nature*, Jun. 3, 1993, vol. 363, pp. 418-423.

Vyas, A.A. et al. "Brain Gangliosides: Functional Ligands for Myelin Stability and the Control of Nerve Regeneration," *Biochimie*, 2001, vol. 83, pp. 677-682.

Wang, X. et al. "Recent Development in the Design of Sialyltransferase Inhibitors," *Medicinal Research Reviews*, 2003, vol. 23, No. 1, pp. 32-47.

Wu, C-Y. et al. "Soyasaponin I, a Potent and Specific Sialyltransferase Inhibitor," *Biochemical and Biophysical Research Communications*, 2001, vol. 284, No. 2, pp. 466-469.

Wyatt, P.G. et al. "Sialidase Inhibitors Related to Zanamivir. Further SAR Studies of 4-Amino-4H-pyran-2-carboxylic Acid-6-propylamides," *Bioorganic & Medicinal Chemistry Letters*, 2001, vol. 11, pp. 669-673.

Zaikova, T.O. et al. "Synthesis of Fluorogenic Substrates for Continuous Assay of Phosphatidylinositol-Specific Phospholipase C," *Bioconjugate Chemistry*, 2001, vol. 12, No. 2, pp. 307-313.

Zhu, Q. et al. "Enzymatic Profiling System in a Small-Molecule Microarray," *Organic Letters*, 2003, vol. 5, No. 8, pp. 1257-1260.

* cited by examiner

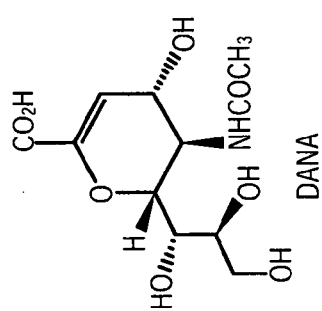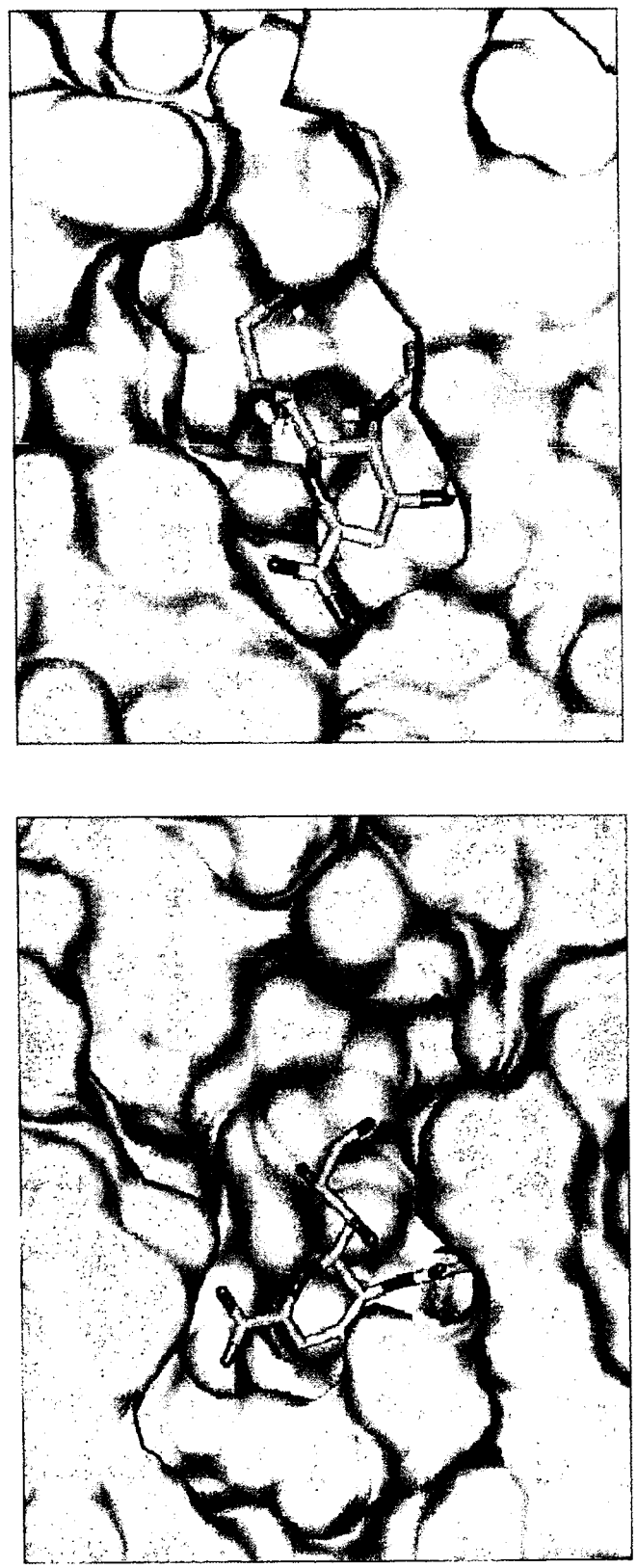
FIG. 2

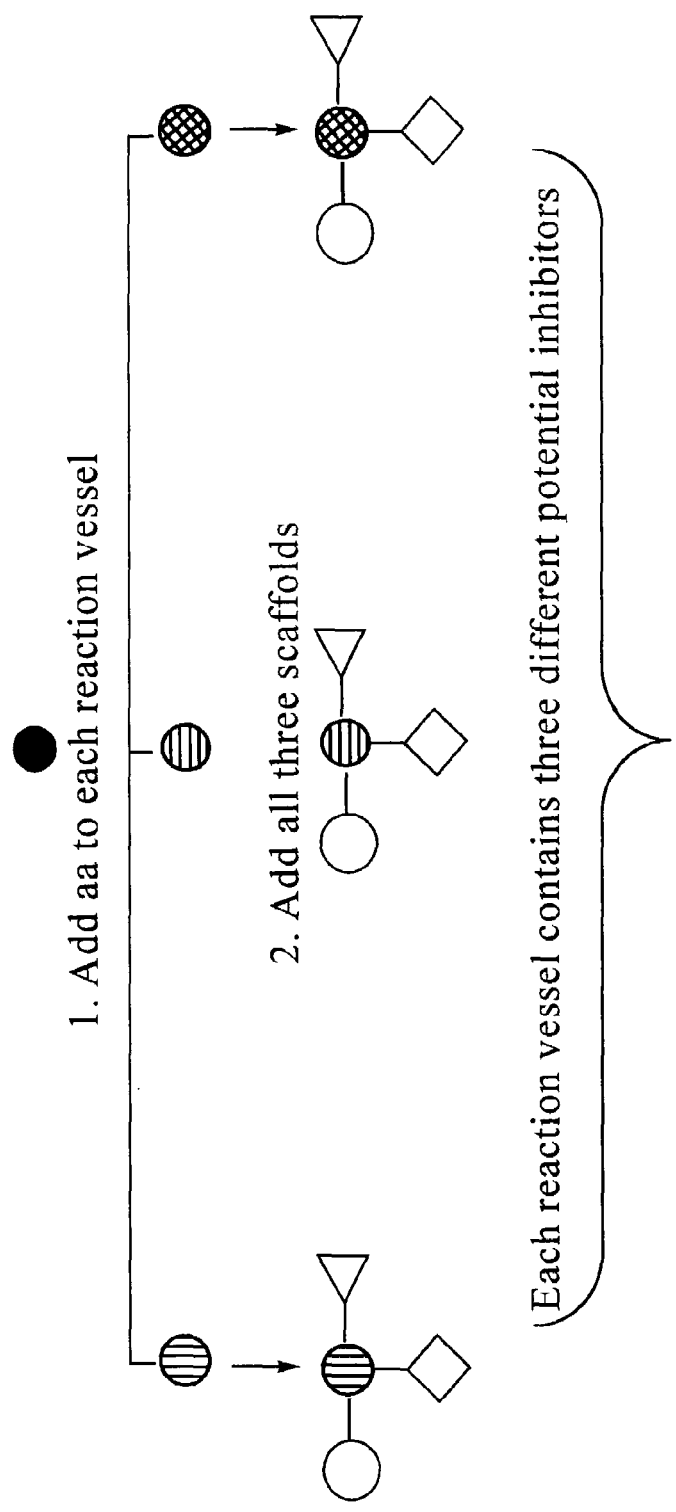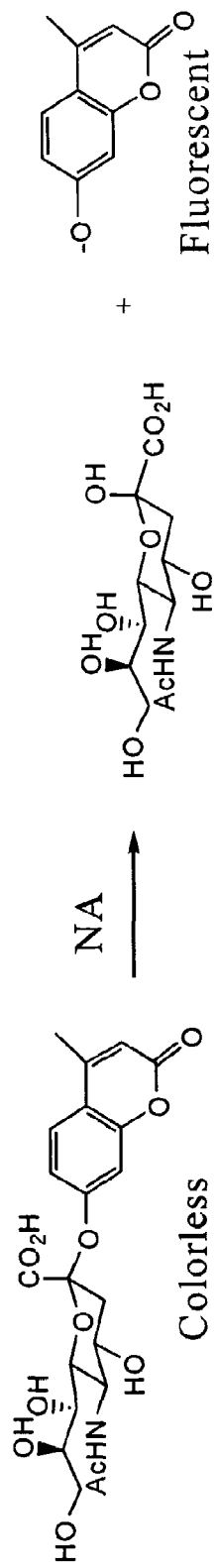
FIG. 3

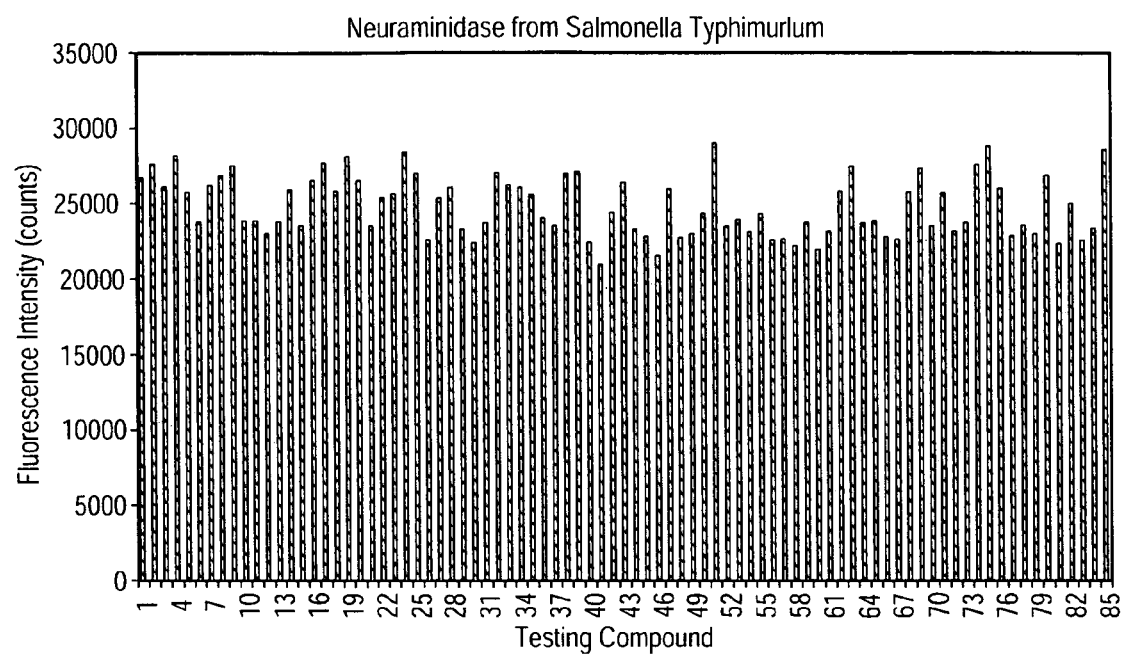
b
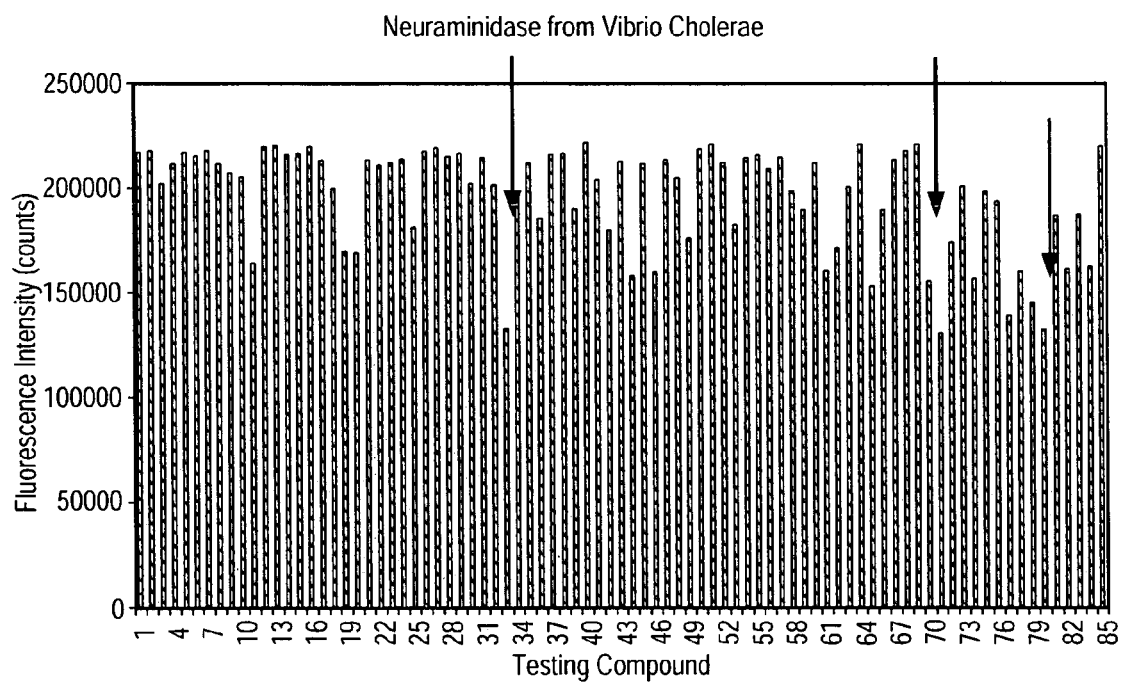
c
FIG. 8 *(Continued)*

FIG. 14  Quenching Efficiency of Compound 41 and 42

FIG. 15 Activity of Acceptors 64 and 69 for Substrate Recognition by Sialyltransferase FIG. 16 Sialyltransferase Competitive Assay Uisng Donor 55 and CMP-Neu5Ac FIG. 17 Recognition of On-bead Acceptors by Sialyltransferases FIG. 18 Inhibitory Activity of 75, 77, and 78 Against Sialyltransferases

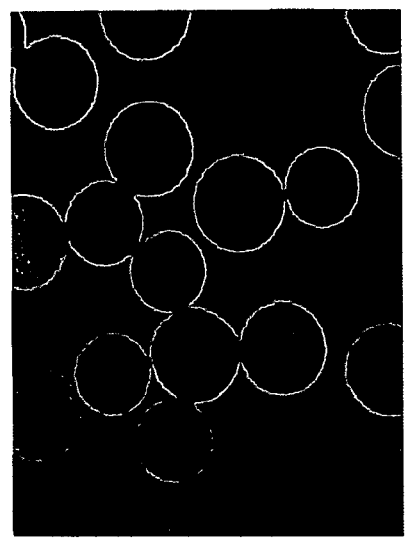
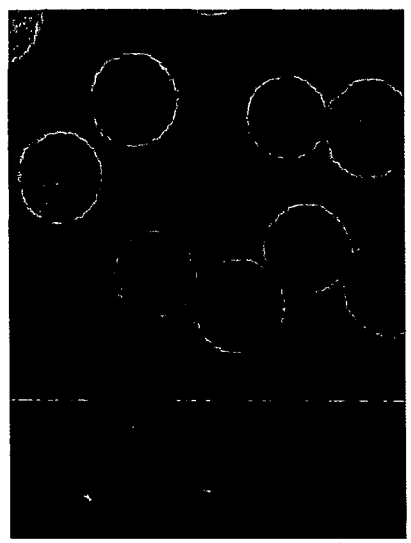
FIG. 19

LABELED SUBSTRATE CONJUGATES FOR IDENTIFYING ENZYME INHIBITORS

CROSS-REFERENCES TO RELATED APPLICATIONS

This application claims benefit of priority under 35 U.S.C. §119(e) to U.S. Provisional application No. 60/591,414 filed Jul. 26, 2004, which is herein incorporated by reference in its entirety.

STATEMENT AS TO RIGHTS TO INVENTIONS MADE UNDER FEDERALLY SPONSORED RESEARCH OR DEVELOPMENT

This invention was made with Government support under Grant (or Contract) No. CHE-0196482, awarded by the National Science Foundation. The Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Combinatorial chemistry has developed into a useful method for the rapid synthesis of new compounds for drug discovery (see Lam, K. S. et al. *Nature* 1991, 354, 82-84). However, a crucial step in this drug discovery process is the development of high-throughput in vitro enzyme assays to identify positive hits from such combinatorial libraries.

For example, library screening has identified small molecule sulfotransferase inhibitors (see Armstrong, J. I. et al. *Angew. Chem. Int. Ed.* 2000, 39, 1303-1306). Meldal has reported using fluorescent resonance energy transfer (FRET) substrates and one-bead-two-compounds library approaches to screen protease inhibitors (see Meldal, M. *Biopolymers* 2002, 66, 93-100). A potent and specific sialyltransferase inhibitor, Soyasaponin I, has been discovered by screening over 7500 microbial extracts and natural products (see Wu, C. Y. et al. *Biochem. Biophys. Res. Commun.* 2001, 284(2), 466-469). More recently, a peptide WWWWNG-NH$_2$ was identified as a potent inhibitor for α2,3-sialyltransferase (ST3Gal I) from the screening of a combinatorial peptide library (see Lee, K. Y. et al. *J. Biol. Chem.* 2002, 277, 49341-49351).

Another pharmaceutically important enzyme is neuraminidase (NA). Neuraminidase is an enzyme that cleaves the α-ketosidic linkage of the terminal sialic acids and has been found in viruses, bacteria, parasites, and mammalian cells (see Corfield, T. *Glycobiology* 1992, 2, 509-521; and Corfield, A. P. et al. "Role of sialidases and sialic acids in molecular recognition phenomena" in *conferences Philippe Laudat* 1991 pp. 113-134, Institute National de la Sante et de la Racherche Medicale, (INSERM), Paris; Rosenberg and Schengrund *Biological roles of sialic acids* Plennum Press, N.Y, 1976, pp. 295-360). It plays an important biological role in the regulation of glycoconjugates involved in cell-to-cell interactions (see Schauer, R. *Adv. Carbohydr. Chem. Biochem.* 1982, 40, 131-134). For example, influenza viruses have two surface glycoproteins, hemaggutinin and neuraminidase. Hemagglutinin binds to receptors containing neuraminic acid, which allows the virus to penetrate through the cell membrane. Neuraminidase destroys receptors recognized by hemaggutinin by cleaving the α-ketosidic linkage of sialic acids. This cleavage facilitates passage of the virus to and from sites in the respiratory tract (see Colman, P. M. "Neuraminidase: enzyme and antigen" in *The Influenza Viruses* (Klug, R. M., ed.), 1989, pp. 175-218. Plenum Publishing Corporation, New York). Studies with a neuraminidase-deficient influenza virus have shown that the mutant virus is still infective but the budding virus particles form aggregates or remain bound to the infected cell surface (see Liu, C. et al. *J. Virol.* 1995, 69, 1099-1106). Influenza causes considerable disease burden each year and while vaccination is the first line of defense against influenza A and B viruses, antiviral therapy can aid in controlling the impact of the disease (see Schmidt *Drugs* 62: 2031 (2004)).

This important biological activity has prompted chemists to use the crystal structure of neuraminidase to design specific inhibitors as anti-influenza virus agents (see FIG. 1 from von Itzstein, M.; et al. *Nature,* 1993, 363, 418-423; and Taylhell, N. R. et al. *J. Med. Chem.* 1998, 41, 798-807; and FIG. 2. from Crennell, S. J. et al. *J. Mol. Biol.* 1996, 259, 264; and *Structure* 1994, 2, 535-544 (see also Kim, C. U. et al. *J. Am. Chem. Soc.* 1997, 119, 681-690; Babu, Y. S. et al. *J. Med. Chem.* 2000, 43, 3482-3486; Chand, P.; et al. *J. Med. Chem.* 2001, 44, 4379-4392; Andrews, D. M. et al. *Eur. J. Med. Chem.* 1999, 34, 563-574; and Kiefel, M. J. and von Itzstein, M. *Chem. Rev.* 2002, 102, 471-490). Since the determination of the crystal structure of the influenza neuraminidase, (see Varghese, J. N. et al. *Nature* 1983, 303, 35-40; Varghese, J. N. and Colman, P. M. *J. Molec. Biol.* 1991, 221, 473-486; Burmeister, W. P. et al. *EMBO J.* 1992, 11, 49-56; and Varghese, J. N. et al. *Protein Science* 1995, 4, 1081-1087) many derivatives of 2-deoxy-2,3-dehydro-N-acetylneuraminic acid (DANA) have been designed as transition state analogues to block the catalytic sites of influenza neuraminidase (see Varghese, J. N. *Drug Development Res.* 1999, 46, 179-196, Palese and Schulman in *Chemoprophylaxis and Virus Infections of the Upper Respiratory Tract* vol. 1 CRC Press Cleveland (Oxfod, J. S. ed.) 1977 pp. 189-205; and references cited therein). This has lead to the development of highly potent influenza neuraminidase inhibitors ZANAMIVIR™ and OSELTAMIVIR™, which are currently in use for treatment of influenza virus infection (see Gubareva, L. V. et al. *Lancet* 2000, 355, 827-835; Holzer et al. *Glycoconj. J.* 10: 40-44 (1993); Chong et al. *Biochem. Int.* 24: 165-171 (1991); and references cited therein). More recently, the synthesis and biological evaluation of a functionalized cyclopentane analog, RWJ-270201, has been reported (Chand et al. *J. Med. Chem.* 44: 4379 (2001). This compound is a potent inhibitor of wild-type NA and some ZANAMIVIR™- and OSELTAMIVIR™-resistant influenza A and B virus variants (Gubareva, L. V. et al. *Antimic. Agent and Chemother.* 2001, 45, 3403-3408).

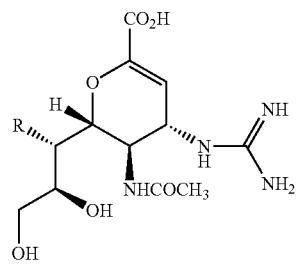

R = OH, Zanamivir
R = OCH$_3$
ROCH$_2$CH$_3$
R = O(CH$_2$)$_{11}$CH$_3$

-continued

Oseltamivir

DANA

RWJ-270201

Success in achieving selective NA inhibition by modifying the glycerol side chain to increase hydrophobic interactions led to several other studies of ZANAMIVIR™ analogs. Honda et al. published a series of papers describing the synthesis and biological evaluation of 7-O alkylated ZANAMIVIR™ analogs. Their first studies showed that the 7-hydroxyl could be replaced with fluorine to give an improved activity profile (see above). Methylation of the 7-hydroxyl led to slightly diminished anti-NA activity but the ethyl ether was actually more active than ZANAMIVIR™ in the NA assay and both ethers showed increased activity in plaque reduction assays (see Honda et al. *Biorg. Med. Chem. Lett.* 12: 1921-24 (2002); Honda et al. *Bioorg. Med. Chem. Lett.* 12: 1925-28 (2002)). In general, compounds with alkyl ethers of less than 12 carbons showed potent (nM) inhibition of NA and improved activity relative to ZANAMIVIR™ in cell-culture assays. These combined studies indicate that modifications of the glycerol side-chain of ZANAMIVIR™ are tolerated and often beneficial.

Solution-phase neuraminidase inhibition assays normally use the fluorogenic substrate, 2'-(4-methylumbelliferyl)-α-D-acetyl-neuraminic acid, which is cleaved by neuraminidase to yield a fluorescent product that can be quantified using a fluorometer (Potier et al., *Anal. Biochem.* 94:287-296 (1979)), however, this assay method is not amenable to a high-throughput format. In addition, due to the fast emergence of resistant viral strains (see McKimm-Breschkin, J. L. *Antiviral Res.* 2000, 47, 1-17), there remains a need to find new influenza neuraminidase inhibitors.

Another pharmaceutically important class of enzymes are sialyl transferases. Glycoconjugates, including glycoproteins, glycosphingolipids, and polysaccharides, play important biological roles in cell-cell recognition, bacterial adhesion, signal transduction, and immune response (see Fukuda, M. "Roles cell surface carbohydrate" in *Molecular and Cellular Glycobiology* (Fukuda and Hindsgaul, eds.); Oxford University Press: New York, 2000, pp 33-44). Many of these biologically active glycans contain an essential nine-carbon sugar which is N-acetyl-neuraminic acid (NeuAc). For example, gangliosides are one of the biologically important sialylated glycosphingolipids found in vertebrate cells, nerve cells, as well as in the brain (see Vyas and Schnaar *Biochimie* 2000, 83, 677-682). In vivo sialylations are catalyzed by a family of enzymes known as sialyltransferases, which contribute to the diversity in the linkage and the chemical structure of sialic acid residues on cell-surface glycoconjugates. Different sialyl-linkages (α-2,3, α-2,6, α-2,8) are elaborated by different sialyltransferases, which share the same donor substrate cytidine monophosphate-sialic acid (CMP-Neu5Ac) but differ in acceptors (see Harduin-Lepers, A. et al. *Biochimie* 2001, 83, 727-737). Sialyltransferase activity has been shown to correlate with cancer progression and several reasons have been postulated to explain this behavior (see Platt, F. M. et al. *Science* 1997, 276, 428-431). For example, sialic acids can prevent cell-cell interactions through non-specific charge repulsion effects, which may facilitate metastasis. Secondly, sialyated glycoconjugates can be specifically bound by cell adhesion molecules such as selecting, allowing extravasation of cancer cell (see Feizi, T. *Immunol. Rev.* 2000, 173, 79-88; and Colin-Hughes, R. *Biochimie* 2001, 83, 667-676).

CMP-Neu5Ac

CMP-Neu5Ac‡

Like neuraminidases, the important biological activity of sialyltransferases has prompted chemists to design specific inhibitors of sialyltransferases for elucidating the role of sialyl residues in biological systems (see Wang, X. F. et al. *Med. Res. Rev.* 2003, 23, 32-47). Several sialyltransferase inhibitors have been developed mostly as CMP-Neu5Ac donor analogues, (see Klohs, W. D. et al. *Cancer Res.* 1979, 39, 1231-1238; Cambron, L. D. and Leskawa, K. C. *Biochem. Biophys. Res. Commun.* 1993, 93(2), 585-590; Schaub, C. et al. *Glycoconj. J.* 1998, 15(4), 345-354; Kijima-Suda, I. et al.

*Cancer Res.* 1986, 46, 858-862; Cohen, S B. and Halcomb, R. L. *J. Org. Chem.* 2000, 65, 6145-6152; Imamura, M. and Hashimoto, H. *Tetrahedron Lett.* 1996, 37(9), 1451-1454; Müller, B. et al. *Tetrahedron Lett.* 1998, 39, 509-512; Amann, F. et al. *Chem. Eur. J.* 1998, 4(6), 1106-1115; and Compain, P. and Martin. O. V. *Bioorg. Med. Chem.* 2001, 9, 3077-3092), transition-state analogues, (see Müller, B. et al. *Angew. Chem. Int. Ed.* 1998, 37(20), 2893-2897; Schwörer, R. and Schmidt, R. R. *J. Am. Chem. Soc.* 2002, 124, 1632-1637; Schröder, P. N. and Giannis, A. *Angew. Chem. Int. Ed.* 1999, 38(10), 1379-1380; Sun, H. B. et al. *Tetrahedron Lett.* 2001, 42, 2451-2453; and Paul, P. et al. *J. Biol. Chem.* 1993, 268, 12933-12938, and sugar-acceptor analogues (see Kajihara, Y. et al. *J. Carbohydr. Chem.* 1993, 12(7), 991-996; and *Carbohydr. Res.* 1993, 247, 179-193).

However, all the known potent sialyltransferase inhibitors are polar and charged. These inhibitors have difficulty exerting their functions in cells or organisms due to low membrane permeability (see Platt, F. M. et al. *Science* 1997, 276, 428-431). There remains a need for the identification of cell-permeable sialyltransferase inhibitors for in vivo biological study and as pharmaceuticals.

Current sialyltransferase assays use radio-active or fluorescence labeled cytidine monophosphate N-acetylneuraminic acid (CMP-Neu5Ac) donor, and fluorescence or ultraviolet (UV)-labeled acceptor (see Paulson, J. C. et al. *J. Biol. Chem.* 1977, 252, 2363-2371; Gross, H. J. et al. *Anal. Biochem.* 1990, 186, 127-134; Limberg, G. et al. *Liebigs. Ann.* 1996, 1773-1784; and Schaub, C. et al. *Glycoconj. J.* 1998, 15(4), 345-354). These assays require separation of product from donor and acceptor, and are not convenient for the determination of kinetic parameters.

Combinatorial chemistry has developed into a useful method for the rapid identification of lead compounds for drug discovery (see Lam et al. *Nature* 1991, 354, 82-84; Lam et al. *Chem. Rev.* 1997, 97(2), 411-448; Pirrung et al. *Chem. Rev.* 1997, 97(2), 473-488; Nefzi et al. *Chem. Rev.* 1997, 97(2), 449-472; Young et al. *Curr. Opin. Drug Discovery Dev.* 2004, 7(3), 318-324). The first step in the process is the facile identification of positive hits from a large collection of compounds. In cases where libraries are prepared in solution, NA activity can be monitored using a synthetic substrate 2'-(4-methylumbelliferyl)-α-D-N-acetylneuraminic acid which is cleaved to yield a fluorescent product (4-methylumbelliferone) that can be quantified fluorometrically (see Hochgurtel et al. *Proc. Natl. Acad. Sci. USA* 2002, 99, 3382-3387; Potier et al. *Anal. Biochem.* 1979, 94, 287-296). Solution phase assays are not applicable to one-bead-one-compound libraries because it is impossible to identify the bead providing the activity.

Therefore there is a need for the rapid identification of new inhibitors for developing new drugs for the treatment of new and existing strains of flu virus. There also remains a need for a high-throughput screening method for enzyme inhibitors, specifically neuraminidase inhibitors and sialyltransferase inhibitors. The present invention solves this problem by providing an on-bead assay of enzymes, which allows simultaneous monitoring of substrate cleavage and inhibitor efficiency. The substrates and methods for identifying enzyme inhibitors of the present invention can be used in screening of large libraries of compounds for their enzyme inhibitory properties.

BRIEF SUMMARY OF THE INVENTION

In one aspect the present invention provides a detectable label-substrate conjugate comprising a detectable label covalently attached to the substrate of a enzyme. In another aspect, modification of the substrate causes a detectable change in the label.

In one aspect, the present invention provides an assay complex, such as that shown in FIG. 11, comprising a solid support having at least one test ligand attached thereto and at least one attached detectable label-substrate conjugate. The detectable label-substrate conjugate comprises a detectable label covalently attached to the substrate of an enzyme. Modification of the substrate causes a detectable change in the label.

In another aspect, the present invention provides an assay complex comprising at least one test ligand and at least one detectable label-substrate conjugate comprising a detectable label covalently attached to a first substrate of an enzyme and a quencher attached to a second substrate of said enzyme wherein modification of said substrates causes a detectable change in said label and either said detectable label covalently attached to a first substrate of said enzyme or said quencher attached to a second substrate of an enzyme is attached to a solid support.

In another aspect, the present invention relates to a method of identifying an enzyme inhibitor, specifically a neuraminidase or a sialyltransferase inhibitor, by combining in a assay mixture an assay complex of the present invention and a sufficient quantity of the enzyme to react with the substrate under noninhibitory conditions. The detection of a change in the label upon combining with the enzyme indicates the absence of an enzyme inhibitor. The assay complex is designed such that the presence of an enzyme inhibitor prevents the enzyme from modifying the substrate and causing a change in said detectable label. As such, test ligands which prevent a detectable change in the label can be identified as enzyme inhibitors.

BRIEF DESCRIPTION OF THE DRAWINGS

FIG. 2 illustrates modeled complexes of DANA with bacterial NA crystal structure showing the hydrophobic pocket that is accessible at C-7. FIG. 2a shows DANA with *Samonella typhimurium* Neuraminidase (Crennell, S. J. et al. *J. Mol. Biol.* 1996, 259, 264). FIG. 2b shows DANA with *Vibrio cholerae* Neuraminidase (Ca dependent) (Crennell, S. et al. *Structure* 1994, 2, 535-544).

FIG. 3 illustrates a parallel solid phase synthetic approach to NA inhibitors.

FIG. 7 illustrates the parallel synthesis of a library using a ZANAMIVIR™ core.

Figure 8:
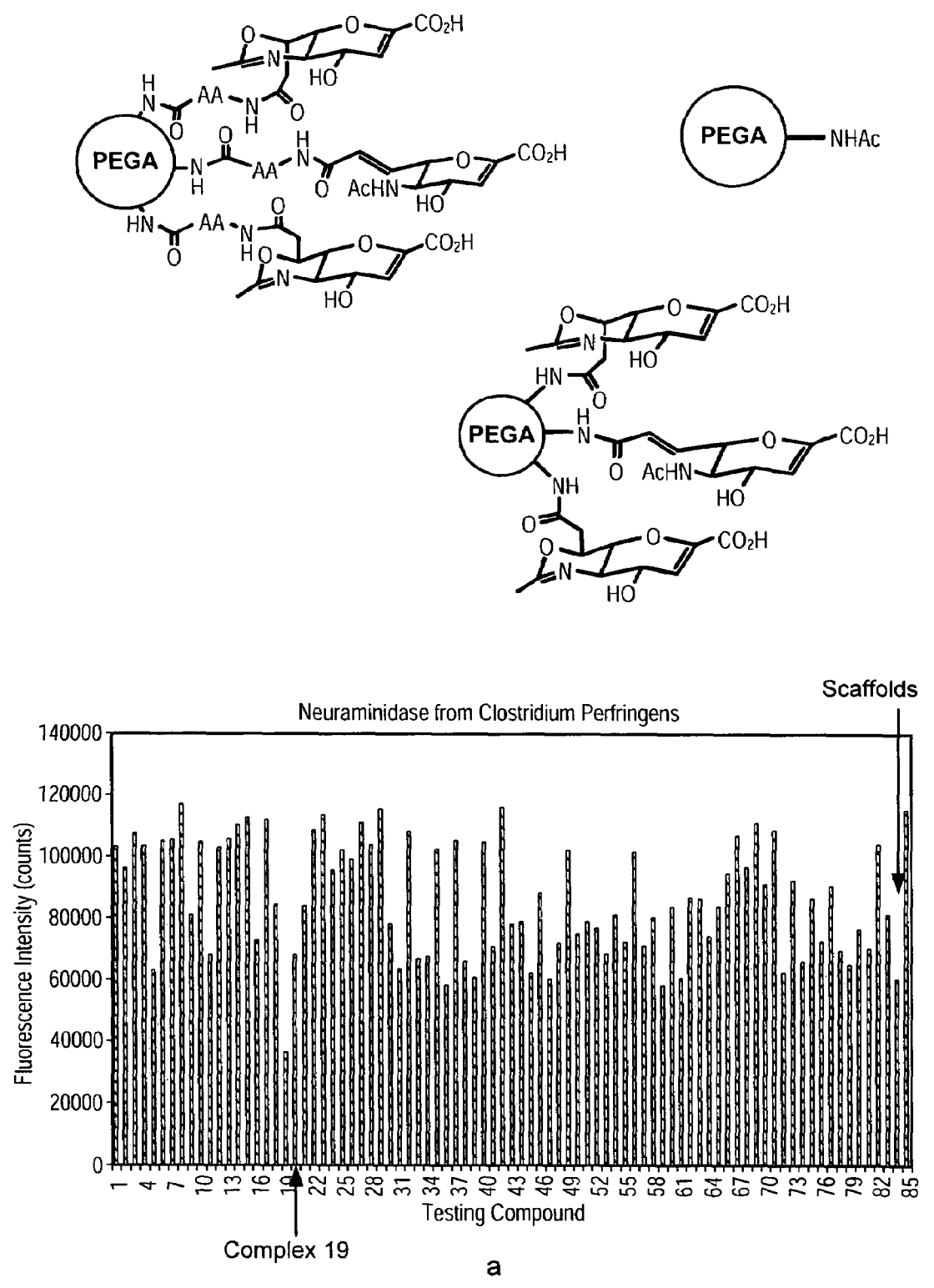

FIG. 8 illustrates the screening results of a DANA-based library. FIG. 8a identifies complex 19 and scaffolds. FIG. 8c identifies 3 possible hits with *Vibrio*.

FIG. 19a illustrates poly(ethyleneglycol) polyacrylamide (PEGA) functionalized beads 14 after incubation with *Vibrio cholerae*. FIG. 19b illustrates PEGA functionalized beads 15 after incubation with *Vibrio cholerae*. FIG. 19c illustrates PEGA functionalized beads 16 after incubation with *Vibrio cholerae*.

DETAILED DESCRIPTION OF THE INVENTION

Abbreviations and Definitions

The abbreviations used herein are conventional, unless otherwise defined:

Unless otherwise stated, the following terms used in the specification and claims have the meanings given below:

The term "test ligand" is used in this disclosure to describe any compound that is desirably screened for potential enzyme inhibitory activity. It includes, but is not limited to e.g. a protein, oligopeptide, small organic molecule, polysaccharide, polynucleotide and the like. It can be a natural product, a synthetic compound, a chemical compound or a combination of two or more substances.

"High-throughput screening" or "HTS" refers to methods for simultaneously assaying a large number of test ligands for their ability to inhibit an enzyme, particularly neuraminidase. In general, many steps of these assays can be performed using automated equipment.

"Immobilization" refers to methods for attaching a molecule to a solid support either through covalent or non-covalent interactions with the surface of the solid support.

General Description of the Embodiments

In one aspect, the present invention provides a detectable label-substrate conjugate comprising a detectable label which is attached to an enzyme substrate. In this aspect the detectable label is quenched when it is conjugated with the substrate. Once substrate is cleaved by the enzyme, the detectable label will no longer be quenched and will show a detectable change, for example, fluorescence.

In another aspect of the present invention, the detectable label-substrate conjugate is used in solution in combination with a test ligand for high-throughput screening of potential enzyme inhibitors. The test ligands may be in solution or immobilized on solid phase supports (see e.g. FIG. 3).

In another aspect of the present invention, the detectable label-substrate conjugate is attached to solid support in combination with a test ligand for high-throughput screening of potential enzyme inhibitors.

Figure 11:
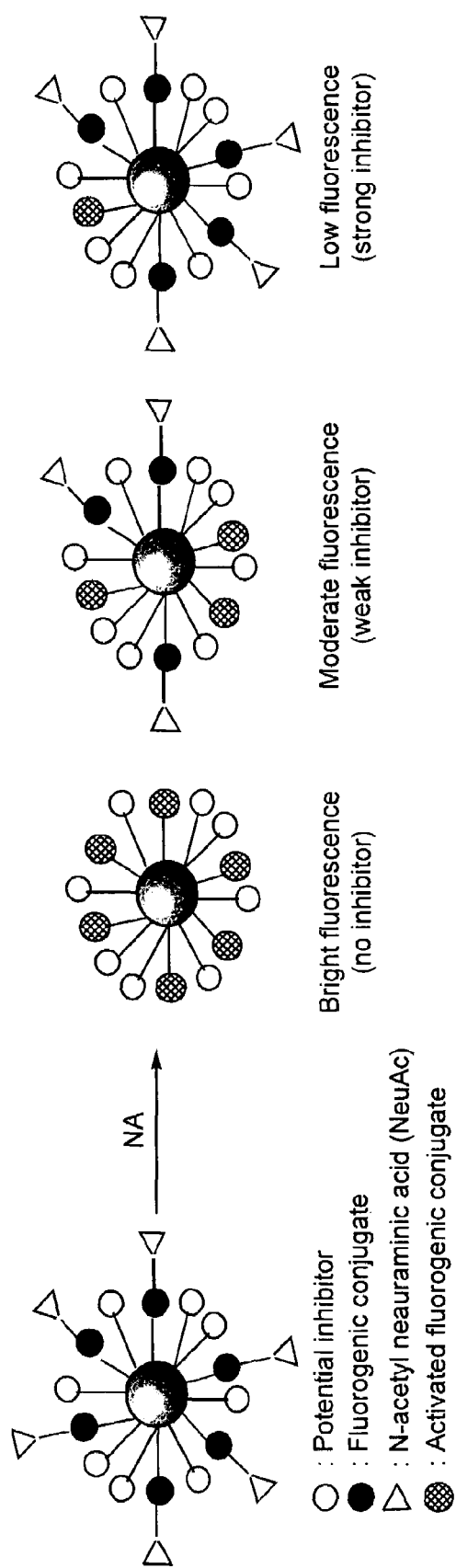
FIG. 11 illustrates a high throughput on-bead screening approach for combinatorial libraries of Neuraminidase Inhibitors.

In another aspect, the present invention provides a method for identifying potential enzyme inhibitors, specifically neuraminidase or sialyltransferase inhibitors (see e.g. FIG. 11). In this method, a detectable label-substrate conjugate and a test ligand are combined with an enzyme which may modify the substrate. This modification may take the form of cleaving the substrate from the detectable label or ligating a second substrate onto the first substrate attached to the detectable label. If the test ligand shows no inhibition, the enzyme will quickly cleave the substrate from the detectable label-substrate complex or ligate a second substrate onto the detectable label-substrate complex. Either scenario causes a detectable change in the detectable label, such as fluorescence. If the test ligand is a strong inhibitor of the enzyme, the detectable label does not change and the support containing the test ligand will be picked out as positive hit for structure characterization. The test ligands may be in solution or immobilized on solid phase supports (see e.g. FIG. 3).

Another aspect of the present invention is to provide efficient HTS methods for screening enzyme inhibitors both in solution and on solid-support.

Detectable Label-Substrate Conjugates and their Synthesis

In one aspect, the present invention provides a detectable label-substrate conjugate comprising a detectable label which is attached to an enzyme substrate. In this aspect the detectable label is quenched when it is conjugated with the substrate. Once substrate is cleaved by the enzyme, the detectable label will no longer be quenched and will show a detectable change, for example, fluorescence.

For the purposes of the present invention suitable detectable labels, include but are not limited to fluorophores, colorometric labels, radiolabels, and the like.

For the purposes of the present invention any enzyme substrate may be used. Preferred substrates depend on the particular application of the detectable label-substrate conjugate. For example, if the detectable label-substrate complex is to be used in an enzyme assay, preferred substrates are the natural substrates of the enzyme to be assayed. For example if the enzyme to be assayed is a neuraminidase, then examples of suitable substrates include, but are not limited to sialic acid, and the like. If the enzyme to be assayed is a sialyltransferase then examples of suitable substrates include, but are not limited to sialic acid and the like. Other enzyme and substrate combinations are well known to those of skill in the art.

For ease of illustration, this aspect of the present invention will first be illustrated by conjugates for use in a neuraminidase assay. The synthesis of an on-bead fluorogenic neuraminidase substrate conjugate is shown in Scheme 1. 7-Hydroxy-4-methylcoumarin 1 is

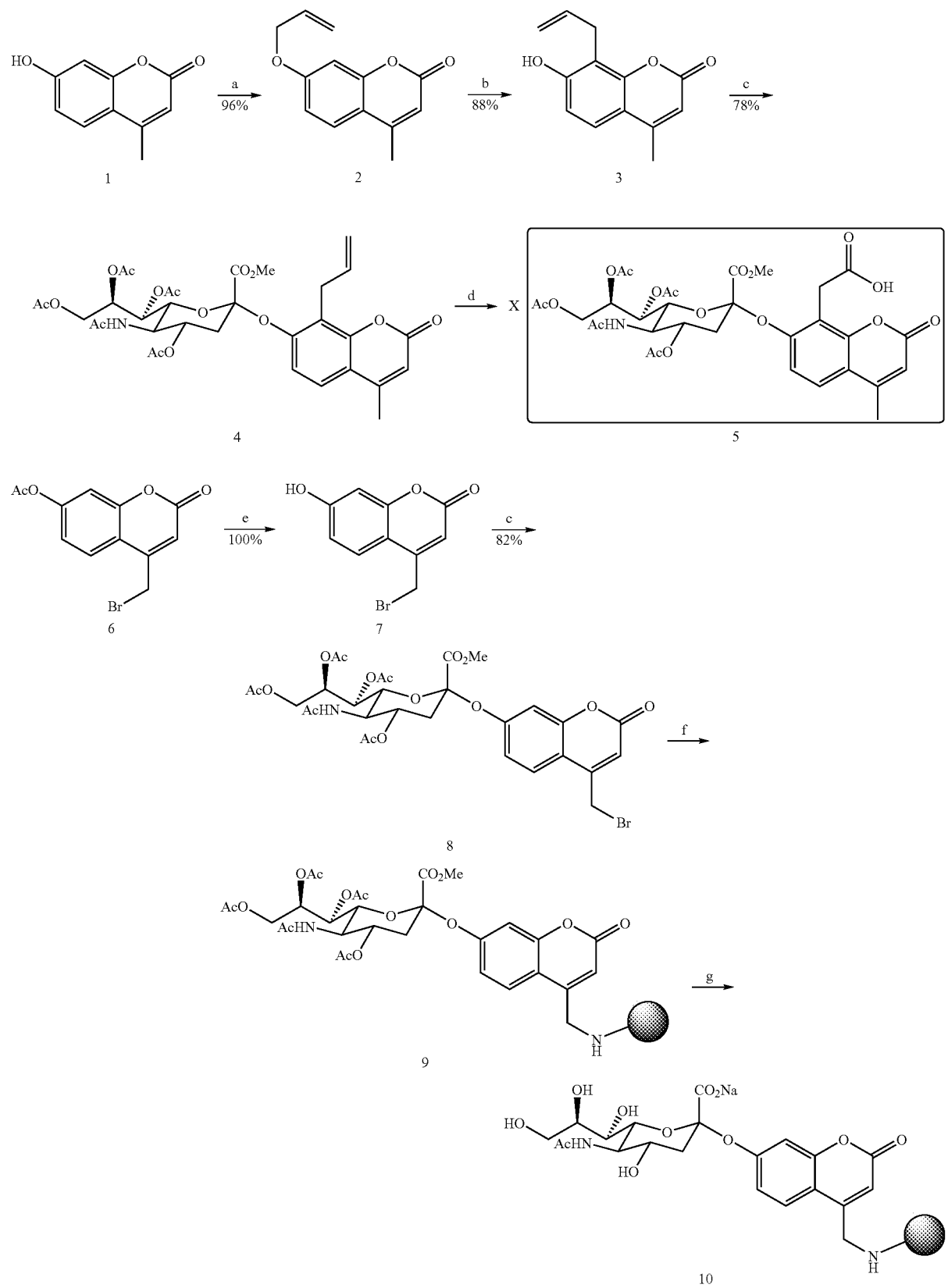
Scheme 1.

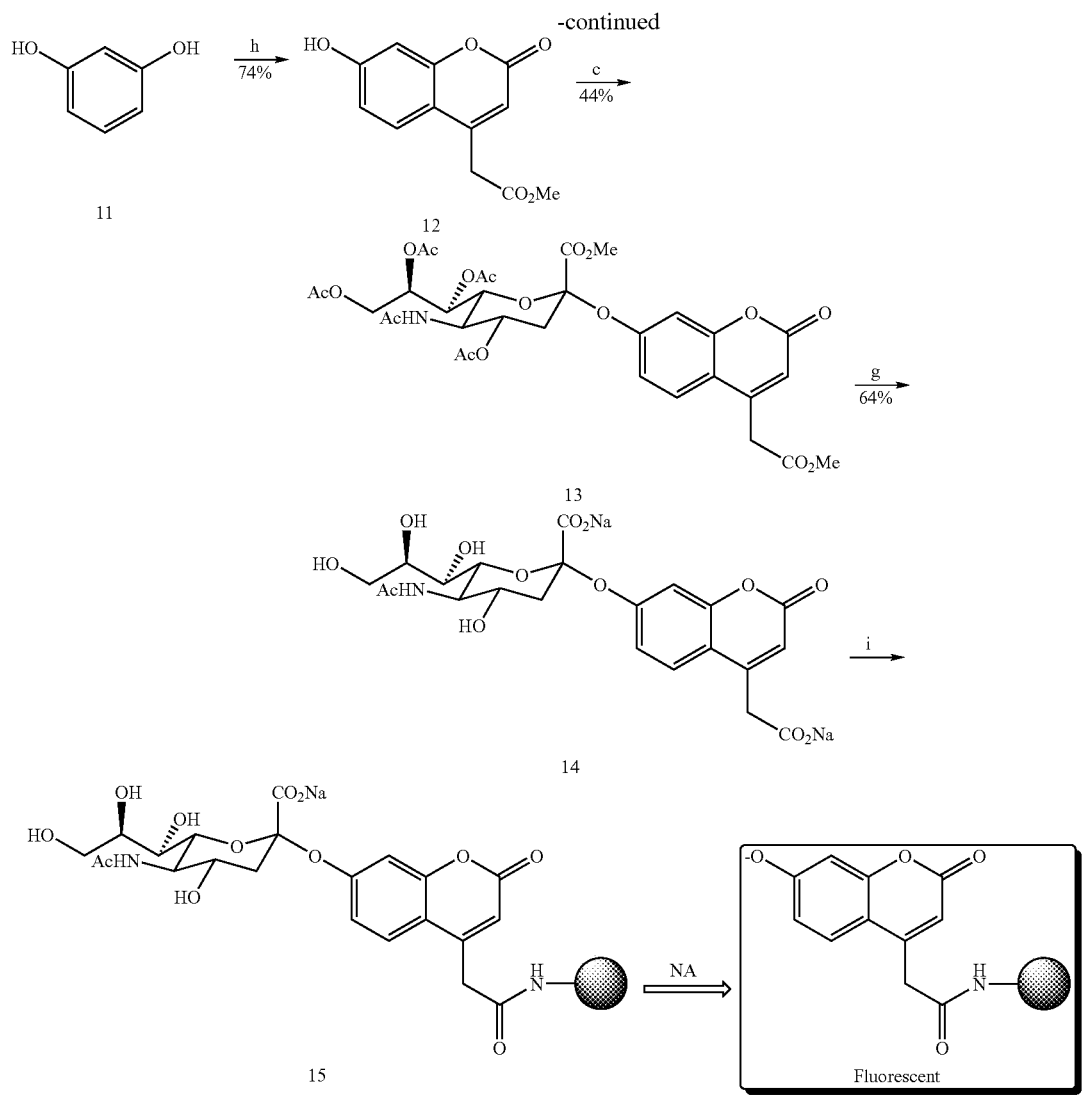

a. Allyl bromide, K₂CO₃, acetone;
b. N,N-Diethylaniline;
c. 2-Deoxy-2-chloro-4,7,8,9-tetra-O-acetyl-N-acetylneuraminic acid, Ag₂CO₃, CH₃CN;
d. RuO₂, NaIO₄,CCl₄/CH₃CN/H₂O;
e. NaOMe, MeOH;
f. DIEA, DMF;
g. NaOMe, MeOH; aq. NaOH;
h. 1,3-Acetonedicarboxylic acid, 70% H₂SO₄; SOCl₂, MeOH;
i. HOBt, DIC, DMF.

reacted with allyl bromide in the presence of $K_2CO_3$ to give 2 (see Clarke, D. J. and Robinson, R. S. *Tetrahedron* 2002, 58, 2831-2837) which can be subsequently rearranged under microwave conditions to afford regioselective product 3 (see Saidi, M. R. and Rajabi, F. *Heterocycles* 2001, 55, 1805-1812) Glycosylation of 2-deoxy-2-chloro-4,7,8,9-tetra-O-acetyl-N-acetylneuraminic acid methyl ester with 3 using silver carbonate in the presence of activated molecular sieves gives 4 (see Potier, M. et al. *Anal. Biochem.* 1979, 94, 287-296). The acetyl group of substrate 4-bromomethyl-7-acetoxycoumarin 6 is quantitatively removed with sodium methoxide, followed by glycosylation with 2-deoxy-2-chloro-4,7,8,9-tetra-O-acetyl-N-acetylneuraminic acid methyl ester to give the protected substrate 8. The substrate 8 can be immobilized on a resin before removal of the protecting group. Unprotected substrate 14 can also be synthesized from resorcinol 11. Resocinol 11 is first converted to 7-hydroxycoumarin-4-acetic acid methyl ester 12 (see Zhu, Q. et al. *Organic Lett.* 2003, 5, 1257-1260). Glycosylation of 2-deoxy-2-chloro-4,7,8,9-tetra-O-acetyl-N-acetyl-neuraminic acid methyl ester with 12 gave protected substrate 13, followed by deprotection to yield 14.

Substrates can be immobilized on solid supports by methods known in the art. For example, 14 can be immobilized on a resin by standard amide coupling to give 15 (see e.g. M. Meldal *Tet. Lett.* 33: 3077 (1992)).

For the purposes of the present invention suitable solid supports include, but are not limited to beads, slides, chips, and the like.

Confirmation of immobilization can be accomplished by treatment with the appropriate enzyme. For example, the resin 15 showed strong blue fluorescence once it was incubated with neuraminidase.

Other labels can also be used in the detectable label-substrate conjugates of the present invention. For example, as shown in Scheme 2, Fluorescein labeled substrates can also be used as a fluorogenic substrate. Fluorescein 16 is first converted to 17, followed by deprotection of allyl ester to yield 18 (see Zaikova, T. O. et al. *Bioconjugate Chem.* 2001, 12, 307-313). Glycosylation of 18 with 2-deoxy-2-chloro-4,7,8,9-tetra-O-acetyl-N-acetylneuraminic acid methyl ester affords protected substrate 19. Fluorescein 16 can be selectively protected to give the allyl ester 21, followed by alkylation with methyl bromoacetate and deprotection of allyl ester to yield 22 (see Grieco, P. et al. *J. Peptide Research* 2001, 57(3), 250-256). Glycosylation of 22 with 2-deoxy-2-chloro-4,7,8,9-tetra-O-acetyl-N-acetylneuraminic acid methyl ester gives protected substrate 23, which can be deprotected to afford the substrate 24. The substrate 24 was immobilized on the resin by standard amide coupling to give 25. The beads showed strong green fluorescence once the beads were incubated with neuraminidase.

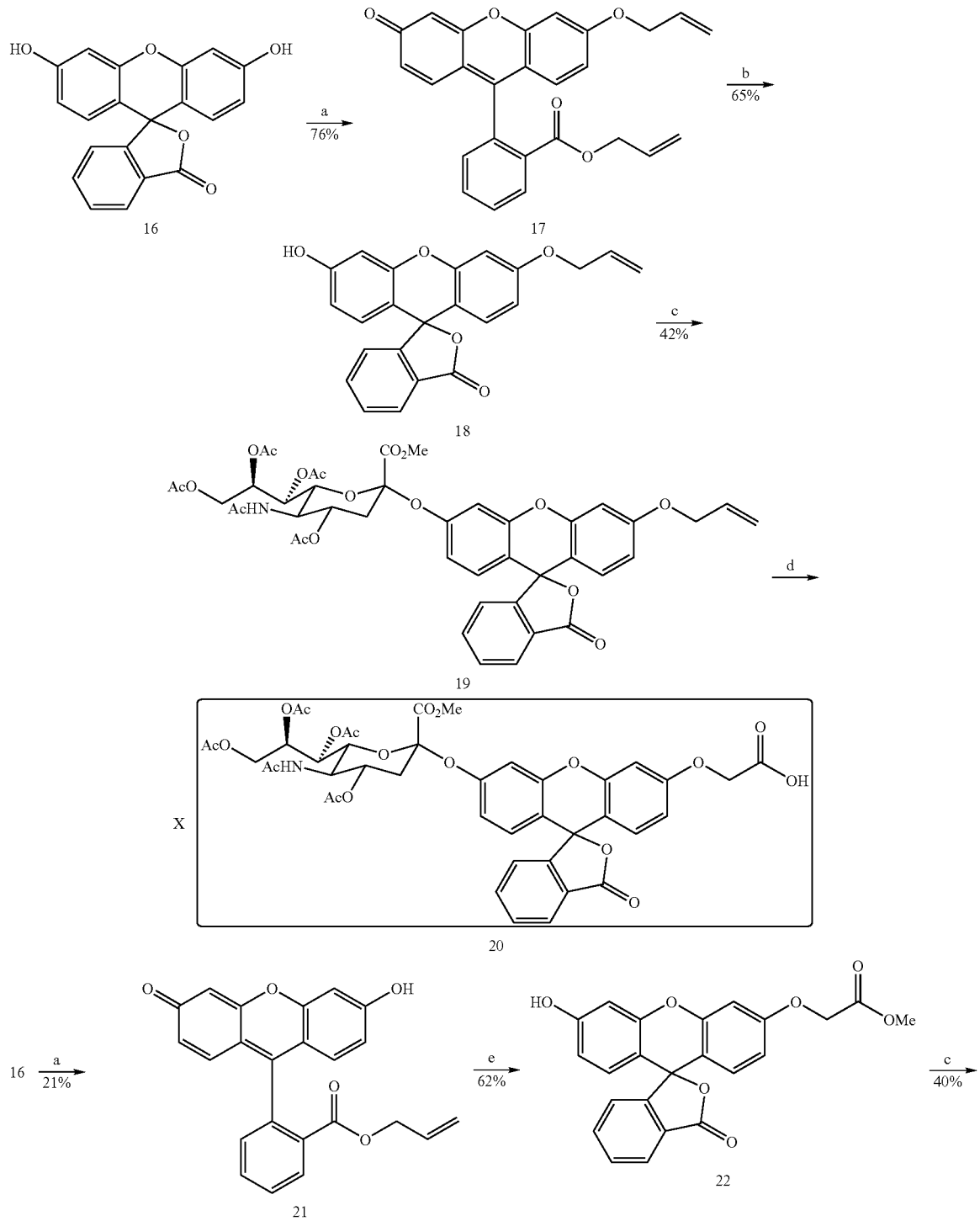

Scheme 2.

-continued

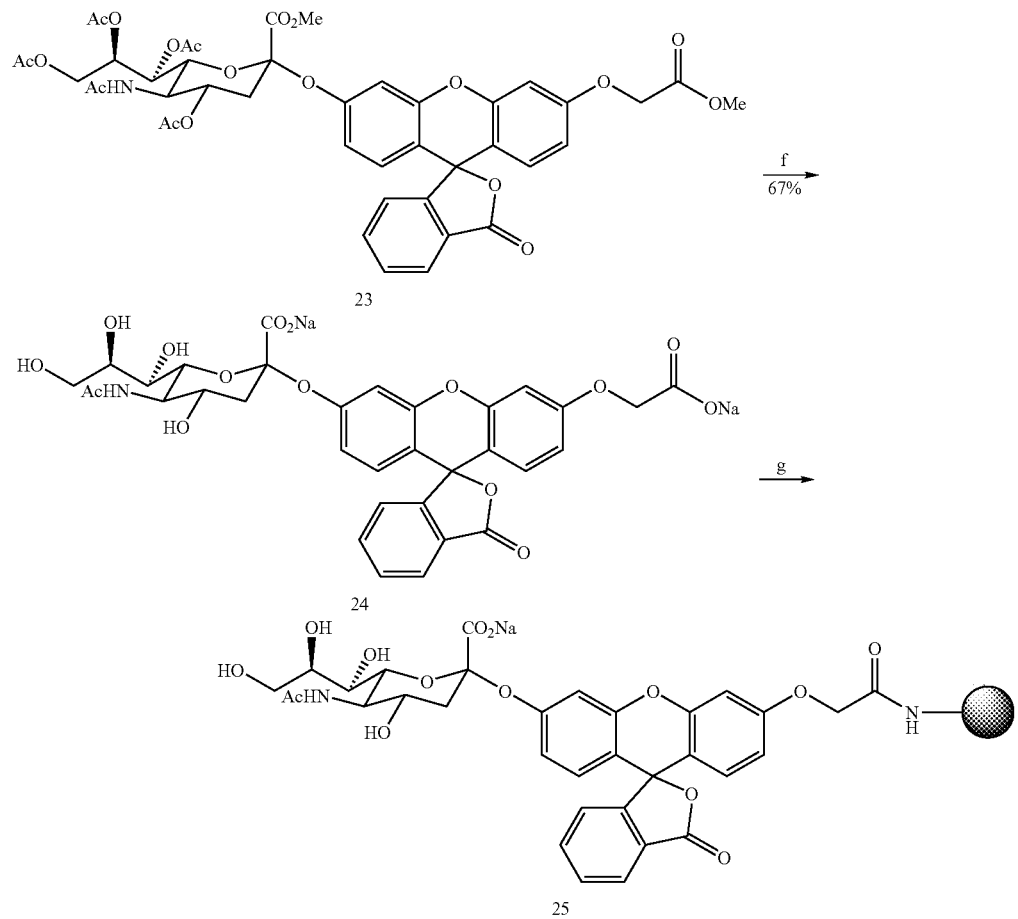

a. Allyl bromide, K$_2$CO$_3$, DMF;
b. aq. NaOH/MeOH;
c. 2-Deoxy-2-chloro-4,7,8,9-tetra-O-acetyl-N-acetylneuraminic acid, Ag$_2$CO$_3$, CH$_3$CN;
d. RuO$_2$, NaIO$_4$, CCl$_4$/CH$_3$CN/H$_2$O;
e. Methyl bromoacetate, K$_2$CO$_3$, DMF; Pd(PPh$_3$)$_4$, PhSiH$_3$, CH$_2$Cl$_2$;
f. NaOMe, MeOH; aq. NaOH;
g. HOBt, DIC, DMF.

Synthesis of Test Ligands

Figure 10:
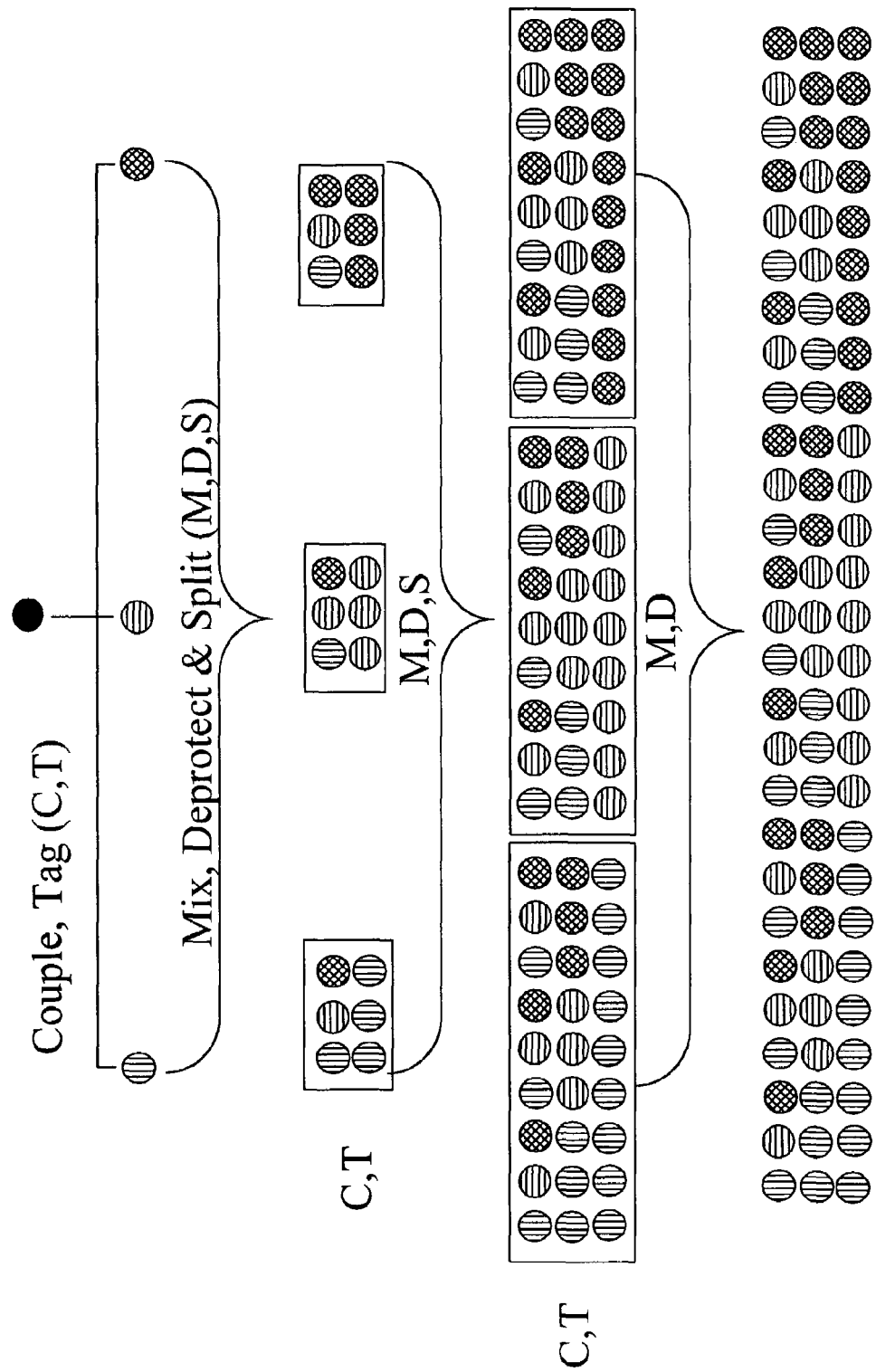
FIG. 10 illustrates combinatorial chemistry approaches to neuraminidase inhibitors and how it requires a method for independently screening each bead.

The ligands to be tested using the methods of this invention as possible enzyme inhibitors are available from a wide variety of sources or may be synthesized by a wide variety of methods known by those skilled in the art. These sources include, but are not limited to, commercially available chemical clearing houses, Sigma, Aldrich, pharmaceutical companies. The composition of these compounds can be wide ranging. They can be organic small molecules, inorganic molecules, carbohydrates, peptides, nucleic acids and mixtures of compounds. The test ligands can be single compounds or multiple compounds such as libraries. Test ligands may be made by traditional synthesis or by combinatorial chemical techniques known in the art of organic synthesis (see FIG. 10).

For example, Schemes 3-4 shows the synthesis of an analog 29 of known neuraminidase inhibitor 2-deoxy-2,3-dehydro-N-acetylneuraminic acid (FIG. 12b) and analog 33 of known neuraminidase inhibitor 4-guanidino-2-deoxy-2,3-didehydro-N-acetylneuraminic acid (Neu5Ac2en) (FIG. 12d), and their attachment to a bead solid support together with a detectable label-substrate conjugate. As shown in Scheme 3, the 8,9-dihydroxy groups of 2-deoxy-2,3-dehydro-N-acetylneuraminic acid methyl ester 26 (see Kirchner, E. et al. *J. Carbohydr. Chem.* 1988, 7, 453-86) can be selectively protected with an isopropylidene protecting group, followed by protection of the 4-hydroxy group with tert-butyldimethylsilyl chloride (TBSCl) to give the intermediate 27 (see Wyatt, P. G. et al. *Bioorg. Med. Chem. Lett.* 2001, 11, 669-673). The 7-hydroxy group of 27 can then be alkylated with methyl bromoacetate to afford 28 (see Masuda, T. et al. *Bioorg. Med. Chem. Lett.* 2003, 13, 669-673). Both of the methyl esters can be removed by aqueous sodium hydroxyide (NaOH) to yield 29.

Scheme 3.

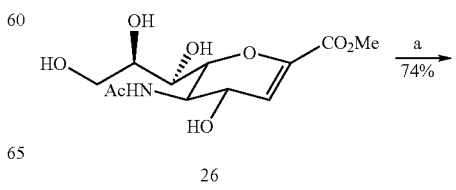

-continued

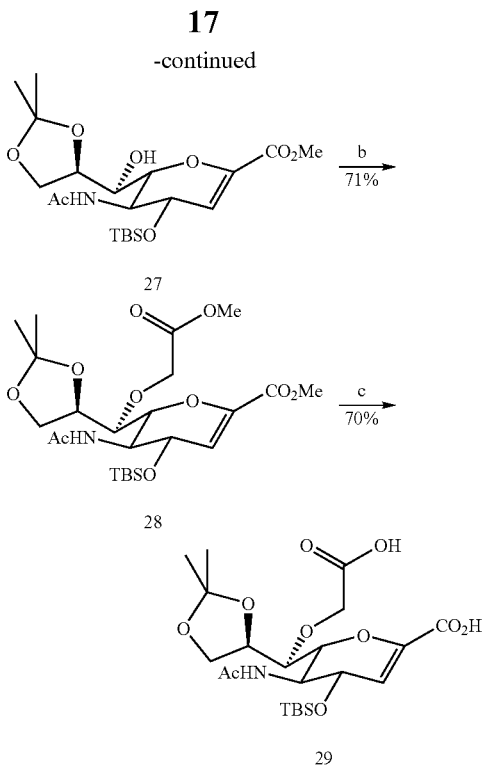

a. 2,2-Dimethoxy propane, acetone, p-TsOH; TBSCl, imidazole, DMF;
b. Methyl bromoacetate, NaH, DMF;
c. aq NaOH, THF.

The synthesis of 4-guanidino-Neu5Ac2en (FIG. 12d) derivative 33 is shown in Scheme 4. The azide 30 can be reduced by hydrogenation over Lindar catalyst, followed by protection of the 4-amino group by guanidinylation with N,N'-bis-tert-butoxycarbonyl-1H-pyrazole-1-carboxamidine (BisBocPCH) to produce the protected guanidine 31 (see Bernatowicz, M. S. et al. *Tetrahedron Lett.* 1993, 34, 3389-3392). After removal of the acetate protecting group using catalytic sodium methoxide in methanol, the 8,9-dihydroxy groups were selectively protected using 2,2-dimethoxy propane and catalytic p-toluenesulfonic acid in acetone to give the 8,9-isopropylidene protected intermediate 32 (see Kirchner, E. et al. *J. Carbohydr. Chem.* 1988, 7, 453-86). Compound 32 can then be treated with 4-nitrophenyl chloroformate and DMAP in dry pyridine to generate the active ester 33 (see Andrews, D. M. et al. *Eur. J. Med. Chem.* 1999, 34, 563-574).

Scheme 4.

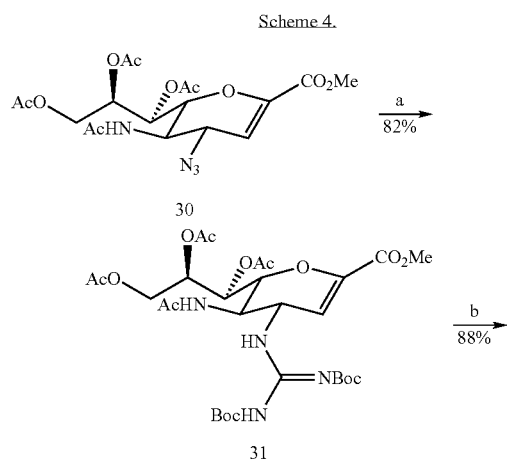

-continued

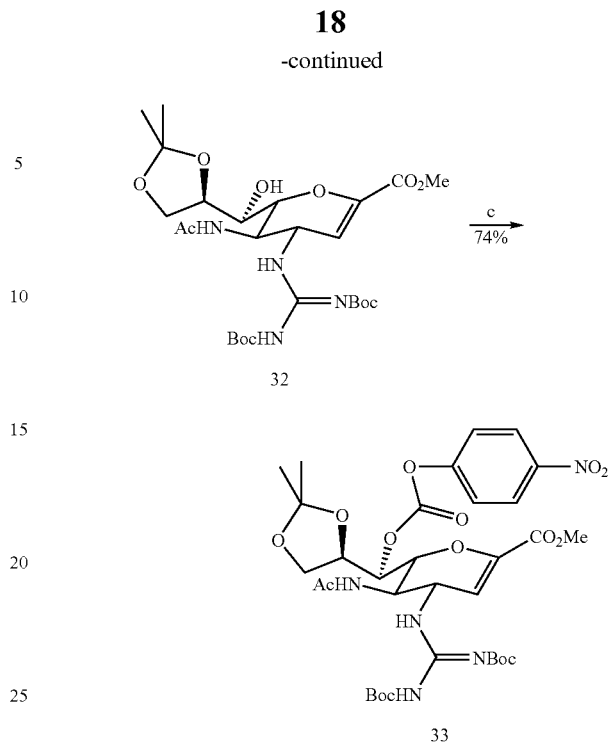

a. Lindar cat., H$_2$, EtOH; N,N'-bis(tert-butoxycarbonyl)-1H-pyrazole-1-carboxamidine, TEA, THF;
b. NaOMe, MeOH; 2,2-dimethoxy propane, acetone, p-TsOH;
c. p-NO$_2$C$_6$H$_4$OCOCl, DMAP, Pyridine.

Figure 1:
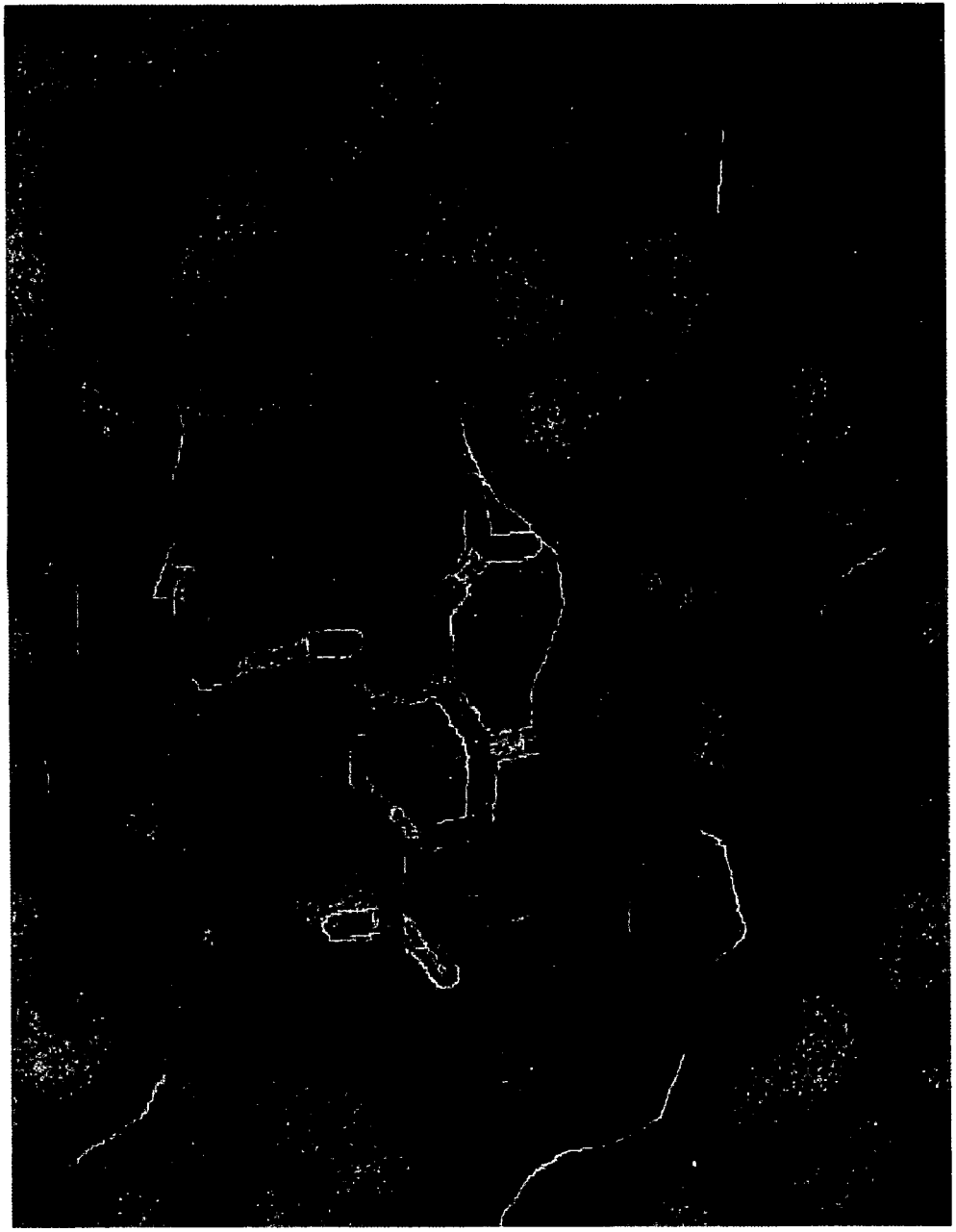
FIG. 1 illustrates the crystal structure of ZANAMIVIR™ bound to Influenza A showing the pocket that is accessible at C-7 and, therefore, why C-7 analogs of ZANAMIVIR™ are potentially potent (von Itzstein, M. et al. *Nature,* 1993, 363, 418-423; Taylhell, N. R. et al. *J. Med. Chem.* 1998, 41, 798-807).
Figure 4:
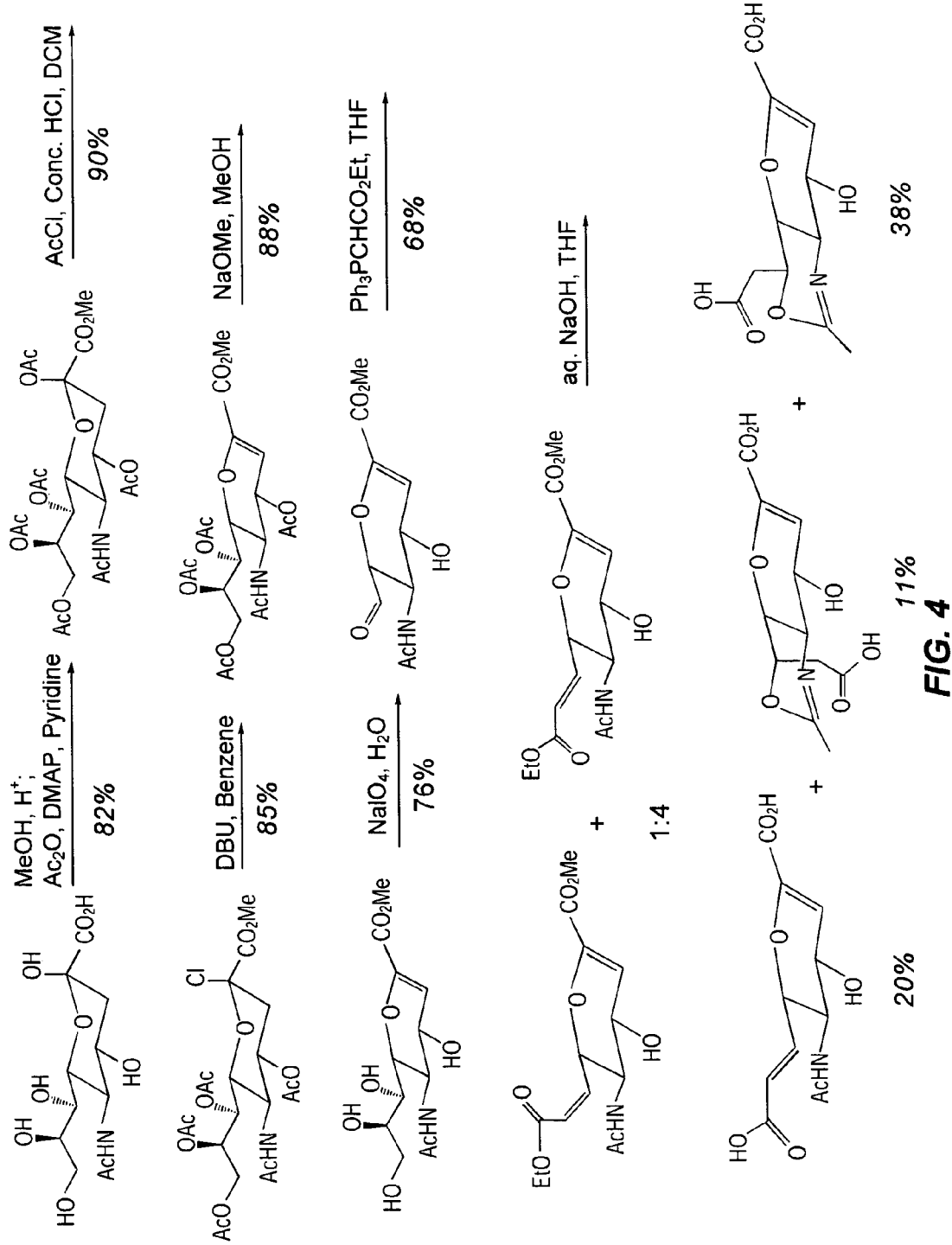
FIG. 4 illustrates synthetic approaches to C-7 functionalized DANA cores as bacterial neuraminidase inhibitors.
Figure 5:
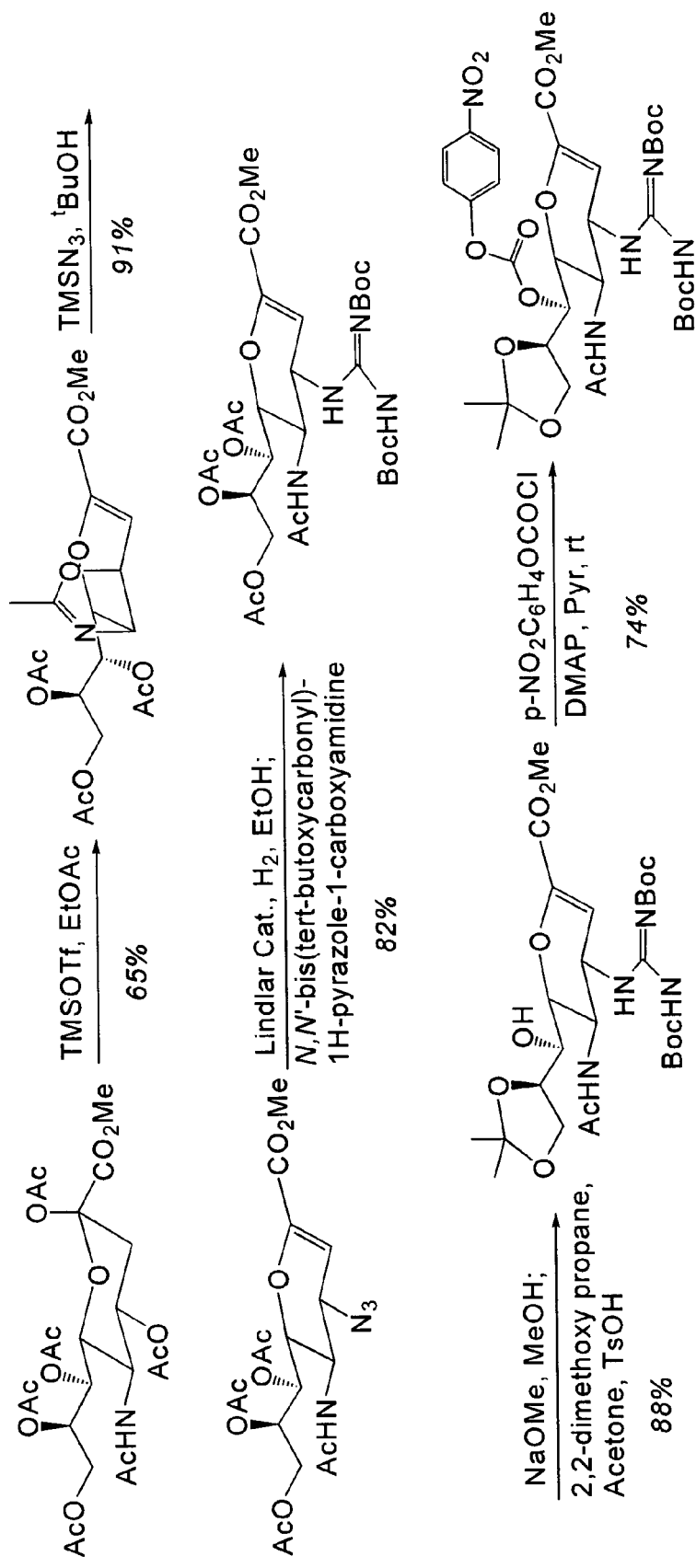
FIG. 5 illustrates synthetic approaches to C-7 functionalized ZANAMIVIR™ cores as bacterial neuraminidase inhibitors.

Similarly, FIGS. 4 and 5 illustrate synthetic approaches to C-7 functionalized DANA and ZANAMIVIR™ cores, respectively, as bacterial neuraminidase inhibitors.

The test ligands can be used in solution or attached to a solid support and Scheme 5 illustrates one embodiment synthesizing one-inhibitor/one-substrate functionalized beads. For example, PEGA resin can be functionalized with orthogonal protecting groups by coupling with a mixture of 9-fluorenylmethoxycarbonyl (Fmoc) protected glycine and tert-butyloxycarbonyl (Boc) protected glycine (9:1) (Scheme 5) (see also Liu et al. *J. Am. Chem. Soc.*, 2002, 124, 7678-7680; Bennett et al.; Saneii, H. H. eds. In *Advanced ChemTech Handbook of combinatorial and solid phase organic chemistry—a guide to principles, products and protocols*. 1998, pp 330, Advanced Chemtech). After removal of Fmoc protecting group using 20% piperidine in dimethylformamide (DMF), compound 29 can be coupled to the beads using 1-hydroxybenzotriazole (HOBt) and diisopropylcarbodiimide (DIC). The tertiary-butyl silyl (TBS) group can be deprotected using tetrabutyl ammonium fluoride (TBAF) in tetrahydrofuran (THF). After removal of tertiary-butoxy carbonyl (Boc) and isopropylidene groups using trifluoroacetic acid (TFA) in dichloromethane (DCM), the beads can be coupled with the fluorogenic substrates 14 and 24 individually. Using the same methodology, compound 33 can also immobilized on orthogonally protected resin. The resin can then be conjugated with substrates 14 and 24 individually. Orthogonally protected resin that is also conjugated with substrates 14 and 24 after acylation can be used as a control.

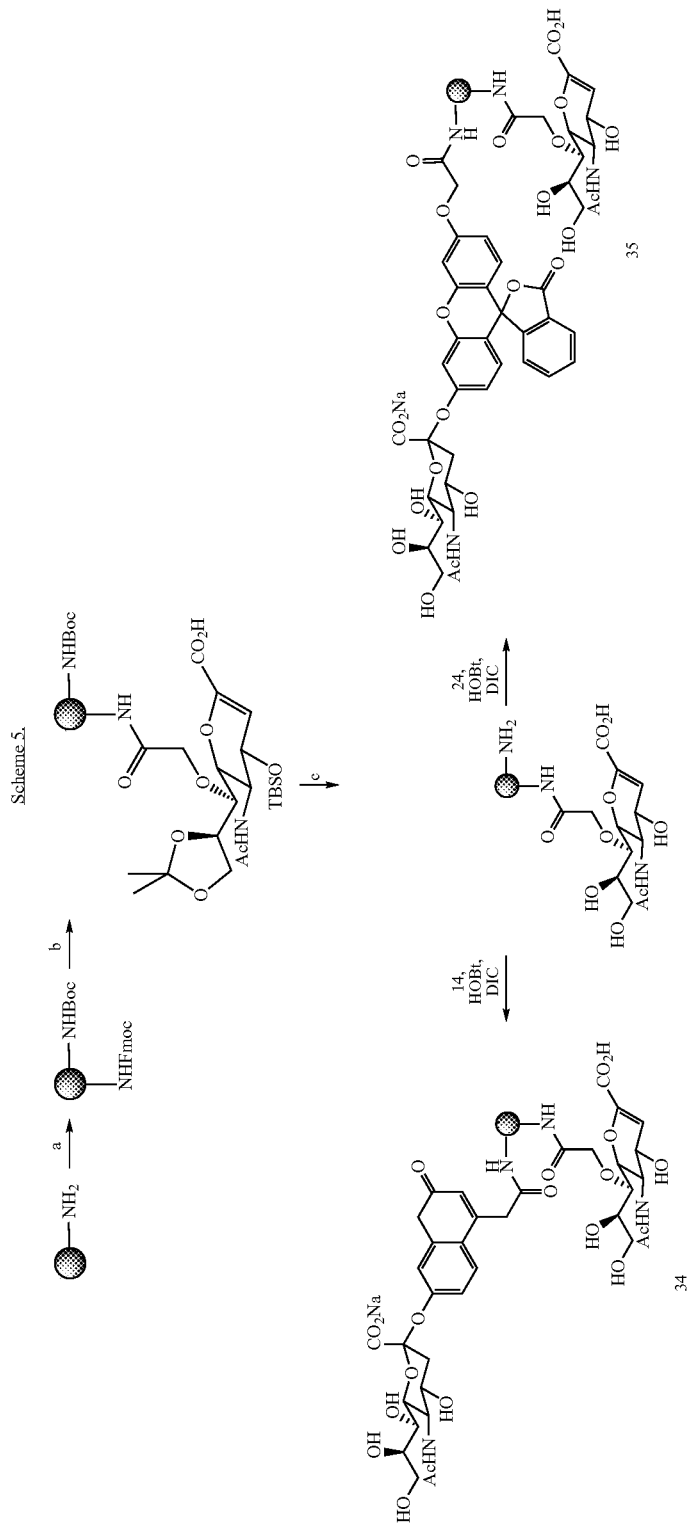

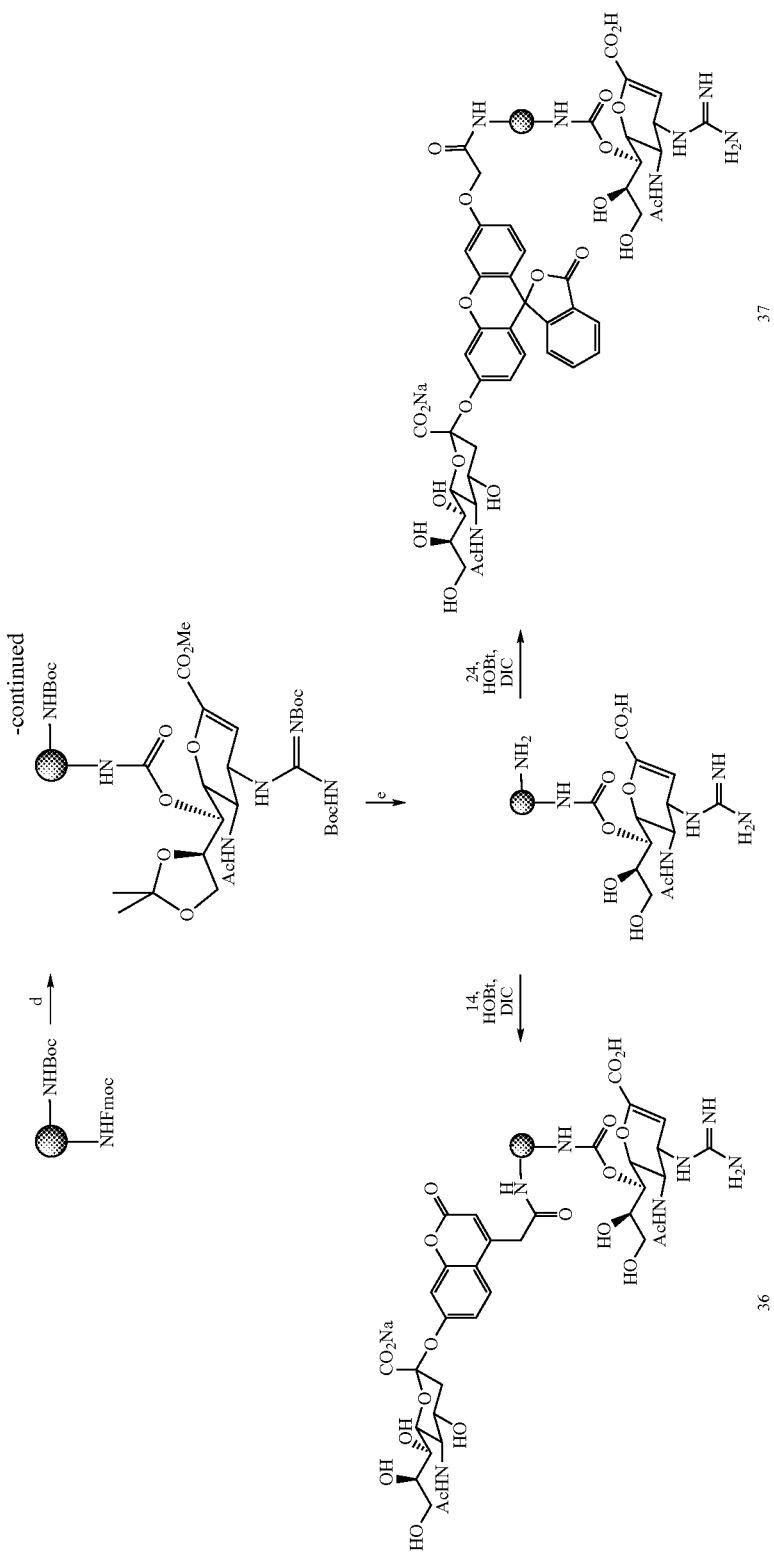

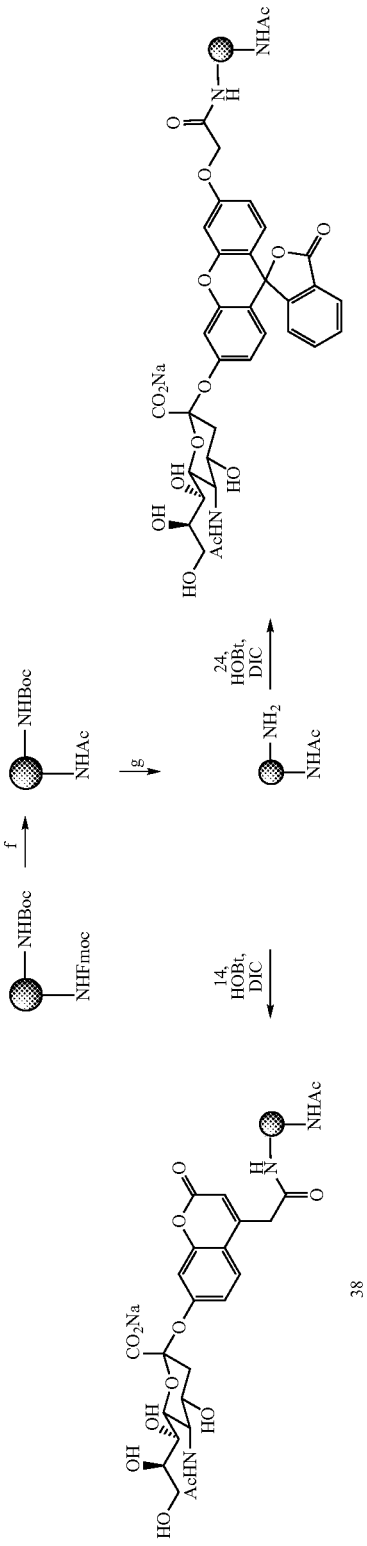

Figure 6:
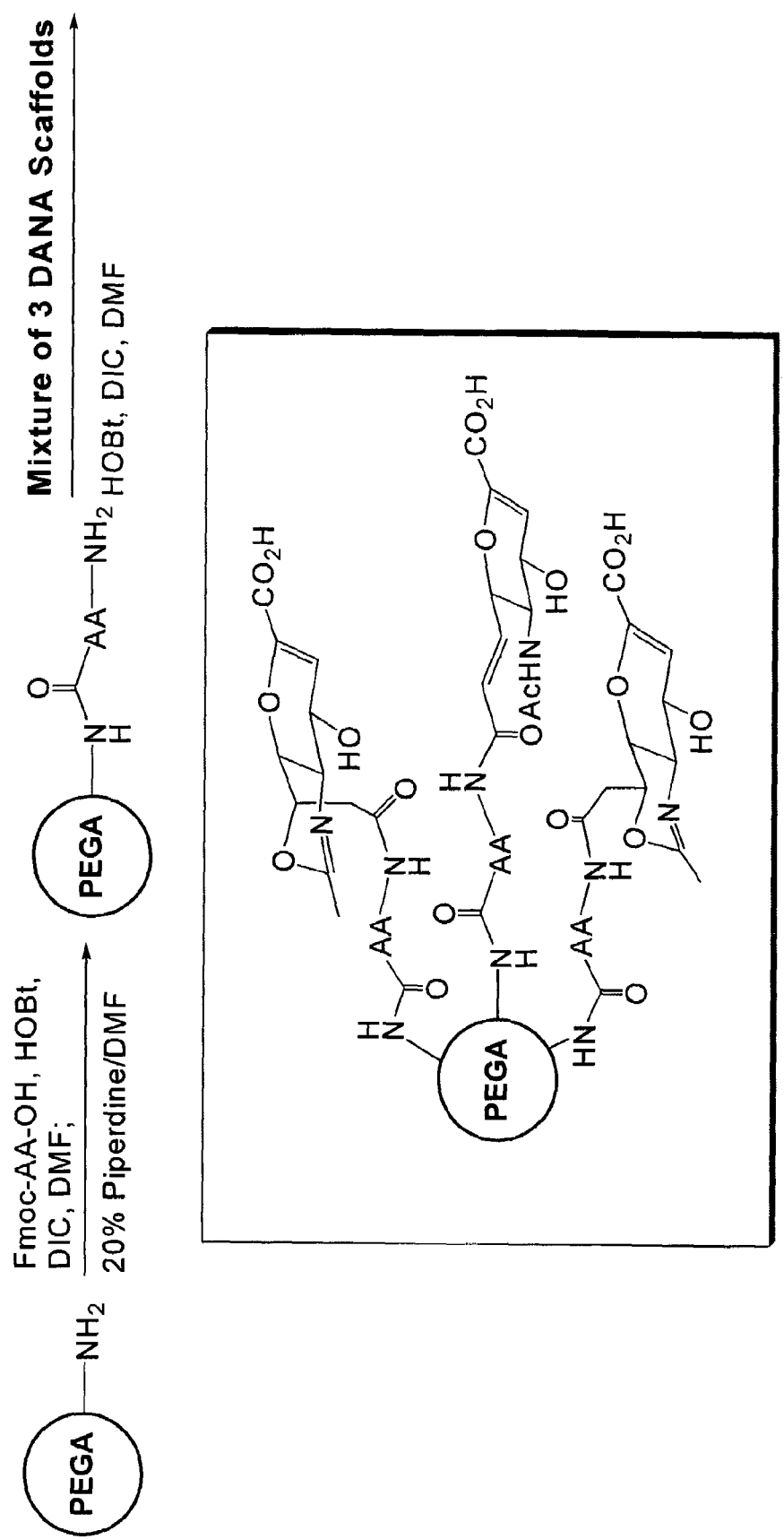
FIG. 6 illustrates the parallel synthesis of a library using three different DANA cores. Each bead has three different cores coupled to the same amino acid.
Figure 7:
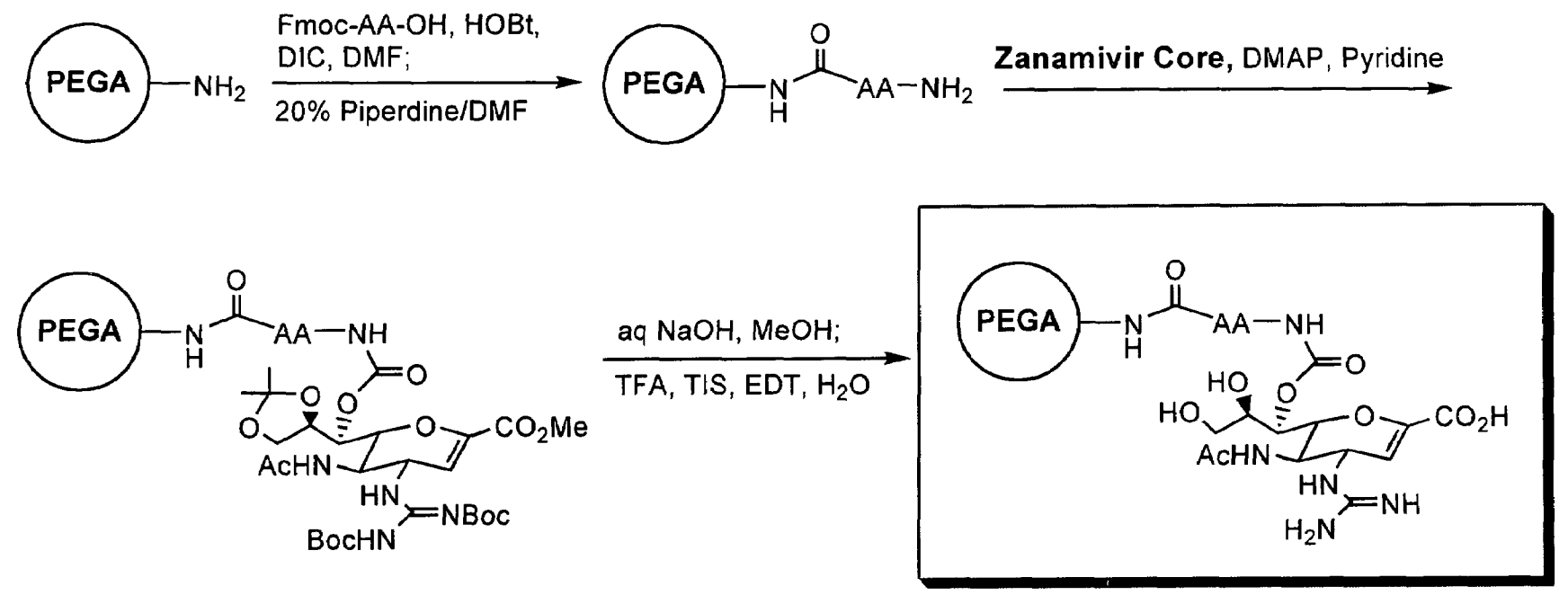
Figure 9:
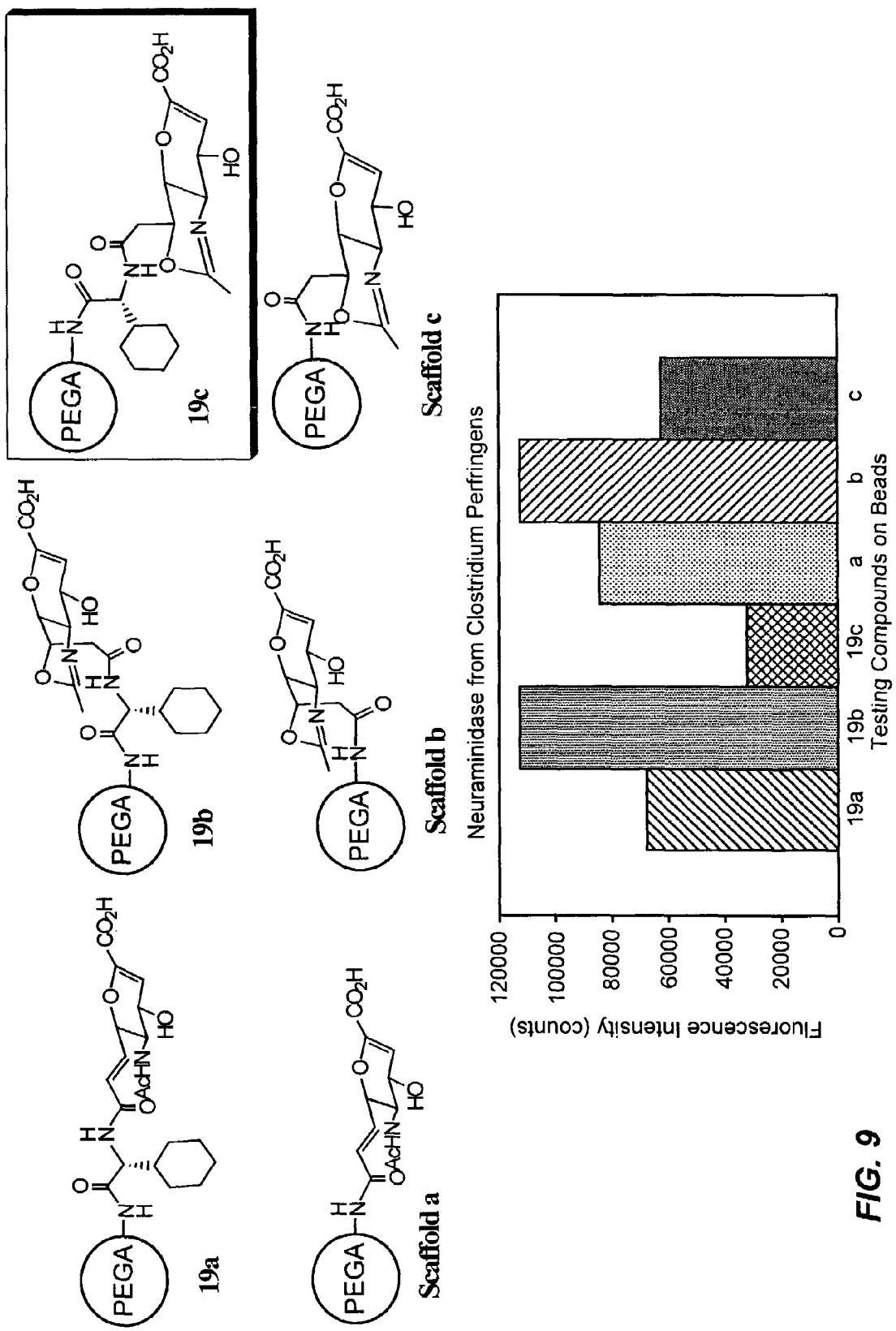
FIG. 9 illustrates the identification of a neuraminidase inhibitor, compound 19c.

Similarly, FIGS. 6 and 7 illustrate parallel synthetic approaches to libraries using functionalized DANA and ZANAMIVIR™ cores, respectively. Each support can be coupled to a plurality of different cores.

The components in solution or the functionalized resins can then be incubated with enzyme in a suitable buffer solution. The fluorescence intensity was measured using a fluorescence plate reader after a sufficient incubation period. One-bead-one-ligand-one-substrate combinatorial libraries may be used in a high-throughput screening method for identifying the test ligands as enzyme inhibitors. In another aspect of the invention, one-bead-multiple ligand-multiple substrate combinatorial libraries may also be made and used in a HTS method as outline above.

These complexes and methods are also suitable for enzymes that have multiple substrates. Thus in another aspect of the present invention, the detectable label may be quenched when it is brought into proximity of a quencher conjugated with the substrate. If the substrate is cleaved by the enzyme, the quencher will diffuse away from the detectable label and the detectable label will show a detectable change, for example, fluorescence. If the substrate is ligated by the enzyme, the quencher will be brought in proximity of the detectable label and the detectable label will show a detectable change, for example, quenching of fluorescence.

To illustrate this aspect of the present invention, the enzyme sialyltransferase will be used, however, the enzyme system used is not limiting to the present invention. For example as shown in Scheme 6, a "donor" substrate, e.g. CMP-Neu5Ac, which is conjugated with a detectable label (e.g. a fluorescent label), and a "acceptor" substrate is modified with a quencher (e.g. a fluorescent quencher). When the donor and acceptor substrates are incubated with their enzyme, the product will become non-detectable, e.g. non-fluorescent. The detectable change in the label, e.g. fluorescence to non-fluorescence, can be used to monitor the activity of the enzyme, e.g. sialyltransferase.

Examples of detectable label-quencher molecules include FRET pairs, and the like. Examples of FRET pairs include, but are not limited to, o-aminobenzamide (Abz)-3-nitrotyrosine [Tyr($NO_2$)], (see Meldal, M. et al. *Proc. Natl. Acad. Sci. USA.* 1994, 91, 3314-3318); Abz-ethylenediamine dinitrophenyl (EDDnp) (see Chagas, J. R. et al. *Anal. Biochem.* 1991, 192, 419-425; and Juliano L. et al. *Biochem. Biophys. Res. Commun.* 1990, 173, 647-652); and 5-[(2'-aminoethyl)amino]naphthalene sulphonic acid (EDANS)-4-[[4'-(dimethylamino)phenyl]azo]benzoic acid (DABCYL) (see Taliani, M. et al. *Lett. Pept. Sci.* 1997, 4, 101-106).

In one aspect of the present invention, the testing ligand is first incubated with enzyme, e.g. sialyltransferase, and then the donor and acceptor substrates are added to the mixture. In this aspect, the inhibitory activity can be analyzed based on the detectable change in the label, e.g. fluorescence.

In another aspect of the invention, one-bead-one-compound-one-acceptor libraries can be constructed. The library is then incubated with enzyme, e.g. sialyltransferase, in the presence of a donor substrate. If the test ligand on the bead does not inhibit the enzyme, the donor substrate will be transferred to acceptor substrate, and the bead will show no change in the detectable label, e.g. strong fluorescence. If the test ligand on bead is a potent inhibitor, it will block the transfer of the donor substrate to the acceptor substrate, and the detectable label will remain dark.

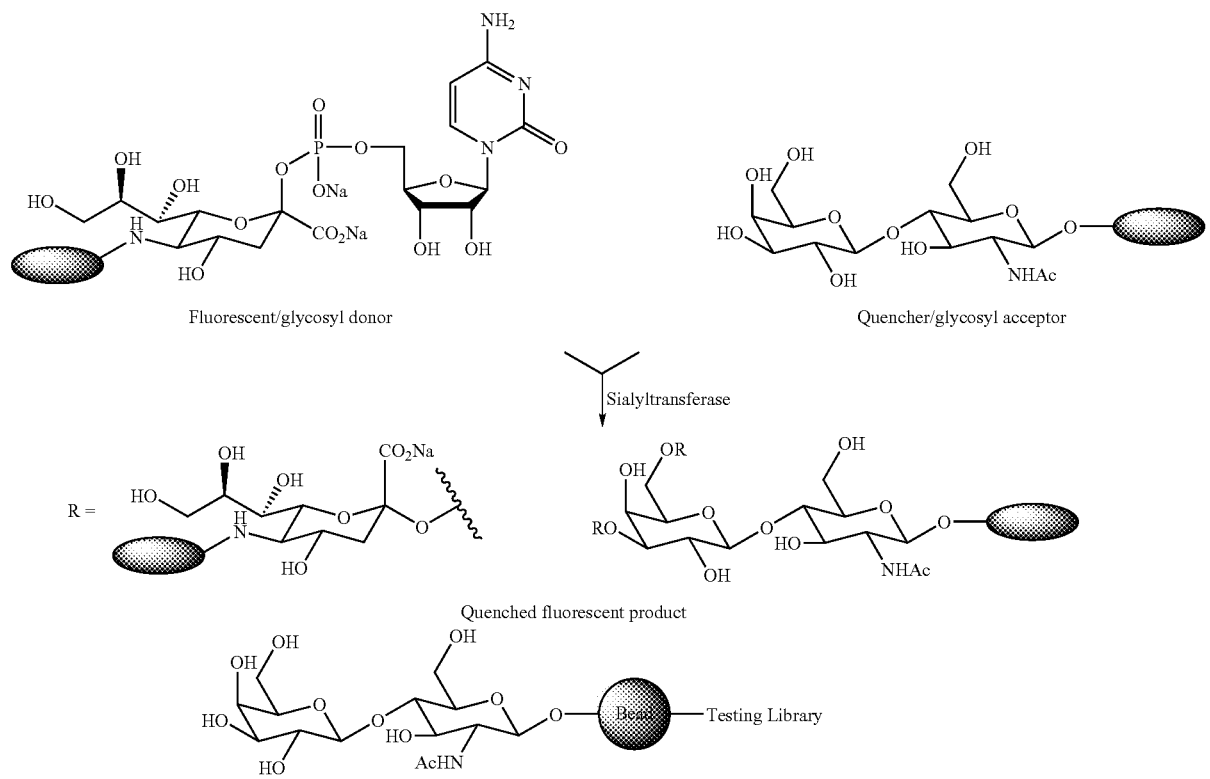

Scheme 6.
HTS of Sialyltransferase Inhibitors Both in Solution and on Solid-support -continued

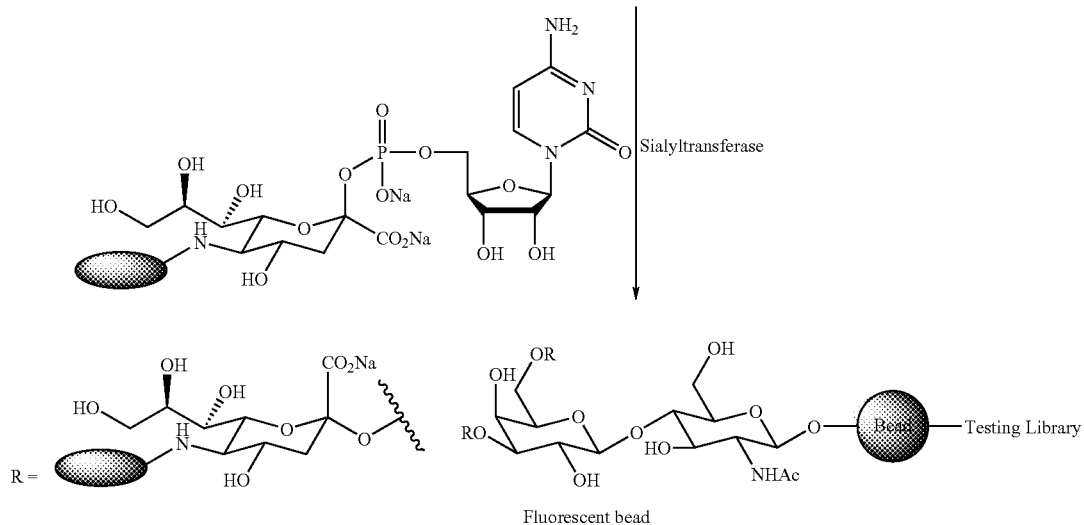

In another aspect of the invention, one-bead-one-compound-one-donor libraries can be constructed. The library is then incubated with enzyme, e.g. sialyltransferase, in the presence of a acceptor substrate. If the test ligand on the bead does not inhibit the enzyme, the donor substrate will be transferred to acceptor substrate, and the bead will show no change in the detectable label, e.g. strong fluorescence. If the test ligand on bead is a potent inhibitor, it will block the transfer of the donor substrate to the acceptor substrate, and the detectable label will remain dark.

Figure 14:
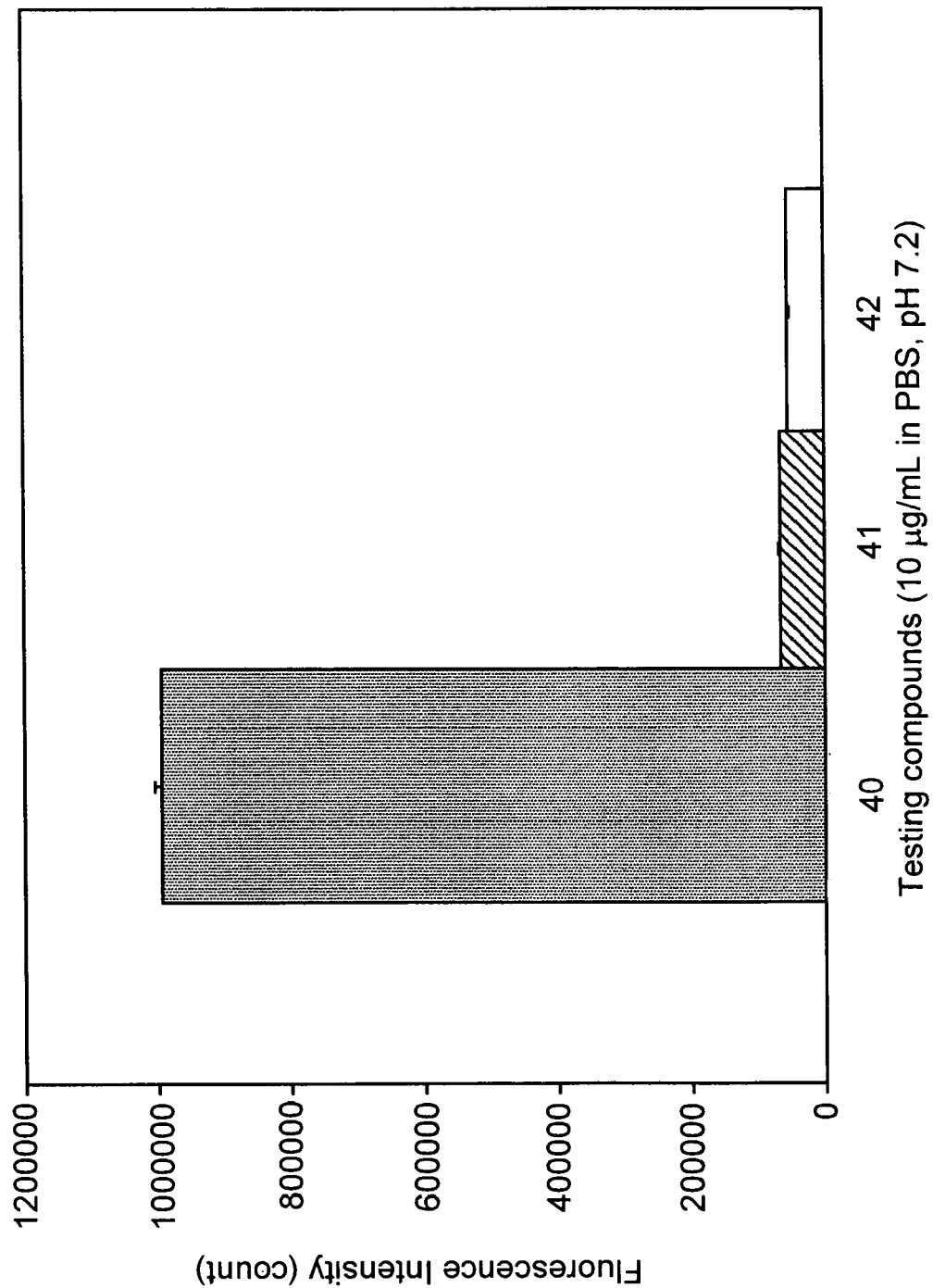
FIG. 14 illustrates the quenching efficiency of compound 41 and 42.

If FRET pairs are used as the detectable label, it is recognized that suitable FRET pairs may depend on the size and the tendency of the FRET pairs to interact with the particular enzyme, and the efficiency of energy transfer. For sialyltransferase, 7-hydroxycoumarin-4-acetic acid 40 conjugated with Tyr(NO$_2$) exhibits sufficient quenching of fluorescence. Likewise, as shown in FIG. 14, compounds 41 and 42 showed excellent fluorescence quench, the quenching efficiency being over 90%.

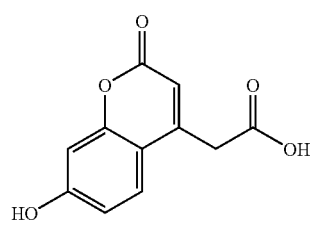

40

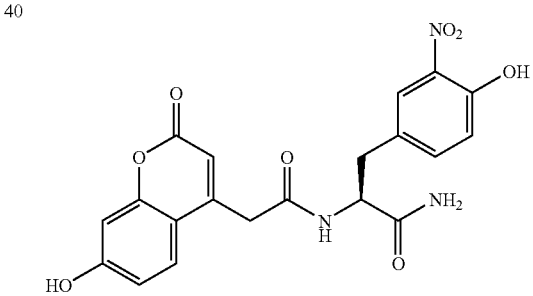

41

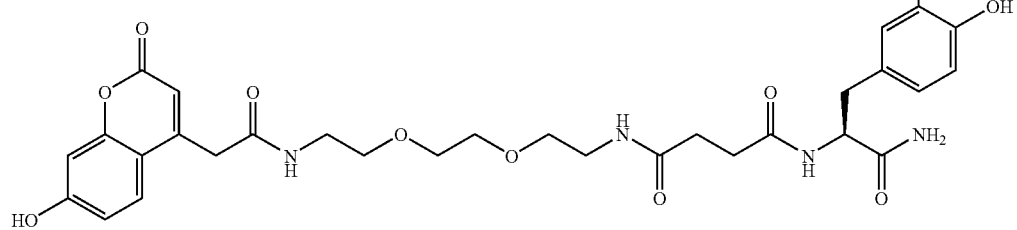

42

Synthesis of Detectable Label-Donor Substrate Conjugates

The synthesis of suitable detectable label-donor substrate conjugates for sialyltransferase is exemplified below in Scheme 7. To make the fluorescent donor, 2-deoxy-2-chloro-4,7,8,9-tetra-O-acetyl-N-acetylneuraminic acid 43 (see Marra, A. and Sinay, P. *Carbohydr. Res.* 1989, 190, 317-322) can be treated with 4-methoxybenzyl alcohol (PMBOH) in the presence of silver carbonate to give 49 (see Ikeda, K. et al. *Bioorg. Med. Chem. Lett.* 2002, 12, 2309-2311). The replacement of the N-acetyl group of 49 with a fluorescence label can give 50. Deprotection of 4-(para)-methoxybenzyl (PMB) group of 50 by 2,3-dichloro-5,6-dicyanobenzoquinone (DDQ) yields 51 (see Horita, K. et al. *Tetrahedron* 1986, 42, 3021-3028). Reaction of 51 with chlorodiethoxyphosphane in the presence of Hünig's base affords the β-phosphite, followed by reaction with N,O-acetyl-protected CMP derivative 52 (see Martin, T. J. et al. *Bioorg. Med. Chem.* 1994, 2, 1203-1208). gives the corresponding CMP-Neu5Ac analogue.

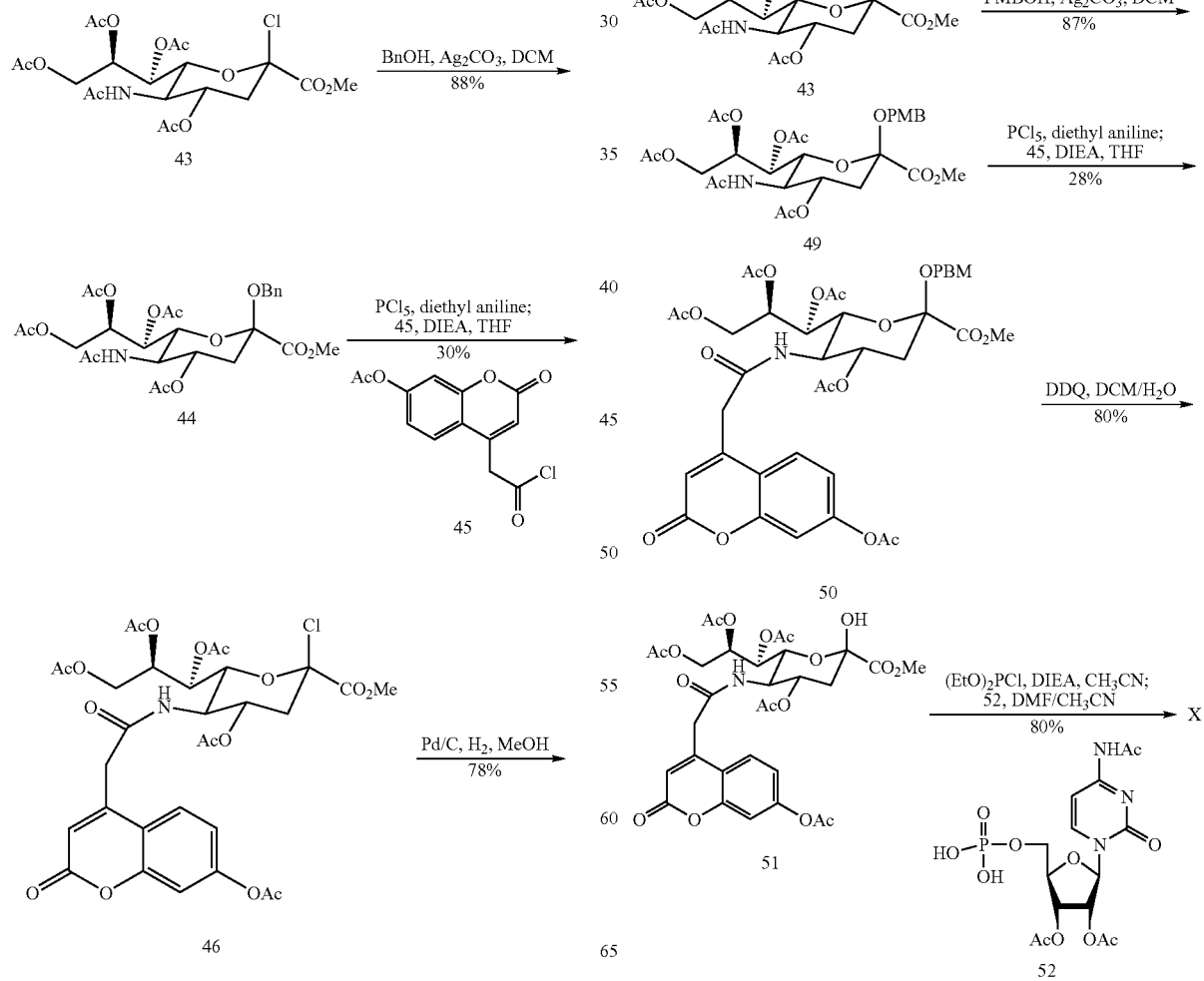

An alternative synthetic approach is illustrated in Scheme 8. The N-acetyl group of 49 can first be replaced by 9-fluorenylmethoxycarbonyl (Fmoc)-protected glycine to afford 53. After removal of the Fmoc protecting group, the immediate can be conjugated with compound 45 to give 54. Deprotection of PMB group of 54 by DDQ, and reaction of anomeric hydroxy group with chlorodiethoxyphosphane in the presence of Hünig's base, then conjugation of the β-phosphite with N,O-acetyl-protected CMP derivative 52 (see Martin, T. J. et al. Bioorg. Med. Chem. 1994, 2, 1203-1208), gives the corresponding CMP-Neu5Ac analogue. De-O-acetylation with sodium methoxide (NaOMe) in methanol, followed by removal of N-acetyl protecting group and methyl ester with NaOH in water yields the fluorescent CMP-Neu5Ac analogue 55.

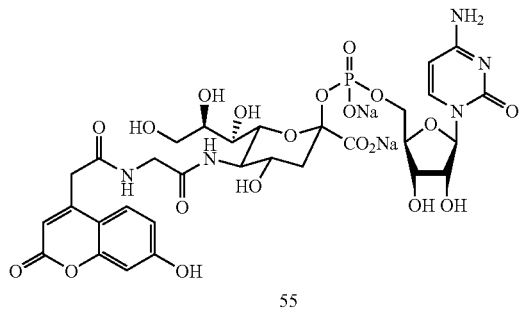

55

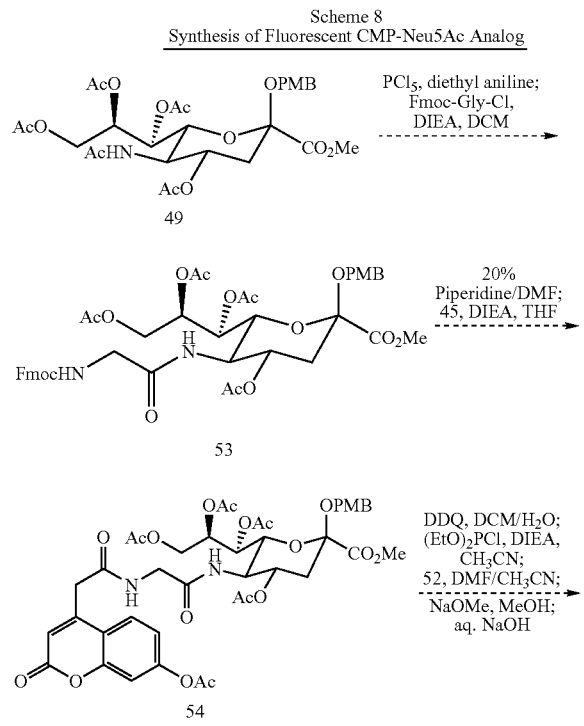

Scheme 8
Synthesis of Fluorescent CMP-Neu5Ac Analog

More diverse fluorescent CMP-Neu5Ac analogues can be made as shown in Scheme 9. The N-acetyl group of 44 can be removed by phosphorus pentachloride, (see Ikeda, K. et al. Chem. Pharm. Bull. 1991, 39, 1305-1309), followed by acylation with trifluoroacetylamino-acetyl chloride (see Nordlander, J. E. et al. J. Org. Chem. 1984, 49, 4107-4111), to give 56. Hydrogenolysis of 56 in the presence of Pd/C, and reaction of anomeric hydroxy group with chlorodiethoxyphosphane in the presence of Hünig's base, then conjugation of the β-phosphite with N,O-acetyl-protected CMP derivative 52 (see Martin, T. J. et al. Bioorg. Med. Chem. 1994, 2, 1203-1208), affords the corresponding CMP-Neu5Ac analogue 57 (see Dufner, G. et al. Eur. J. Org. Chem. 2000, 1467-1482) Removal of all protecting groups under the condition described above gives 58. Conjugation of 58 with fluoresceinyl isothiocyanate (FITC) in DMF and water at pH 8~9 affords 59 (see Brossmer, R. and Gross, H. J. Methods Enzymol. 1994, 247 B, 177-192). Reaction of 58 with 7-hydroxy-4-coumarinylacetic acid N-succinimidyl ester (see Demant, E. J. F. Biochimica et Biophysica Acta 1996, 1304, 43-55), in dimethylsulfoxide (DMSO) and water at pH 8~9 affords 55. Treatment of 58 with 7-amino-4-methyl-3-coumarinacetic acid N-succinimidyl ester (see Stefanova, H. I. et al. Biochem. 1993, 32, 356-62), in DMSO and water at pH 8~9 affords 55.

Scheme 9.
Synthesis of Diverse Fluorescent CMP-Neu5Ac Analogues

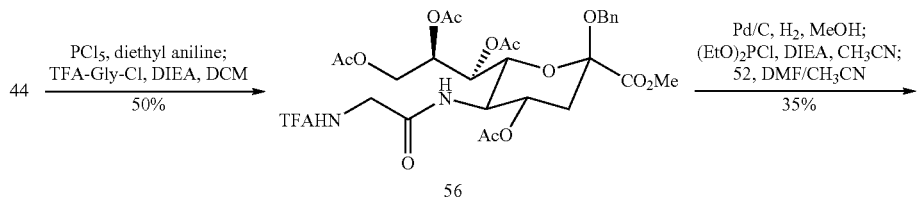

-continued

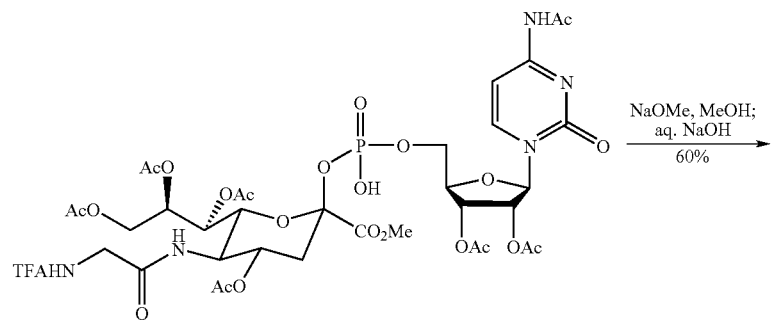

57

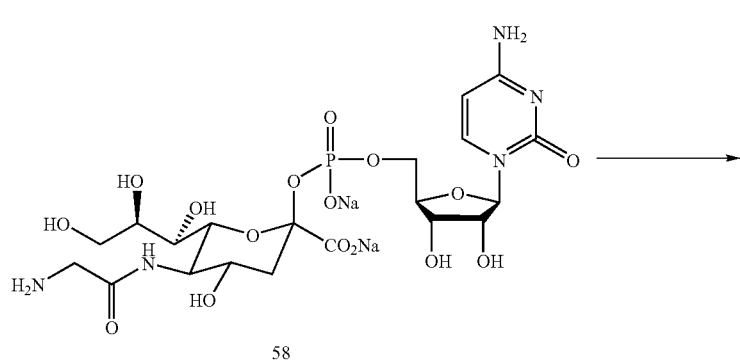

58

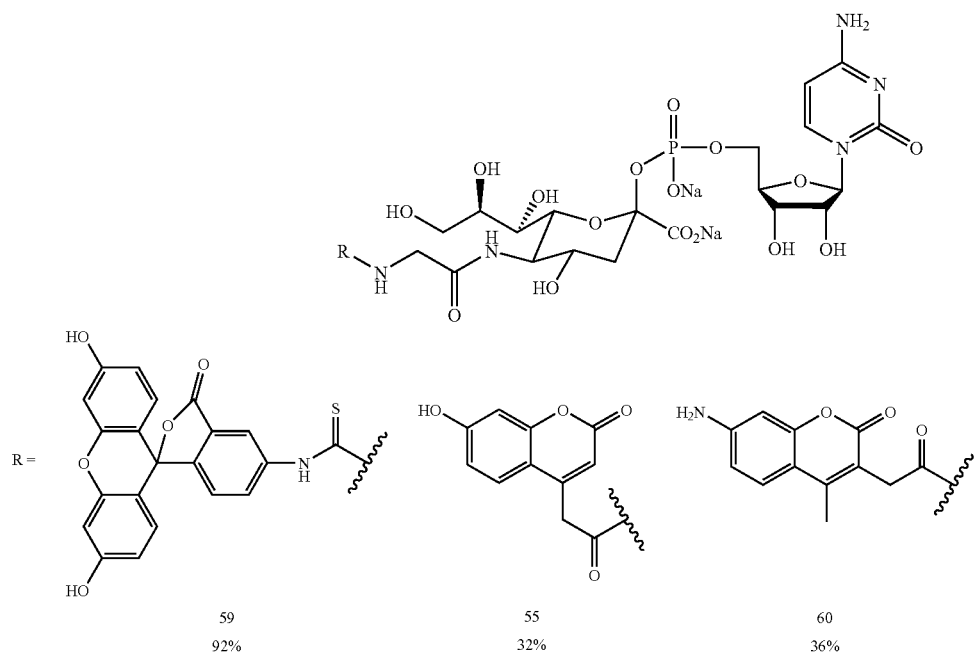

Synthesis of Quencher-Acceptor Substrate Conjugates

Examples of the synthesis the suitable quencher-acceptor substrate conjugates for sialyltransferases is shown in Scheme 10. Glycosylation of lactose peracetate 61 (SIGMA) with 2-azidoethanol (see Chernyak, A. Y. et al. *Carbohydr. Res.* 1992, 223, 303-309) in the presence of boron trifluoride etherate gives the β-glycoside 62 (see Sun, X. L. et al. *Biomacromolecules* 2002, 3, 1065-1070). Hydrogenation of 62 in the presence of palladium on carbon (Pd/C) affords 63 (see Hatanaka, Y. et al. *Bioorg. Med. Chem. Lett.* 1995, 5, 2859-2862). Reaction of 63 with $N^{\alpha}$-Fmoc-3-nitro-L-tyrosine pentafluorophenyl ester [Fmoc-Tyr($NO_2$)-OPfP], followed by removal of the Fmoc protecting group with 20% piperidine in DMF and the acetate protecting groups with NaOMe in methanol (MeOH) gives 64.

Scheme 10
Synthesis of a Lactose-Derived Acceptor

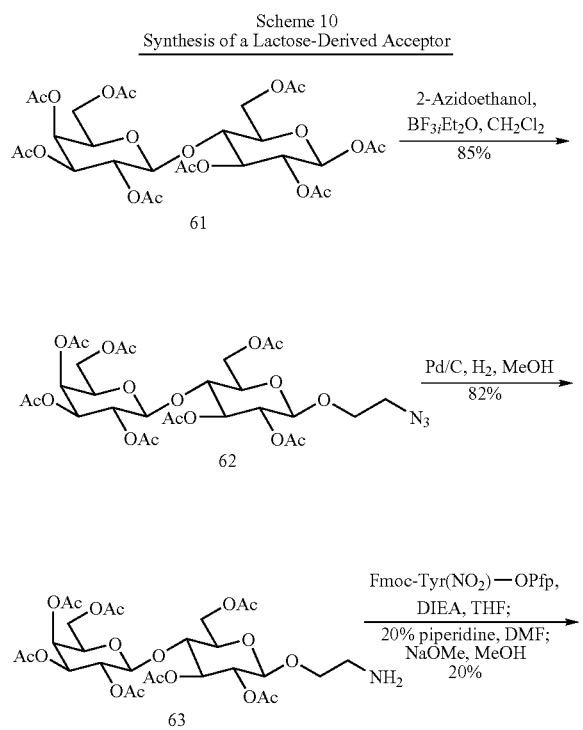

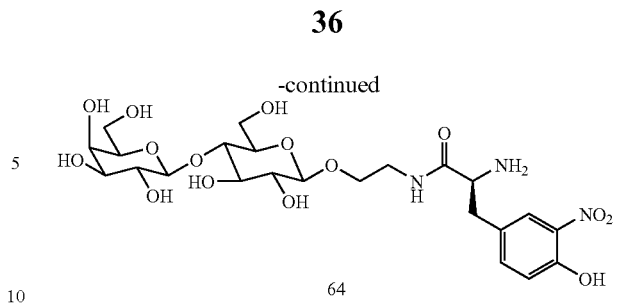

N-Acetyllactosamine is an acceptor substrate for both α2,3- and α2,6-sialyltransferases (see Limberg, G. et al. *Liebigs Ann.* 1996, 1773-1784) and the synthesis of N-acetyllactosamine derived acceptor is shown in Scheme 11. Treatment of N-acetyllactosamine peracetate 65 (SIGMA) with acetyl chloride and small amount of concentrated hydrogen chloride (HCl) gives halide 66 (see Kaifu, R. and Osawa, T. *Carbohydr. Res.* 1976, 52, 179-185). Reaction of halide 66 with 2-azidoethanol (see Chernyak, A. Y. et al. *Carbohydr. Res.* 1992, 223, 303-309) in the presence of mercuric cyanide affords 67 (see Mohan, H. et al. *Synlett* 2003, 9, 1255-1256; Rana, S. S. and Matta, K. L. *Carbohydr. Res.* 1983, 113, C18-C21). Treatment of 67 with catalytic NaOMe in MeOH gives 68 (see Blixt, O. et al. *J. Org. Chem.* 2001, 66, 2442-2448). Reduction of 67 with hydrogen in the presence of Pd/C, then conjugation with Fmoc-Tyr(NO₂)-OPfp (pentafluorophenyl ester), followed by removal of the Fmoc protecting group with 20% piperidine in DMF and the acetate protecting groups with NaOMe in MeOH gives 69.

Scheme 11
Synthesis of a N-Acetyllactosamine-Derived Acceptor

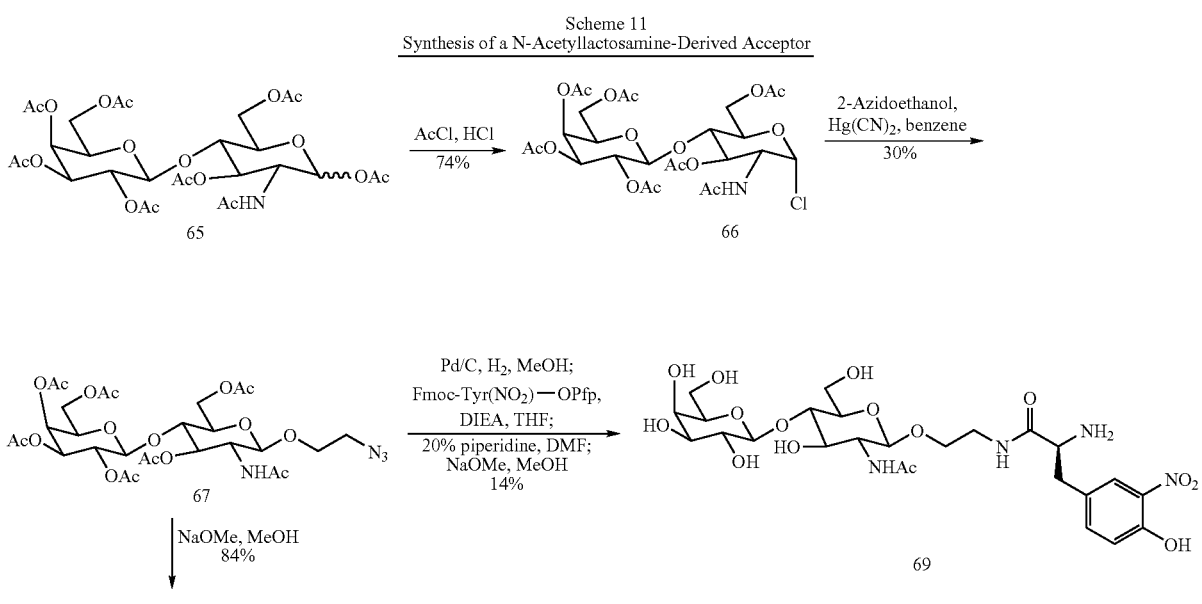

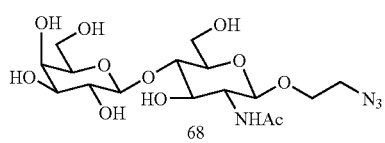

The synthesis of 2-acetamido-2-deoxy-3-O-β-D-galactopyranosyl-β-D-glucose derived acceptor is shown in Scheme 12. Treatment of 70 (ACROS) with benzaldehyde dimethylacetal in the presence of a catalytic amount of p-toluenesulfonic acid gives 71 (see Jeanloz, R. W. et al. *Carbohydr. Res.* 1968, 6, 184-196). Glycosylation of 71 with 2,3,4,6-tetra-O-acetyl-α-D-galactopyranosyl bromide in 1:1 nitrobenzene/benzene in the presence of mercuric cyanide affords 72 (see Matta, K. L. and Barlow, J. J. *Carbohydr. Res.* 1975, 43, 299-304). Hydrogenolysis of 72 in the presence of Pd/C gives 73.

*Soc.* 2000, 122, 11270-11271), which does not interfere with fluorescence of donor. After removal of Fmoc protecting group using 20% piperidine in DMF, the resin was then conjugated with a mixture of $N^\alpha$-Fmoc/acyl (Ac)-glycine (1:10) to decrease the loading. After deprotection of Fmoc protecting group again, the resin can be reacted with succinic anhydride. The carboxylic acid on bead can then be conjugated with acceptor 63, followed by removal of acetate group using NaOMe in MeOH to give 74. To immobilize the acceptor 68 on bead, the resin can be coupled with a mixture of 4-pentynoic acid/$N^\alpha$-Ac-glycine (1:10). The terminal alkyne on the

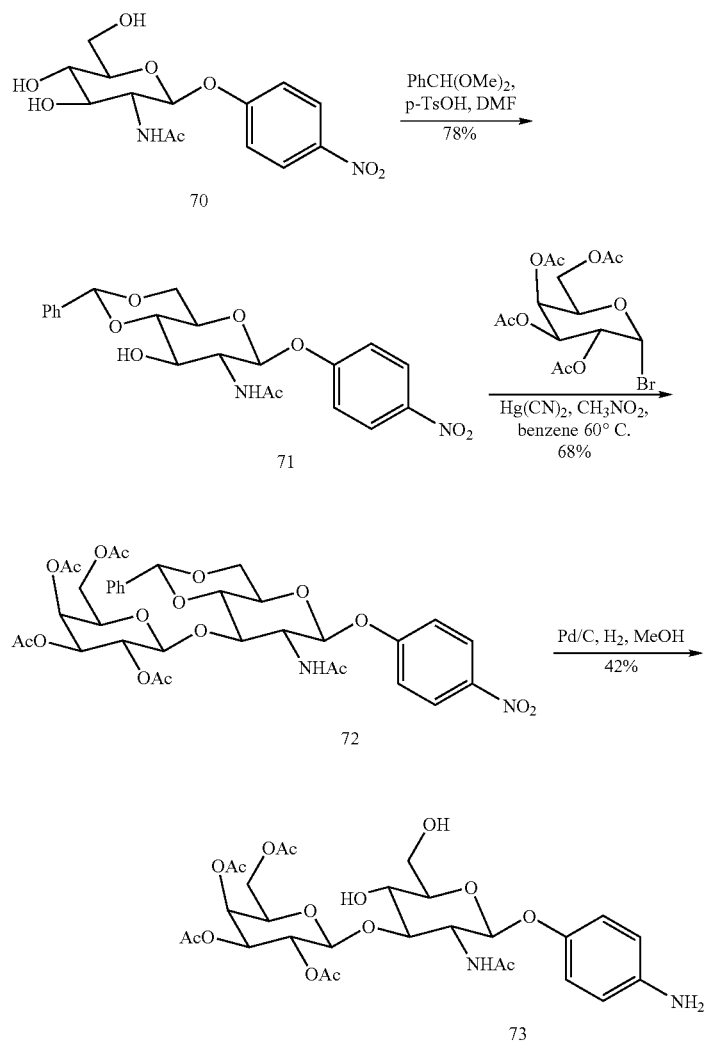

Either the acceptor or the donor may be immobilized on the solid support. The solid support used is not limiting. For example, acryloylated bis(2-aminopropyl)polyethylene glycol/dimethyl acrylamide copolymer (PL-PEGA) resin can be used as solid support, which can be swelled in both organic and aqueous media. The PEGA resin was first coupled with Fmoc-4-$NO_2$-phenylalanine to reduce the auto-fluorescence of the beads (Scheme 13), (see Harris, R. F. et al. *J. Am. Chem.* bead can be subjected to 1,3-dipolar cycloaddition with acceptor 68 in the presence of copper sulfate ($CuSO_4$) and sodium ascorbate to give 75 (see Rostovsev, V. V. et al. *Angew. Chem. Int. Ed.* 2002, 41, 2596-2599). To synthesize the acceptor 76, the carboxylic acid on bead may first be converted to an acid chloride using oxalyl chloride, then conjugated with acceptor 73, followed removal of acetate group with NaOMe in MeOH to yield 76.

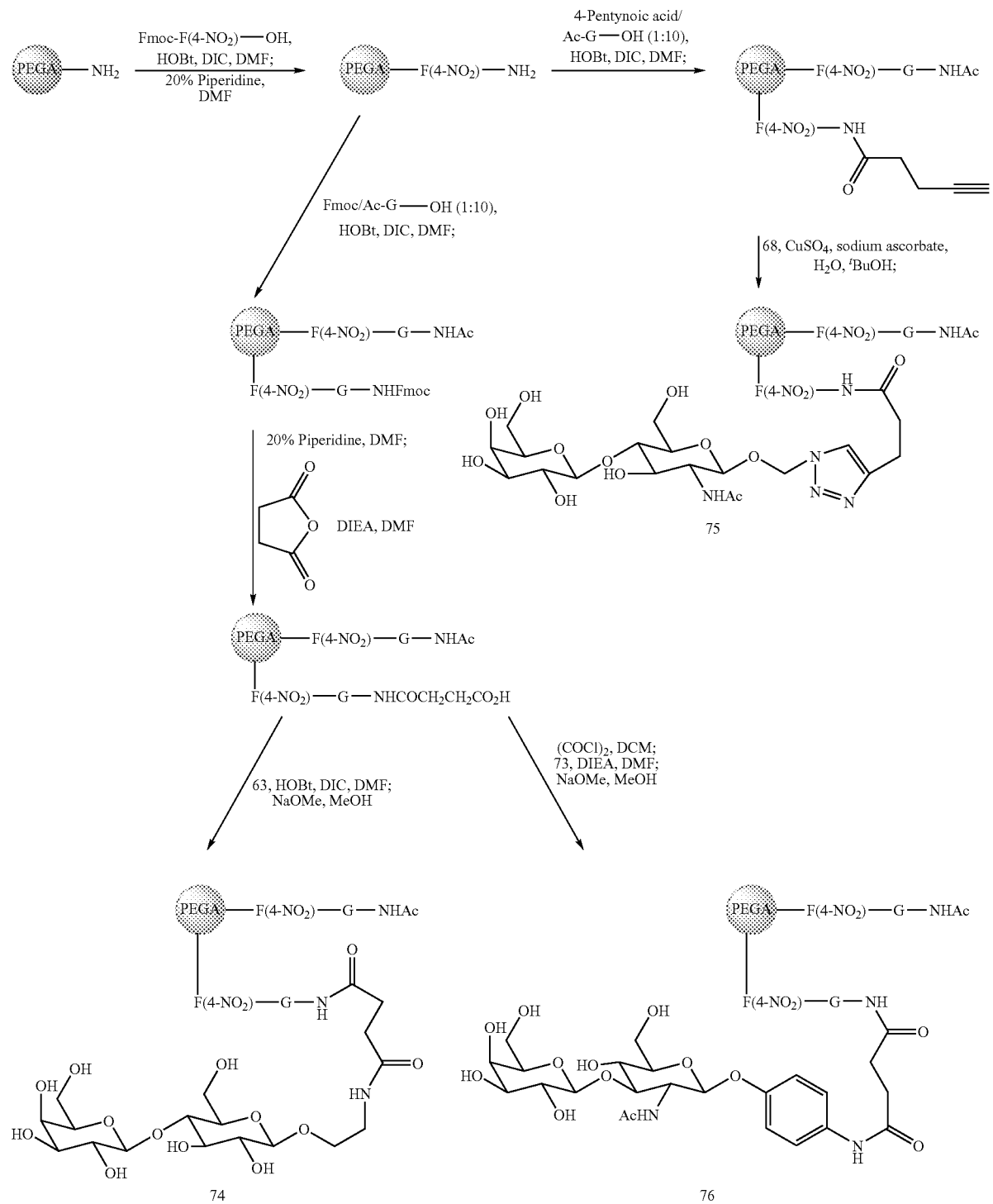

Scheme 13
Synthesis of Acceptors 74, 75, and 76 on Bead

Synthesis of Test Ligands

Known sialyltransferase inhibitors, WWWWWG-NH$_2$ and WWWWNG-NH$_2$, (see Lee, K. Y. et al. *J. Biol. Chem.* 2002, 277, 49341-49351) are illustrated as model inhibitors to illustrate one-bead-one-acceptor-one-inhibitor libraries of this aspect of the present invention. As mentioned, the solid support used is not critical. Examples of suitable supports include, but are not limited to, PL-PEGA resin. As shown in Scheme 14, the resin was first coupled with Fmoc-4-NO$_2$- phenylaniline to reduce auto-fluorescence of the beads (see Harris, R. F. et al. *J. Am. Chem. Soc.* 2000, 122, 11270-11271). After removal of the Fmoc protecting group, the resin can be conjugated with a mixture of 4-pentynoic acid and Fmoc-trytophan (1:10). Then, the peptides WWWNG-NH$_2$ and WWWWG-NH$_2$ can be constructed on the solid support using standard peptide synthesis. The terminal alkyne on bead can be involved in a 1,3-dipolar cycloaddition with acceptor 68 in the presence of CuSO$_4$ and sodium ascorbate to give 77 and 78, individually (see Rostovsev, V. V. et al. *Angew. Chem. Int. Ed.* 2002, 41, 2596-2599).

to about 2 mM and more preferably about 0.2 mM. Suitable concentrations of donor range from about 0.001 mM to about 10 mM preferably about 0.01 mM to about 1 mM and more preferably about 0.1 mM. Suitable concentrations of enzyme range from about 0.002 mU to about 20 mU preferably about 0.02 mU to about 2 mU and more preferably about 0.2 mU. Suitable concentrations of inhibitor range from about 20 μM to about 300 μM. In a typical assay, the inhibitor is first incubated with enzyme in buffer for about 30 min. Then, the donor and acceptor are added and the reaction mixture is incubated for 1 h. As a blank control, enzyme can be incu-

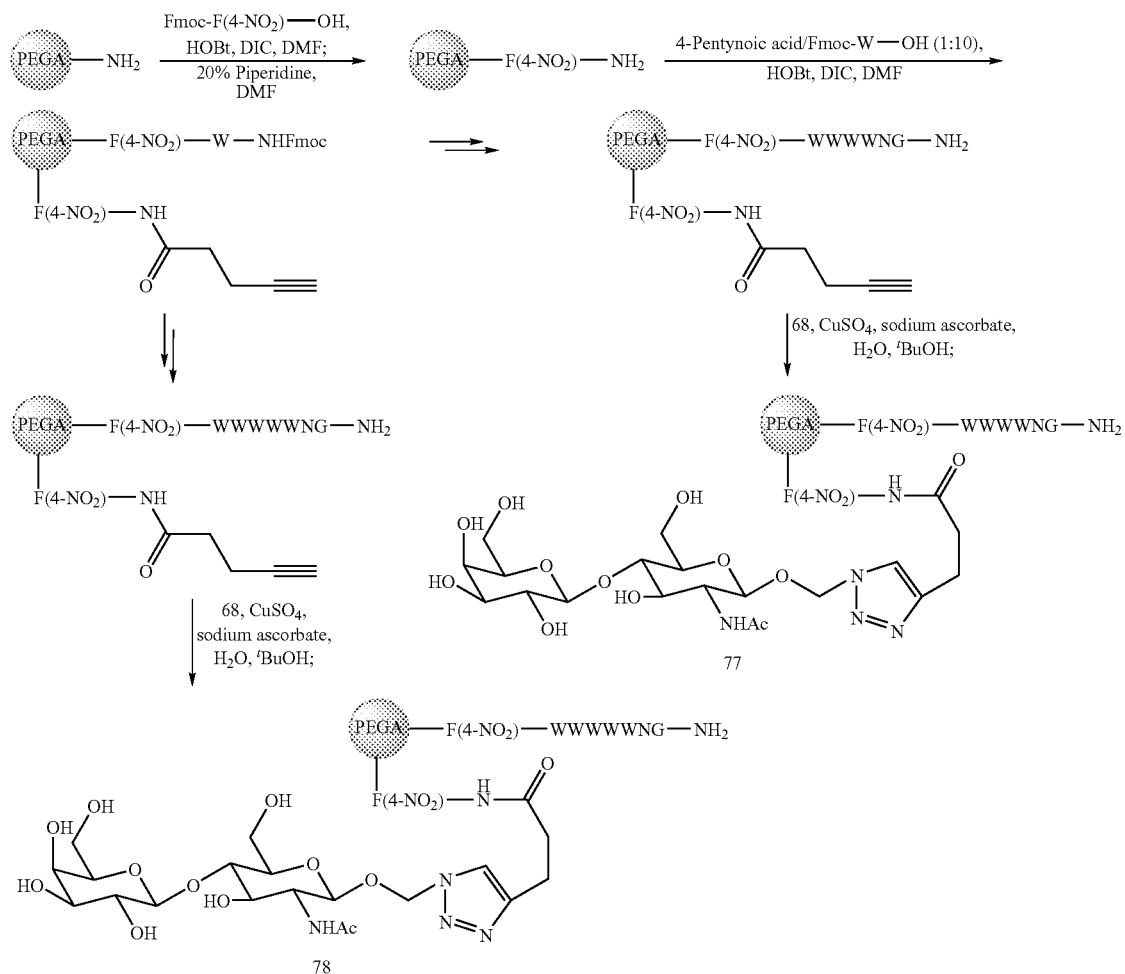

To test the activity and quenching efficiency of acceptors and donors, the acceptors and donors can be incubated in the presence of the enzyme, e.g. sialyltransferase. As a control, the a donor or acceptor can be incubated with the enzyme in the absence of the other.

Enzymatic assays may be carried out in a suitable buffer as is known in the art. For example, for sialyltransferases a buffer containing 62.5 mM sodium cacodylate (pH=6.0), 1 mg/mL bovine serum albumin (BSA), and 0.5% Triton X 100 may be used (see Gross, H. J. et al. *Anal. Biochem.* 1990, 186, 127-134) Suitable concentrations of acceptor range from about 0.002 mM to about 20 mM preferably about 0.02 mM bated with the donor and acceptor without inhibitor. After rinsing any solid support with water, the change in the detectable label, e.g. fluorescent intensity, can be measured using a suitable device. For fluorescent labels, a fluorescence plate reader may be used. Using this competitive assay, the inhibitory activity of enzyme inhibitors can be screened.

The invention will now be described in greater detail by way of specific examples. The following examples are put forth so as to provide those of ordinary skill in the art with a complete disclosure and description of how make a detectable substrate of the present invention and to use such a substrate to identify enzyme inhibitors, and are not intended to limit the scope of what the inventors regard as their invention.

EXAMPLES

Reagents and General Procedures. All chemicals were used as supplied without further purification. Solvents (MeOH 99.8%, CH$_2$Cl$_2$ 99.8%, CH$_3$CN 99.8%, DMF 99.8%) were purchased in anhydrous SURE/SEAL™ bottles from Aldrich, used without further purification, and stored under argon. Bacterial neuraminidases (*Clostridium perfringens, Salmonella typhimurium, Vibrio cholerae*) were purchased from Sigma. Sialyltransferases were purchased from Calbiochem. BSA, (Fraction V), Triton X 100, and CMP-Neu5Ac were purchase from Sigma. PL-PEGA resin (0.4 mmol/g, 150-300 μm) was purchased from Polymer Laboratories. Dowex 50WX8 (200 mesh) acidic resin was purchased from Aldrich, washed copiously with methanol, and used without further purification. NaOMe/MeOH (0.5 M) was purchased from Aldrich. Glass-backed EM Science thin layer chromatography (TLC) plates (silica gel 60 with a 254 nm fluorescent indicator) were purchased from VWR International, cut into 2 cm×5 cm portions, used without further manipulation, and stored over dessicant. Developed TLC plates were visualized under a short wave UV lamp, stained with a cerium-molybdate solution and charred. Column chromatography was conducted using flash silica gel (32-63 μm) available from Scientific Adsorbents and solvents purchased from EM Science. NMR experiments (1-D and 2-D) were conducted on Bruker DRX500 MHz spectrometers at 298 K. Reverse phase-high performance liquid chromatography (RP-HPLC) preparative separations were carried out on Vydac C18 column (10×250 mm). Solvents: (A) water (H$_2$O) and (B) acetonitrile (CH$_3$CN) with UV detection at 220 and 254 nm. Fluorescence intensity was measured using PerkinElmer fluorescence plate reader.

Example 1

Synthesis of Detectable Label-Substrate Conjugate 8-Allyl-4-methylumbelliferyl-4,7,8,9-tetra-O-acetyl-α-D-N-acetyl-neuraminic amide-bead conjugate 7-Allyloxy-4-methylcoumarin (2)

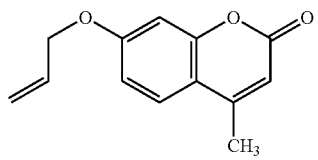

3-Bromo-1-propene (2.95 mL, 34.06 mmol) was added dropwise under argon to a stirred mixture of 7-hydroxy-4-methylcoumarin 1 (2.0 g, 11.35 mmol) and anhydrous potassium carbonate (K$_2$CO$_3$) (2.35 g, 17.03 mmol) in acetone (50 mL). The resulting mixture was then refluxed for 4 h, after which it was allowed to cool, and the K$_2$CO$_3$ filtered off and washed with fresh acetone. The solvent was removed in vacuo and the residue was crystallized from methanol to afford 2 as white-cream crystals (2.36 g, 96%). TLC (hexane/ethyl acetate, 1:3): R$_f$=0.63. mp 110° C. $^1$H NMR (CDCl$_3$, 500 MHz) δ 2.39 (s, 3H, CH$_3$), 4.60 (d, J=5.0 Hz, 2H, CH$_2$), 5.33 (d, J=10.5 Hz, 1H), 5.44 (d, J=17.5 Hz, 1H), 6.05 (m, 1H), 6.12 (s, 1H), 6.80 (s, 1H), 6.87 (dd, J=1.5, 9.0 Hz, 1H), 7.49 (d, J=9.0 Hz, 1H). $^{13}$C NMR (CDCl$_3$, 125 MHz) δ 18.70, 69.29, 101.84, 112.05, 112.79, 113.75, 118.51, 125.64, 132.31, 152.61, 152.26, 161.26, 161.65. ESIMS calcd for C$_{13}$H$_{13}$O$_3$ [M+H]$^+$ 217.1, found 217.1.

8-Allyl-7-hydroxyl-4-methyl-2H-chromen-2-one (3)

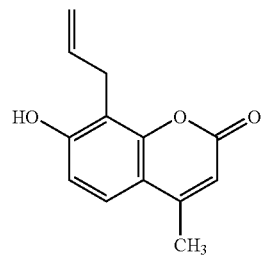

7-Allyloxy-4-methylcoumarin 2 (1.0 g, 4.62 mmol) was dissolved in N,N-diethylaniline (8 mL) in a sealed vial and heated to 250° C. for 25 min under microwave. The reaction mixture was then cooled, during which some of the product precipitated. Hexane (10 mL) was added in order to precipitate out the remaining product. The precipitate was filtered, washed with hexane, and dried under vacuum to yield 3 as a pale-yellow solid (0.88 g, 88%). TLC (hexane/ethyl acetate, 1:3): R$_f$=0.5. mp 204° C. $^1$H NMR (CDCl$_3$/CD$_3$OD, 500 MHz) δ 2.43 (s, 3H, CH$_3$), 3.57 (d, J=6.0 Hz, 2H, CH$_2$), 4.95 (d, J=10.0 Hz, 1H), 5.04 (d, J=17.0 Hz, 1H), 5.97 (m, 1H), 6.10 (s, 1H), 6.86 (d, J=9.0 Hz, 1H), 7.46 (d, J=9.0 Hz, 1H). $^{13}$C NMR (CDCl$_3$/CD$_3$OD, 125 MHz) δ 18.85, 27.66, 110.78, 113.20, 113.73, 114.93, 115.41, 124.38, 136.16, 153.89, 155.88, 160.18, 163.92. ESIMS calcd for C$_{13}$H$_{13}$O$_3$ [M+H]$^+$ 217.1. Found 217.2.

8-Allyl-4-methylumbelliferyl-4,7,8,9-tetra-O-acetyl-α-D-N-acetyl-neuraminic acid methyl ester (4)

2-Deoxy-2-chloro-4,7,8,9-tetra-O-acetyl-α-D-N-acetyl-neuraminic acid methyl ester (0.68 g, 1.32 mmol) was dissolved in a mixture of 3 (0.32 g, 1.46 mmol), Ag$_2$CO$_3$ (0.37 g, 1.32 mmol) and activated molecular sieves (1.20 g) in anhydrous acetonitrile (20 mL). The mixture was stirred under argon at room temperature in the dark overnight, filtered, and evaporated. The residue was purified by column chromatography (ethyl acetate) to give 4 as a white solid (0.71 g, 78%). TLC (ethyl acetate): R$_f$=0.19. mp 107° C. [α]$_D^{26}$+27.0° (c 0.5, CHCl$_3$). $^1$H NMR (CDCl$_3$, 500 MHz) δ 1.93, 2.05, 2.12, 2.20 (4s, 15H, 4-OAc, 1-NAc), 2.32 (m, 1H, H-3a), 2.41 (s, 3H, CH$_3$), 2.76 (dd, J=4.5, 13.0 Hz, 1H, H-3e), 3.61 (m, 5H, CO$_2$CH$_3$, CH$_2$), 4.13 (m, 2H, H-5, H-9a), 4.28 (m, 1H, H-9b), 4.57 (m, 1H, H-6), 5.00 (m, 2H, H-4, CH$_2$=CH), 5.08 (d, J=17.0 Hz, 1H, CH$_2$=CH), 5.29 (d, J=10.0 Hz, 1H, NH), 5.39 (m, 2H, H-7, H-8), 5.93 (m, 1H, CH$_2$=CH), 6.19 (s, 1H, C=CH), 7.17 (d, J=9.0 Hz, 1H), 7.41 (d, J=9.0 Hz, 1H). $^{13}$C NMR (CDCl$_3$, 125 MHz) δ 19.00, 20.92, 20.99, 21.22, 23.41, 27.71, 38.79, 49.71, 53.27, 62.17, 67.28, 68.61, 68.73, 73.66, 100.23, 113.38, 114.27, 115.93, 116.22, 118.67, 123.46, 135.01, 152.47, 152.78, 154.94, 161.13, 168.23, 170.16, 170.31, 170.42, 170.71, 171.06. FABHRMS calcd for C$_{33}$H$_{39}$NO$_{15}$Na [M+Na]$^+$ 712.2212. Found 712.2222.

Example 2

Synthesis of Detectable Label-Substrate Conjugate 4-Methyl acetate-umbelliferyl-4, 7, 8, 9-tetra-O-acetyl-α-D-N-acetyl-neuraminic amide-bead Conjugate 4-Bromomethyl-7-hydroxycoumarin (7)

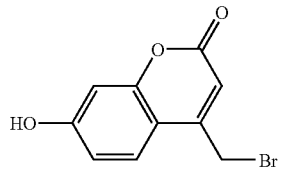

NaOMe (5.38 mL, 0.5 M, 2.69 mmol) was added slowly under argon to a stirred solution of 4-bromomethyl-7-acetoxycoumarin 6 (0.80 g, 2.69 mmol) in dry methanol (15 mL). The resulting mixture was stirred for 0.5 h. The methanolic solution was acidified with Dowex 50WX8 (H+) resin, filtered, washed with methanol, and evaporated to afford 7 as a white solid (0.68 g, 100%). TLC (hexane/ethyl acetate, 1:3): $R_f$=0.58. mp 207° C. $^1$H NMR (CD$_3$OD, 500 MHz) δ 4.66 (s, 2H, CH$_2$), 6.36 (s, 1H, C=C$\underline{H}$), 6.73 (d, J=1.5 Hz, 1H), 6.84 (dd, J=1.5, 8.5 Hz, 1H), 7.71 (d, J=8.5 Hz, 1H). $^{13}$C NMR (CD$_3$OD, 125 MHz) δ 27.58, 103.80, 111.17, 112.32, 114.37, 127.54, 153.61, 157.23, 163.24, 163.28. ESIMS calcd for C$_{10}$H$_8$BrO$_3$ [M+H]$^+$ 255.0. Found 255.1.

4-Bromomethylumbelliferyl-4,7,8,9-tetra-O-acetyl-α-D-N-acetyl-neuraminic acid methyl ester (8)

2-Deoxy-2-chloro-4,7,8,9-tetra-O-acetyl-α-D-N-acetyl-neuraminic acid methyl ester (0.55 g, 1.06 mmol) was dissolved in a mixture of 7 (0.30 g, 1.18 mmol), Ag$_2$CO$_3$ (0.29 g, 1.06 mmol) and activated molecular sieves (1.0 g) in anhydrous acetonitrile (20 mL). The mixture was stirred under argon at room temperature in the dark overnight, filtered, and evaporated. The residue was purified by column chromatography (ethyl acetate) to give 8 as a white solid (0.63 g, 82%). TLC (ethyl acetate): $R_f$=0.23. mp 117° C. $[\alpha]_D^{26}$+29.7° (c 0.6, CHCl$_3$). $^1$H NMR (CDCl$_3$, 500 MHz) δ 1.93, 2.05, 2.15, 2.16 (4s, 15H, 4-OAc, 1-NAc), 2.27 (m, 1H, H-3a), 2.74 (dd, J=4.5, 13.0 Hz, 1H, H-3e), 3.72 (s, 3H, CO$_2$CH$_3$), 4.12 (m, 2H, H-5, H-9a), 4.30 (m, 1H, H-9b), 4.49 (s, 2H, CH$_2$Br), 4.54 (m, 1H, H-6), 5.00 (m, 1H, H-4), 5.36 (m, 2H, H-7, H-8), 5.64 (d, J=10.0 Hz, 1H, NH), 6.45 (s, 1H, C=C$\underline{H}$), 7.07 (d, J=1.5 Hz, 1H), 7.10 (dd, J=1.5, 8.5 Hz, 1H), 7.65 (d, J=8.5 Hz, 1H). $^{13}$C NMR (CDCl$_3$, 125 MHz) δ 14.30, 20.85, 20.93, 21.08, 21.13, 23.27, 26.82, 38.24, 49.44, 53.40, 60.51, 62.24, 67.52, 68.55, 69.26, 73.92, 99.97, 108.12, 113.44, 114.64, 116.12, 125.75, 149.95, 155.09, 157.10, 160.46, 168.09, 170.17, 170.22, 170.43, 170.73, 170.92. FABHRMS calcd for C$_{30}$H$_{34}$NO$_{15}$BrNa [M+Na]$^+$ 750.1004. Found 750.1007.

Conjugating of 8 on Resin (9)

PL-PEGA resin (20 mg, 0.4 mmol/g, 150-300 μm) was swelled in DMF overnight. Compound 8 (18 mg, 24 μmol) and 20 μL DIEA were added to the resin. The resin was shaken for 8 h, and washed with DMF (5×3 mL), MeOH (5×3 mL), CH$_2$Cl$_2$ (5×3 mL).

Deprotection of 9 on Beads (10)

The resin 9 (20 mg, 0.4 mmol/g, 150-300 μm) was suspended in 1 mL anhydrous MeOH. NaOMe (100 μL, 0.5M) was added and the resin was shaken for 30 min and washed with MeOH. Aqueous NaOH (500 μL, 0.1 M) and MeOH (500 μL) were then added, and the resin was shaken for another 30 min, then washed with water (5×3 mL). A portion of beads was incubated with neuraminidase to confirm the conjugation.

Example 3

Synthesis of Detectable Label-Substrate Conjugate 4-Sodium acetate-umbelliferyl-α-D-N-acetyl-neuraminic amide-bead Conjugate 4-Methyl acetate-umbelliferyl-4,7,8,9-tetra-O-acetyl-α-D-N-acetyl-neuraminic acid methyl ester (13)

2-Deoxy-2-chloro-4,7,8,9-tetra-O-acetyl-α-D-N-acetyl-neuraminic acid methyl ester (1.10 g, 2.12 mmol) was dissolved in a mixture of 12 (see Zhu, Q. et al. *Organic Lett*. 2003, 5, 1257-1260). (0.54 g, 2.33 mmol), Ag$_2$CO$_3$ (0.58 g, 2.12 mmol) and activated molecular sieves (1.8 g) in anhydrous acetonitrile (30 mL). The mixture was stirred under argon at room temperature in the dark for 24 h, filtered, and evaporated. The residue was purified by column chromatography (ethyl acetate) to give 13 as pale yellow solid (0.66 g, 44%). TLC (ethyl acetate): $R_f$=0.18. mp 105° C. $[\alpha]_D^{26}$+25.6° (c 0.5, CHCl$_3$). $^1$H NMR (CDCl$_3$, 500 MHz) δ 1.92, 2.04, 2.14 (3s, 15H, 4-OAc, 1-NAc), 2.25 (m, 1H, H-3a), 2.72 (dd, J=4.5, 13.0 Hz, 1H, H-3e), 3.70 (s, 3H, CO$_2$CH$_3$), 3.74 (s, 3H, CO$_2$CH$_3$), 4.10 (m, 4H, H-5, H-9a, CH$_2$), 4.29 (m, 1H, H-9b), 4.51 (m, 1H, H-6), 5.00 (m, 1H, H-4), 5.37 (m, 3H, H-7, H-8, NH), 6.29 (s, 1H, C=C$\underline{H}$), 7.04 (m, 2H), 7.49 (d, J=9.0 Hz, 1H). $^{13}$C NMR (CDCl$_3$, 125 MHz) δ 20.86, 20.95, 21.11, 23.34, 37.92, 38.24, 49.60, 52.84, 53.45, 62.18, 67.46, 68.51, 69.19, 73.84, 99.96, 108.02, 115.15, 115.51, 116.13, 125.78, 147.83, 154.79, 156.92, 160.54, 168.06, 169.20, 170.22, 170.53, 170.79, 170.99. ESIMS calcd for C$_{32}$H$_{37}$O$_{17}$NNa [M+Na]$^+$ 730.2. Found 730.0.

4-Acetic acid umbelliferyl-α-D-N-acetyl-neuraminic acid disodium salt (14)

NaOMe (0.1 mL, 0.5 M, 0.05 mmol) was added slowly under argon to a stirred solution of 13 (200 mg, 0.28 mmol) in dry methanol (10 mL). The resulting mixture was stirred for 0.5 h. The methanolic solution was acidified with Dowex 50WX8 (H$^+$) resin, filtered, washed with methanol, and evaporated to dryness. The residue was dissolved in water (5 mL) and NaOH (5.9 mL, 0.1 M, 0.59 mmol) was added. The mixture was stirred for 1 h at room temperature, and freeze-dried to give a yellow solid, which was purified by RP-HPLC (H$_2$O/CH$_3$CN=90/10~70/30) to afford 14 as a white solid (100 mg, 64%). Decompose at 170° C. $[\alpha]_D^{24}$+45.3° (c 0.7, H$_2$O). $^1$H NMR (D$_2$O, 500 MHz) δ 2.08 (m, 4H, NAc, H-3a), 2.89 (dd, J=4.0, 12.5 Hz, 1H, H-3e), 3.66 (m, 2H), 3.88 (m, 6H), 4.13 (m, 1H), 6.37 (s, 1H, C=C<u>H</u>), 7.23 (m, 2H), 7.71 (d, J=8.5 Hz, 1H). $^{13}$C NMR (D$_2$O/CD$_3$OD, 125 MHz) δ 22.86, 42.25, 53.39, 64.0, 68.91, 69.72, 72.85, 74.91, 103.83, 109.33, 113.82, 116.55, 119.0, 127.05, 154.89, 155.05, 159.05, 164.76, 173.09, 175.87. ESIMS calcd for C$_{22}$H$_{24}$O$_{13}$NNa$_2$ [M+H]$^+$ 556.1. Found 556.1.

Conjugating of 14 on Beads (15)

PL-PEGA resin (40 mg, 0.4 mmol/g, 150-300 μm) was swelled in DMF overnight. Compound 14 (27 mg, 48 μmol), HOBt (48 μL, 1.0 M) and DIC (8 μL) were added to the resin. The resin was shaken for 3 h (monitored by Kaiser test), and washed with DMF (5×3 mL), CH$_2$Cl$_2$ (5×3 mL), MeOH (5×3 mL), H$_2$O (5×3 mL).

Example 4

Synthesis of Detectable Label-Substrate Conjugate 3-Allyloxy-6-[methyl(5-acetamido-4,7,8,9-tetra-O-acetyl-3,5-dideoxy-α-D-glycero-D-galacto-2-nonulopyranosyl)onate]xanthene-9-spiro-1'-isobenzofuran-3'-one 2-[3-Oxo-6-(2-propenyloxy)-3H-xanthen-9-yl]-benzoic acid 2-propenyl ester (17)

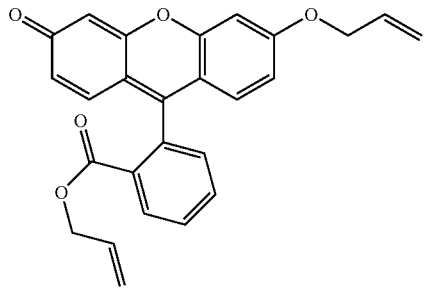

3-Bromo-1-propene (0.78 mL, 9.0 mmol) was added dropwise under argon to a stirred mixture of fluorescein 16 (1.0 g, 3.0 mmol) and K$_2$CO$_3$ (1.24 g, 9.0 mmol) in dry DMF (20 mL). The resulting mixture was stirred for 6 h at 65° C. The mixture was concentrated, diluted with ethyl acetate, washed with 10% NaHCO$_3$, brine, dried with anhydrous Na$_2$SO$_4$, and evaporated. The residue was purified by column chromatography (ethyl acetate/hexane=1:1) to give 17 as a brown solid (0.94 g, 76%). $^1$H NMR (CDCl$_3$, 500 MHz) δ 4.47 (m, 2H, CH$_2$), 4.65 (m, 2H, CH$_2$), 5.09 (s, 1H, CH), 5.11 (d, J=5.0 Hz, 1H, CH), 5.36 (d, J=11.0 Hz, 1H, CH), 5.46 (d, J=17.0 Hz, 1H, CH), 5.59 (m, 1H, CH), 6.06 (m, 1H, CH), 6.45 (s, 1H), 6.54 (d, J=9.5 Hz, 1H), 6.76 (d, J=8.5 Hz, 1H), 6.88 (m, 2H), 6.95 (s, 1H), 7.32 (d, J=7.5 Hz, 1H), 7.68 (t, J=7.5 Hz, 1H), 7.74 (t, J=7.5 Hz, 1H), 8.26 (d, J=7.5 Hz, 1H). $^{13}$C NMR (CDCl$_3$, 125 MHz) δ 66.23, 69.65, 101.37, 105.99, 113.97, 115.19, 117.98, 118.93, 119.38, 129.09, 129.86, 130.18, 130.41, 130.70, 130.70, 130.80, 131.15, 132.09, 132.85, 134.60, 150.12, 154.40, 159.12, 163.17, 165.21, 185.90. ESIMS calcd for C$_{26}$H$_{20}$O$_5$Na [M+Na]$^+$ 435.1. Found 435.2.

3'-Hydroxy-6'-(2-propenyloxy)-spiro[isobenzofuran-1(3H), 9'-[9H]xanthen]-3-one (18)

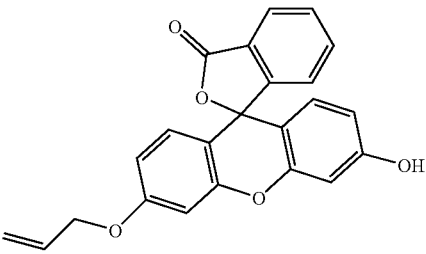

NaOH (20 mL, 1.0 M, 20.0 mmol) was added to a solution of 17 (0.40 g, 0.97 mmol) in methanol (60 mL). The resulting mixture was stirred for 2 h at room temperature. The mixture was concentrated, diluted with ethyl acetate, washed with 10% NaHCO$_3$, brine, dried with anhydrous Na$_2$SO$_4$, and evaporated. The residue was purified by column chromatography (ethyl acetate/hexane=1:1) to give 18 as a yellow solid (0.23 g, 65%). TLC (ethyl acetate/hexane, 3:1): R$_f$=0.6. mp 204° C. $^1$H NMR (CDCl$_3$/CD$_3$OD, 500 MHz) δ 4.58 (d, J=5.0 Hz, 2H, CH$_2$), 5.32 (d, J=10.5 Hz, 1H, CH), 5.43 (d, J=17.5 Hz, 1H, CH), 6.04 (m, 1H, CH), 6.62 (m, 4H), 6.74 (s, 1H), 6.80 (s, 1H), 7.20 (d, J=7.5 Hz, 1H), 7.65 (t, J=7.5 Hz, 1H), 7.71 (t, J=7.5 Hz, 1H), 8.01 (d, J=7.5 Hz, 1H). $^{13}$C NMR (CDCl$_3$/CD$_3$OD, 125 MHz) δ 69.00, 101.71, 102.73, 109.90, 111.21, 111.94, 112.42, 117.89, 124.04, 124.80, 126.69, 128.88, 128.95, 129.72, 132.51, 135.16, 152.56, 160.28, 170.26. ESIMS calcd for C$_{23}$H$_{17}$O$_5$ [M+H]$^+$ 373.1. Found 373.2.

3-Allyloxy-6-[methyl(5-acetamido-4,7,8,9-tetra-O-acetyl-3,5-dideoxy-α-D-glycero-D-galacto-2-nonulopyranosyl)onate]xanthene-9-spiro-1'-isobenzofuran-3'-one (19)

2-Deoxy-2-chloro-4,7,8,9-tetra-O-acetyl-α-D-N-acetylneuraminic acid methyl ester (140 mg, 0.27 mmol) was dissolved in a mixture of 18 (112 mg, 0.30 mmol), Ag$_2$CO$_3$ (76 mg, 0.27 mmol) and activated molecular sieves (400 mg) in anhydrous acetonitrile (10 mL). The mixture was stirred under argon at room temperature in the dark for overnight, filtered, and evaporated. The residue was purified by column chromatography (ethyl acetate) to give 19 as a pale-yellow solid (96 mg, 42%). TLC (ethyl acetate): R$_f$=0.26. mp 115° C. [α]$_D^{26}$+12.9° (c 0.8, CHCl$_3$). $^1$H NMR (CDCl$_3$, 500 MHz) δ 1.91, 2.03, 2.03, 2.05, 2.14 (5s, 15H, 4-OAc, 1-NAc), 2.22 (m, 1H, H-3a), 2.67 (dd, J=4.5, 13.0 Hz, 1H, H-3e), 3.70 (s, 3H, CO$_2$CH$_3$), 4.06 (m, 1H, H-5), 4.16 (m, 1H, H-9a), 4.30 (m, 1H, H-9b), 4.56 (m, 3H, H-6, C<u>H</u>$_2$—CH=CH$_2$), 4.99 (m, 1H, H-4), 5.33 (m, 3H, H-7, H-8, CH$_2$—CH=C<u>H</u>$_2$), 5.42 (d, J=17.0 Hz, 1H, CH$_2$—CH=C<u>H</u>$_2$), 5.50 (broad s, 1H, NH), 6.00 (m, 1H, CH$_2$—C<u>H</u>=CH$_2$), 6.70 (m, 5H), 7.03 (d, J=4.0 Hz, 1H), 7.19 (dd, J=7.5, 11.5 Hz, 1H), 7.62 (t, J=7.5 Hz, 1H), 7.66 (t, J=7.5 Hz, 1H), 8.02 (d, J=7.5 Hz, 1H). $^{13}$C NMR (CDCl$_3$, 125 MHz) δ 20.89, 21.00, 23.27, 37.69, 46.69, 49.45, 53.44, 62.19, 67.24, 67.79, 68.77, 69.26, 73.88, 99.98, 100.20, 102.02, 107.78, 108.13, 108.45, 111.38, 112.45, 114.77, 114.99, 118.32, 124.18, 125.23, 126.72, 128.81, 129.95, 132.73, 135.27, 152.09, 152.42, 153.26, 155.28, 160.53, 168.01, 168.24, 169.65, 170.22, 170.36, 170.47, 171.04. FABHRMS calcd for $C_{43}H_{43}NO_{17}Na$ [M+Na]$^+$ 868.2423. Found 868.2406.

Example 5

Synthesis of Detectable Label-Substrate Conjugate 3-Sodium acetate-6-(5-acetamido-3,5-dideoxy-α-D-glycero-D-galacto-2-nonulopyranosylonic acid sodium salt) xanthene-9-spiro-1'-isobenzofuran-3'-one 2-(6-Hydroxy-3-oxo-3H-xanthen-9-yl)-benzoic acid 2-propenyl ester (21)

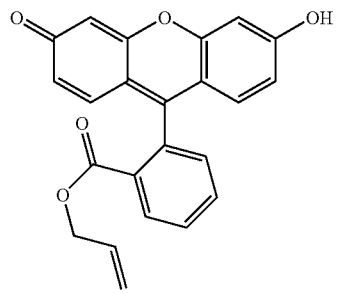

Bromo-1-propene (0.78 mL, 9.0 mmol) was added dropwise under argon to a stirred mixture of fluorescein 16 (3.0 g, 9.0 mmol) and $K_2CO_3$ (1.24 g, 9.0 mmol) in dry DMF (40 mL). The resulting mixture was stirred for 4 h at 65° C. The mixture was concentrated, diluted with ethyl acetate, washed with 10% $NaHCO_3$, brine, dried with anhydrous $Na_2SO_4$, and evaporated. The residue was purified by column chromatography (ethyl acetate/hexane=2:1) to give 21 as a brown solid (0.70 g, 21%). $^1$H NMR (CDCl$_3$, 500 MHz) δ 4.42 (d, J=6.0 Hz, 2H, CH$_2$), 5.06 (m, 2H, 2CH), 5.53 (m, 1H, CH), 6.81 (m, 2H), 6.88 (m, 2H), 6.98 (m, 2H), 7.32 (d, J=7.5 Hz, 1H), 7.68 (t, J=7.5 Hz, 1H), 7.74 (t, J=7.5 Hz, 1H), 8.26 (d, J=7.5 Hz, 1H). $^{13}$C NMR (CDCl$_3$, 125 MHz) δ 66.26, 103.90, 115.01, 119.49, 122.30, 130.02, 130.51, 130.65, 131.00, 131.38, 132.77, 134.48, 155.89, 158.06, 165.08, 175.84. ESIMS calcd for $C_{23}H_{17}O_5$ [M+H]$^+$ 373.1. Found 373.2.

(6'-hydroxy-3-oxospiro[isobenzofuran-1(3H), 9'-[9H]xanthen]-3'-yl)oxy-acetic acid methyl ester (22)

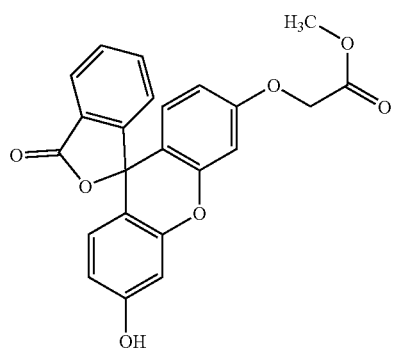

Methyl bromoacetate (0.25 mL, 2.65 mmol) was added dropwise to a stirred mixture of 21 (0.33 g, 0.89 mmol) and $K_2CO_3$ (0.36 g, 2.65 mmol) in dry DMF (20 mL) under argon. The resulting mixture was stirred for 4 h at 90° C. The mixture was concentrated, diluted with ethyl acetate, washed with 10% $NaHCO_3$, brine, dried with anhydrous $Na_2SO_4$, and evaporated. The residue was dissolved in dry DCM (25 mL). Tetrakis(triphenylphosphine) palladium(0) (58 mg, 0.05 mmol) and phenylsilane (1.1 mL, 8.90 mmol) were added. The mixture was stirred for 2 h at room temperature and concentrated. The residue was purified by column chromatography (ethyl acetate/hexane=1:1) to give 22 as a yellow solid (0.22 g, 62%). TLC (ethyl acetate/hexane, 3:1): $R_f$=0.5. mp 236° C. $^1$H NMR (CDCl$_3$/CD$_3$OD, 500 MHz) δ 3.76 (s, 3H, CO$_2$CH$_3$), 4.69 (s, 2H, CH$_2$), 6.68 (m, 6H), 7.19 (d, J=7.5 Hz, 1H), 7.66 (t, J=7.5 Hz, 1H), 7.71 (t, J=7.5 Hz, 1H), 8.01 (d, J=7.5 Hz, 1H). $^{13}$C NMR (CDCl$_3$/CD$_3$OD, 125 MHz) δ 52.33, 65.18, 101.86, 102.77, 109.84, 111.55, 112.37, 112.52, 124.05, 124.87, 126.67, 129.00, 129.24, 129.80, 135.21, 152.47, 152.56, 152.94, 159.34, 169.21, 170.15, 171.36, 172.03. ESIMS calcd for $C_{23}H_{17}O_7$ [M+H]$^+$ 405.1. Found 405.2.

3-Methyl acetate-6-[methyl(5-acetamido-4,7,8,9-tetra-O-acetyl-3,5-dideoxy-α-D-glycero-D-galacto-2-nonulopyranosyl)onate]xanthene-9-spiro-1'-isobenzofuran-3'-one (23)

2-Deoxy-2-chloro-4,7,8,9-tetra-O-acetyl-α-D-N-acetylneuraminic acid methyl ester (170 mg, 0.33 mmol) was dissolved in a mixture of 22 (148 mg, 0.37 mmol), $Ag_2CO_3$ (92 mg, 0.33 mmol) and activated molecular sieves (400 mg) in anhydrous acetonitrile (10 mL). The mixture was stirred under argon at room temperature in the dark overnight, filtered, and evaporated. The residue was purified by column chromatography (ethyl acetate) to give 23 as a pale-yellow solid (115 mg, 40%). $[\alpha]_D^{26}$+12.7° (c 1.1, CHCl$_3$). $^1$H NMR (CDCl$_3$, 500 MHz) δ 1.91, 1.96, 1.99, 2.03, 2.10 (5s, 15H, 4-OAc, 1-NAc), 2.21 (m, 1H, H-3a), 2.67 (dd, J=4.5, 13.0 Hz, 1H, H-3e), 3.73 (s, 3H, CO$_2$CH$_3$), 3.82 (s, 3H, CO$_2$CH$_3$), 4.11 (m, 2H, H-5, H-9a), 4.32 (m, 1H, H-9b), 4.46 (m, 1H, H-6), 4.66 (s, 2H, CH$_2$), 4.99 (m, 1H, H-4), 5.27 (d, J=9.5 Hz, 1H, NH), 5.34 (m, 2H, H-7, H-8), 6.70 (m, 5H), 7.03 (m, 1H), 7.19 (dd, J=7.5, 11.5 Hz, 1H), 7.62 (t, J=7.5 Hz, 1H), 7.68 (t, J=7.5 Hz, 1H), 8.02 (d, J=7.5 Hz, 1H). $^{13}$C NMR (CDCl$_3$, 125 MHz) δ 20.92, 21.01, 21.16, 23.41, 37.88, 49.68, 52.59, 53.47, 62.17, 65.51, 67.71, 68.75, 69.71, 73.87, 99.97, 100.20, 102.20, 107.86, 108.38, 112.03, 112.57, 114.68, 116.26, 124.23, 125.28, 126.74, 129.22, 129.49, 130.02, 135.02, 152.01, 152.47, 153.17, 155.39, 159.61, 168.22, 168.95, 169.47, 170.10, 170.17, 170.42, 170.74, 171.04. ESIMS calcd for $C_{43}H_{43}NO_{19}Na$ [M+Na]$^+$ 900.2. Found 900.1.

3-Sodium acetate-6-(5-acetamido-3,5-dideoxy-α-D-glycero-D-galacto-2-nonulopyranosylonic acid sodium salt) xanthene-9-spiro-1'-isobenzofuran-3'-one (24)

NaOMe (0.1 mL, 0.5 M, 0.05 mmol) was added slowly under argon to a stirred solution of 23 (52 mg, 0.059 mmol) in dry methanol (5 mL). The resulting mixture was stirred for 0.5 h. The methanolic solution was acidified with Dowex 50 (H$^+$) resin, filtered, washed with methanol, and evaporated to dryness. The residue was dissolved in water (5 mL), and NaOH (1.29 mL, 0.1 M, 0.129 mmol) was added. The mixture was stirred for 1 h at room temperature, and freeze-dried to give a yellow solid, which was purified by RP-HPLC (H₂O/CH₃CN=90:10~70:30) to afford 24 as pale-yellow solid (28 mg, 67%). Decompose at 150° C. $[\alpha]_D^{24}$+17.5° (c 0.3, H₂O). ¹H NMR (CD₃OD, 500 MHz) δ 1.88 (m, 1H, H-3a), 2.02 (s, 3H, NAc), 2.97 (m, 1H, H-3e), 3.54-3.90 (m, 7H, H-4, 5, 6, 7, 8, 9a, 9b), 4.51 (s, 2H, CH₂), 6.66 (m, 3H), 6.86 (m, 1H), 6.99 (m, 1H), 7.20 (m, 2H), 7.71 (t, J=7.5 Hz, 1H), 7.78 (t, J=7.5 Hz, 1H), 8.01 (d, J=7.5 Hz, 1H). ¹³C NMR (CD₃OD, 125 MHz) δ 22.62, 42.89, 53.99, 64.48, 69.27, 70.27, 73.12, 75.27, 77.30, 85.06, 102.97, 110.01, 112.41, 113.20, 114.77, 118.45, 118.63, 125.27, 125.76, 127.78, 129.11, 129.83, 130.04, 131.18, 136.69, 153.06, 153.81, 154.48, 158.36, 161.92, 171.54, 175.53. ESIMS calcd for C₃₃H₂₉NO₁₅Na₃ [M+Na]⁺ 748.1. Found 748.1.

Conjugating of 24 to Resin (25)

PL-PEGA resin (20 mg, 0.4 mmol/g, 150-300 μm) was swelled in DMF overnight. Compound 24 (12 mg, 16 μmol), HOBt (24 μL, 1.0 M) and DIC (4 μL) were added to the resin. The resin was shaken for 4 h (monitored by Kaiser test), and washed with DMF (5×3 mL), CH₂Cl₂ (5×3 mL), MeOH (5×3 mL), H₂O (5×3 mL).

Example 6

Synthesis of Test Ligand 5-Acetamido-4-(tert-butyl-dimethyl-silanyloxy)-8,9-O-(1-methylethylidene)-2, 6-anhydro-3,5-dideoxy-D-glycero-D-galacto-Non-2-enonic acid methyl ester (27)

5-Acetamido-4-(tert-butyldimethylsilanyloxy)-8,9-O-(1-methylethylidene)-2,6-anhydro-3,5-dideoxy-D-glycero-D-galacto-non-2-enonic acid methyl ester (27)

2,2-Dimethoxypropane (0.45 mL, 3.67 mmol) was added slowly to a stirred solution of 26 (see Kirchner, E. et al. *J. Carbohydr. Chem.* 1988, 7, 453-86), (187 mg, 0.61 mmol) in dry acetone (10 mL) under argon. Toluenesulfonic acid (12 mg, 0.06 mmol) was added to the solution. The resulting mixture was stirred overnight at room temperature. The mixture was evaporated and dissolved in DMF (10 mL), TBSCl (110 mg, 0.73 mmol) and imidazole (42 mg, 0.61 mmol) was added. The solution was stirred under argon for 6 h at room temperature. The mixture was evaporated and extracted with ethyl acetate, and purified by column chromatography (ethyl acetate/hexane=2:1) to give 27 as a white solid (208 mg, 74%). TLC (ethyl acetate/hexane, 3:1): $R_f$=0.35. mp 245° C. ¹H NMR (CDCl₃, 500 MHz) δ 0.17 (s, 3H, CH₃), 0.19 (s, 3H, CH₃), 0.91 (s, 9H, 3CH₃), 1.37 (s, 3H, CH₃), 1.41 (s, 3H, CH₃), 2.04 (s, 3H, NAc), 3.60 (m, 1H), 3.81 (s, 3H, OCH₃), 4.07 (m, 2H), 4.16 (t, J=8.5 Hz, 1H), 4.24 (d, J=7.0 Hz, 1H), 4.34 (m, 2H), 4.48 (m, 1H, OH), 5.54 (d, J=7.5 Hz, 1H), 5.89 (d, J=3.5 Hz, 1H, NH). ¹³C NMR (CDCl₃, 125 MHz) δ -4.46, -4.27, 18.10, 23.36, 25.46, 25.77, 27.20, 51.70, 52.63, 66.26, 67.51, 72.12, 74.63, 76.70, 109.42, 109.92, 144.97, 162.75, 171.46. ESIMS calcd for C₂₁H₃₇NO₈SiNa [M+Na]⁺ 482.2. Found 482.3. Anal. Calc. for C₂₁H₃₇NO₈Si: C, 54.88; H, 8.11; N, 3.05. Found: C, 54.82; H, 8.19; N, 3.03.

5-Acetylamino-4-(tert-butyldimethylsilanyloxy)-6-[(2,2-dimethyl-[1,3]dioxolan-4-yl)-methoxycarbonylmethoxy-methyl]-5,6-dihydro-4H-pyran-2-carboxylic acid methyl ester (28)

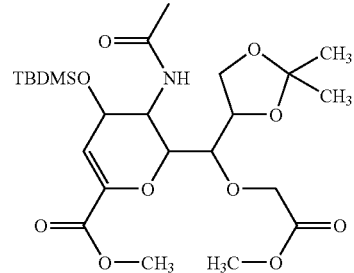

Sodium hydride (26 mg, 1.09 mmol) was added in portions to a stirred solution of 27 (250 mg, 0.54 mmol) and methyl bromoacetate (0.1 mL, 1.09 mmol) in dry DMF (10 mL). The resulting mixture was stirred overnight at room temperature. Then, the mixture was evaporated and extracted with ethyl acetate, and purified by column chromatography (ethyl acetate/hexane=2:1) to give 28 as a white solid (205 mg, 71%). ¹H NMR (CDCl₃, 500 MHz) δ 0.03 (s, 3H, CH₃), 0.05 (s, 3H, CH₃), 0.85 (s, 9H, 3CH₃), 1.27 (s, 3H, CH₃), 1.41 (s, 3H, CH₃), 1.91 (s, 3H, NAc), 3.49 (m, 1H, H-5), 3.70 (s, 3H, OCH₃), 3.71 (s, 3H, OCH₃), 4.07 (m, 2H), 4.17 (t, J=9.0 Hz, 1H), 4.26 (t, J=7.0 Hz, 1H), 4.36 (m, 1H), 4.57 (m, 1H), 4.66 (dd, J=2.0, 10.0 Hz, 1H, H-6), 5.23 (dd, J=2.0, 8.5 Hz, 1H, H-4), 5.78 (d, J=2.5 Hz, 1H, H-3), 7.02 (d, J=6.5 Hz, 1H, NH). ¹³C NMR (CDCl₃, 125 MHz) δ -4.75, -4.58, 18.04, 23.71, 24.63, 25.64, 25.81, 26.35, 51.99, 52.25, 54.0, 64.46, 64.62, 68.33, 76.07, 76.26, 78.81, 107.79, 113.61, 143.01, 162.60, 171.28, 172.39. ESIMS calcd for C₂₄H₄₁NO₁₀SiNa [M+Na]⁺ 554.3. Found 554.3. Anal. Calc. for C₂₄H₄₁NO₁₀Si: C, 54.22; H, 7.77; N, 2.63. Found: C, 54.14; H, 7.98; N, 2.61.

5-Acetylamino-4-(tert-butyldimethylsilanyloxy)-6-[carboxymethoxy-(2,2-dimethyl-[1,3]dioxolan-4-yl)-methyl]-5,6-dihydro-4H-pyran-2-carboxylic acid (29)

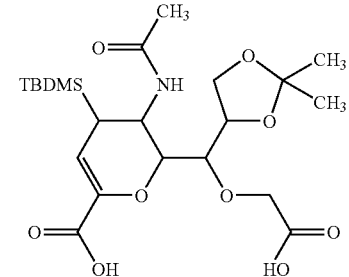

Sodium hydroxide (5 mL, 0.1 M, 0.5 mmol) was added slowly to a stirred solution of 28 (100 mg, 0.19 mmol) in THF (5 mL). The resulting mixture was stirred for 2 h at room temperature. The organic solvent was evaporated and the aqueous solution was acidified with HCl to pH=2, extracted with ethyl acetate, and extract was concentrated to give 29 as a white solid (66 mg, 70%). mp 130° C. $[\alpha]_D^{26}$+35.1° (c 1.2, CH₃OH). ¹H NMR (CD₃OD, 500 MHz) 60.11 (s, 3H, CH₃), 0.14 (s, 3H, CH₃), 0.91 (s, 9H, 3CH₃), 1.32 (s, 3H, CH₃), 1.39 (s, 3H, CH₃), 2.0 (s, 3H, NAc), 3.66 (s, 2H, OCH₂), 3.98 (m, 2H), 4.14 (t, J=8.0 Hz, 1H), 4.20 (t, J=8.0 Hz, 1H), 4.27 (m, 1H, H-6), 4.33 (m, 1H), 4.63 (m, 1H, H-4), 5.84 (s, 1H, H-3). ¹³C NMR (CD₃OD, 125 MHz) δ -4.65, -4.45, 18.81, 23.19, 25.43, 26.18, 26.61, 30.89, 51.97, 66.47, 68.13, 68.79, 70.76, 77.71, 78.38, 78.68, 109.35, 113.37, 144.93, 164.97, 173.24, 173.61. ESIMS calcd for $C_{22}H_{37}NO_{10}SiNa$ $[M+Na]^+$ 526.3. Found 526.3. Anal. Calc. for $C_{22}H_{37}NO_{10}Si$: C, 52.47; H, 7.41; N, 2.78. Found: C, 52.38; H, 7.48; N, 2.64.

5-Acetylamino-4-[2,3-bis(tert-butoxycarbonyl)guanidine]-6-(1,2,3-triacetoxy-propyl)-5,6-dihydro-4H-pyran-2-carboxylic acid methyl ester (31)

Lindlar catalyst (1 g) was added to a stirred solution of 30 (5.0 g, 11.0 mmol) in anhydrous ethanol (80 mL) and the flask was flashed with argon. Hydrogen gas was then bubbled through the vigorously stirred solution for 10 h. The reaction mixture was then filtered through celite, and the filtrate was concentrated. The residue was dissolved in dry THF (50 mL). N,N'-bis(tert-butoxycarbonyl)-1H-pyrazole-1-carboxamidine (3.42 g, 11.0 mmol) and triethylamine (1.9 mL, 13.2 mmol) were then added. The mixture was stirred vigorously overnight at room temperature. The reaction mixture was then concentrated and purified by column chromatography (hexane/ethyl acetate=1:1) to give 31 as a colorless oil (6.1 g, 82%). TLC (hexane/ethyl acetate, 1:1): $R_f$=0.20. $^1$H NMR ($CDCl_3$, 500 MHz) δ 1.50 (s, 18H, 6$CH_3$), 1.86 (s, 3H, NAc), 2.04, 2.06, 2.08 (3s, 12H, 3OAc), 3.79 (s, 3H, $OCH_3$), 4.28 (m, 1H), 4.70 (dd, J=2.0 Hz, 10.5 Hz, 1H) 5.13 (m, 1H), 5.30 (m, 1H), 5.51 (d, J=4.0 Hz, 1H), 5.86 (d, J=1.5 Hz, 1H, H-3), 6.37 (s, 1H, NH), 7.15 (d, J=9.0 Hz, 1H), 7.69 (s, 1H), 8.51 (d, J=9.0 Hz, 1H, NH), 11.42 (s, 1H, NH). $^{13}$C NMR ($CDCl_3$, 125 MHz) δ 20.80, 20.86, 20.94, 21.04, 23.00, 28.06, 28.31, 47.60, 49.19, 52.45, 60.40, 62.38, 67.89, 71.69, 77.96, 79.90, 83.90, 105.12, 109.79, 145.21, 152.69, 157.33, 161.75, 162.96, 170.22, 170.32, 170.58, 170.87. FABHRMS calcd for $C_{29}H_{44}N_4O_{14}Na$ $[M+Na]^+$ 695.2751. Found 695.2750.

5-Acetylamino-4-[2,3-bis(tert-butoxycarbonyl)guanidine]-6-[(2,2-dimethyl-[1,3]dioxolan-4-yl)-hydroxy-methyl]-5,6-dihydro-4H-pyran-2-carboxylic acid methyl ester (32)

NaOMe (2 mL, 0.5 M, 1 mmol) was added to a stirred solution of 31 (3.0 g, 4.46 mmol) in anhydrous methanol (60 mL). The reaction mixture was then stirred for 30 min, Dowex 50WX8 acidic resin was added to neutralize the reaction mixture and filtered. The filtrate was concentrated and dissolved in dry acetone (50 mL). 2,2-Dimethoxypropane (4.5 mL, 36.7 mmol) and p-toluenesulfonic acid (80 mg, 0.4 mmol) were added to the reaction mixture. The resulting mixture was stirred overnight at room temperature. The reaction mixture was then concentrated and purified by column chromatography (hexane/ethyl acetate=1:1) to give 32 as a white solid (2.3 g, 88%). TLC (hexane/ethyl acetate, 1:3): $R_f$=0.47. mp 126° C. $^1$H NMR ($CDCl_3$, 500 MHz) δ 1.37 (s, 3H, $CH_3$), 1.43 (s, 3H, $CH_3$), 1.50 (s, 9H, 3$CH_3$), 1.52 (s, 9H, 3$CH_3$), 2.02 (s, 3H, NAc), 3.50 (m, 1H, H-7), 3.79 (s, 3H, $OCH_3$), 3.97 (m, 1H, H-5), 4.03 (m, 1H, H-6), 4.10 (m, 1H, H-9), 4.10 (m, 1H, H-9'), 4.40 (m, 1H, H-8), 5.15 (m, 1H, H-4), 5.28 (d, J=4.0 Hz, 1H, OH), 5.80 (d, J=2.0 Hz, 1H, H-3), 8.00 (d, J=5.5 Hz, 1H, NH), 8.64 (d, J=7.5 Hz, 1H, NH), 11.37 (s, 1H, NH). $^{13}$C NMR ($CDCl_3$, 125 MHz) δ 22.98, 25.25, 27.12, 28.04, 28.24, 48.46 (C-4), 52.13 ($OCH_3$), 52.41 (C-5), 67.50 (C-9), 69.75 (C-7), 74.01 (C-8), 78.53, 80.09 (C-6), 84.38, 106.67 (C-3), 109.19, 146.96 (C-2), 152.70, 157.66, 161.99, 162.35, 174.01. FABHRMS calcd for $C_{26}H_{43}N_4O_{11}$, $[M+H]^+$ 587.2928. Found 587.2951. Anal. Calc. for $C_{26}H_{42}N_4O_{11}$: C, 53.23; H, 7.22; N, 9.55. Found: C, 53.20; H, 7.26; N, 9.51.

5-Acetylamino-4-[2,3-bis(tert-butoxycarbonyl)guanidine]-6-[(2,2-dimethyl-[1,3]dioxolan-4-yl)-(4-nitro-phenoxycarbonyloxy)-methyl]-5,6-dihydro-4H-pyran-2-carboxylic acid methyl ester (33)

To a solution of 32 (286 mg, 0.49 mmol) in dry pyridine (10 mL) was added 4-dimethylaminopyridine (149 mg, 1.22 mmol) and 4-nitrophenylchloroformate (245 mg, 1.22 mmol). The reaction mixture was stirred vigorously overnight at room temperature. The solution was then concentrated and the residue was extracted with ethyl acetate and purified by column chromatography (hexane/ethyl acetate=1:1) to give 33 as a white solid (271 mg, 74%). TLC (hexane/ethyl acetate, 1:3): $R_f$=0.69. mp 150° C. $^1$H NMR ($CDCl_3$, 500 MHz) δ 1.39 (s, 3H, $CH_3$), 1.42 (s, 3H, $CH_3$), 1.49 (s, 18H, 6$CH_3$), 1.94 (s, 3H, NAc), 3.82 (s, 3H, $OCH_3$), 4.14 (m, 1H, H-9), 4.23 (m, 2H, H-8, H-9'), 4.41 (m, 1H, H-5), 4.45 (m, 1H, H-6), 5.19 (t, J=9.5 Hz, 1H, H-4), 5.24 (d, J=5.0 Hz, 1H, H-7), 5.90 (d, J=2.5 Hz, 1H, H-3), 6.46 (broad s, 1H, NH), 7.53 (dd, J=1.5 Hz, 9.0 Hz, 2H, Ar), 8.26 (dd, J=1.5 Hz, 9.0 Hz, 2H, Ar), 8.58 (d, J=8.5 Hz, 1H, NH), 11.35 (s, 1H, NH). $^{13}$C NMR ($CDCl_3$, 125 MHz) δ 23.30, 25.64, 26.63, 28.20, 28.41, 48.74 (C-4), 48.89 (C-5), 52.76 ($OCH_3$), 65.89 (C-9), 74.33 (C-7), 75.10 (C-6), 77.70 (C-8), 80.18, 84.37, 109.18 (C-2), 115.81, 122.47, 125.39, 126.39, 145.63 (C-2), 152.66, 152.86, 155.98, 157.50, 161.74, 162.88, 171.85. FABHRMS calcd for $C_{33}H_{45}N_5O_{15}Na$ $[M+Na]^+$ 774.2810. Found 774.2848. Anal. Calc. for $C_{33}H_{45}N_5O_{15}$: C, 52.73; H, 6.03; N, 9.32. Found: C, 52.66; H, 6.06; N, 9.15.

Conjugation of 29 to Resin to Give 34 and 35

PL-PEGA resin (120 mg, 0.4 mmol/g, 150-300 μm) was swelled in DMF overnight, Fmoc-Gly-OH/Boc-Gly-OH (480 μL, 0.3 M, 9:1 mol/mol), HOBt (144 μL, 1.0 M) and DIC (22 μL) were then added to the resin. The resin was shaken for 2 h, and washed with DMF (5×3 mL), MeOH (5×3 mL), $CH_2Cl_2$ (5×3 mL), DMF (5×3 mL). Orthogonally protected PL-PEGA resin (40 mg) was treated with 20% piperidine in DMF for 30 min, then washed with DMF (5×3 mL), MeOH (5×3 mL), $CH_2Cl_2$ (5×3 mL), DMF (5×3 mL). Compound 29 (25 mg, 48 μmol), HOBt (48 μL, 1.0 M) and DIC (8 μL) were added to the resin. The resin was shaken for 3 h, and washed with DMF (5×3 mL), MeOH (5×3 mL), $CH_2Cl_2$ (5×3 mL), DMF (5×3 mL). The resin was treated with TBAF (1.0 mL, 0.1 M) and shaken overnight. After washing the resin as described before, 1 mL 50% TFA in DCM was added and shaken for 30 min. After washing as described before, 20 mg resin was coupled with substrate 14 (2 mg) using HOBt (5 μL, 1.0 M) and DIC (1 μL) to give 34. Another 20 mg resin was coupled with substrate 24 (2 mg) using HOBt (5 μL, 1.0 M) and DIC (1 μL) to give 35.

Conjugation of 33 to Resin to Give 36 and 37

Orthogonally protected PL-PEGA (40 mg) resin was treated with 20% piperidine in DMF for 30 min, then washed with DMF (5×3 mL), MeOH (5×3 mL), $CH_2Cl_2$ (5×3 mL), DMF (5×3 mL). Compound 33 (36 mg, 48 μmol), DMAP (12 mg, 96 μmol) and pyridine (1 mL) were added to the resin. The resin was shaken for 40 h, and washed with DMF (5×3 mL), MeOH (5×3 mL), $CH_2Cl_2$ (5×3 mL), DMF (5×3 mL). The resin was treated with aq. NaOH (1.0 mL, 0.1 M) and shaken for 2 h. After washing the resin as described before, 1 mL 50% TFA in DCM was added and shaken for 30 min. After washing as described before, 20 mg resin was coupled with substrate 14 (2 mg) using HOBt (5 μL, 1.0 M) and DIC (1 μL), and optionally $Bu_3N$ (5 μL) to give 36. Another 20 mg resin was coupled with substrate 24 (2 mg) using HOBt (5 μL, 1.0 M) and DIC (1 μL), and optionally $Bu_3N$ (5 μL) to give 37.

Preparation of Acetylated Blank Resin 38 and 39

Orthogonally protected PL-PEGA resin (40 mg) was treated with 20% piperidine in DMF for 30 min, then washed with DMF (5×3 mL), MeOH (5×3 mL), $CH_2Cl_2$ (5×3 mL), DMF (5×3 mL). $Ac_2O$ (0.5 mL) and pyridine (0.5 mL) were added to the resin. The resin was shaken overnight, and washed with DMF (5×3 mL), MeOH (5×3 mL), $CH_2Cl_2$ (5×3 mL), DMF (5×3 mL). Resin (20 mg) was coupled with substrate 14 (2 mg) using HOBt (5 μL, 1.0 M) and DIC (1 μL) to give 38. Another 20 mg resin was coupled with substrate 24 (2 mg) using HOBt (5 μL, 1.0 M) and DIC (1 μL) to give 39.

Example 7

Figure 12:
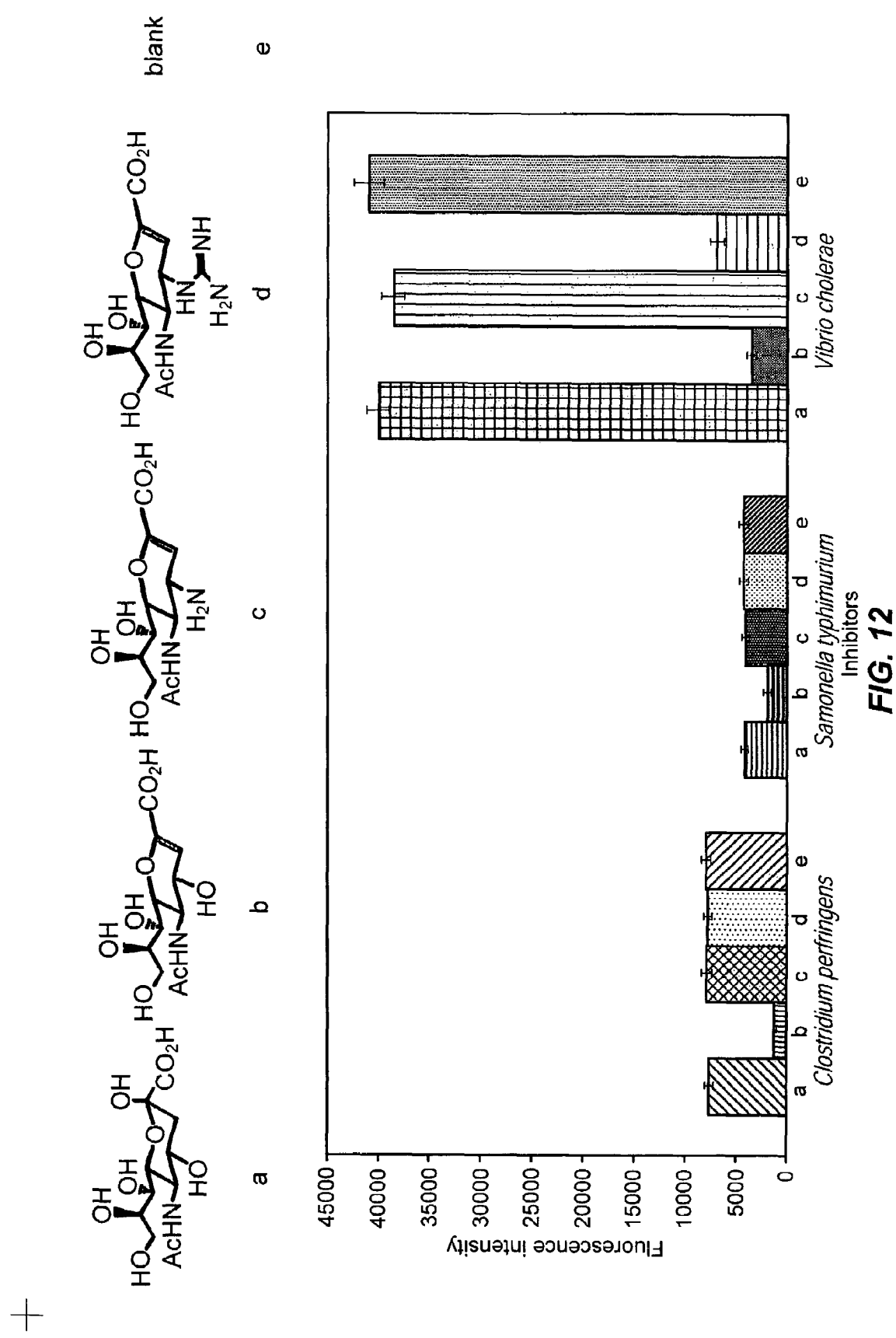
FIG. 12 illustrates the results of a fluorescence assay of on-bead substrate 15 and 25 with inhibitors in solution. Inhibition of the cleavage of fluorogenic conjugates 15 and 25 using inhibitors a-d.
Figure 13:
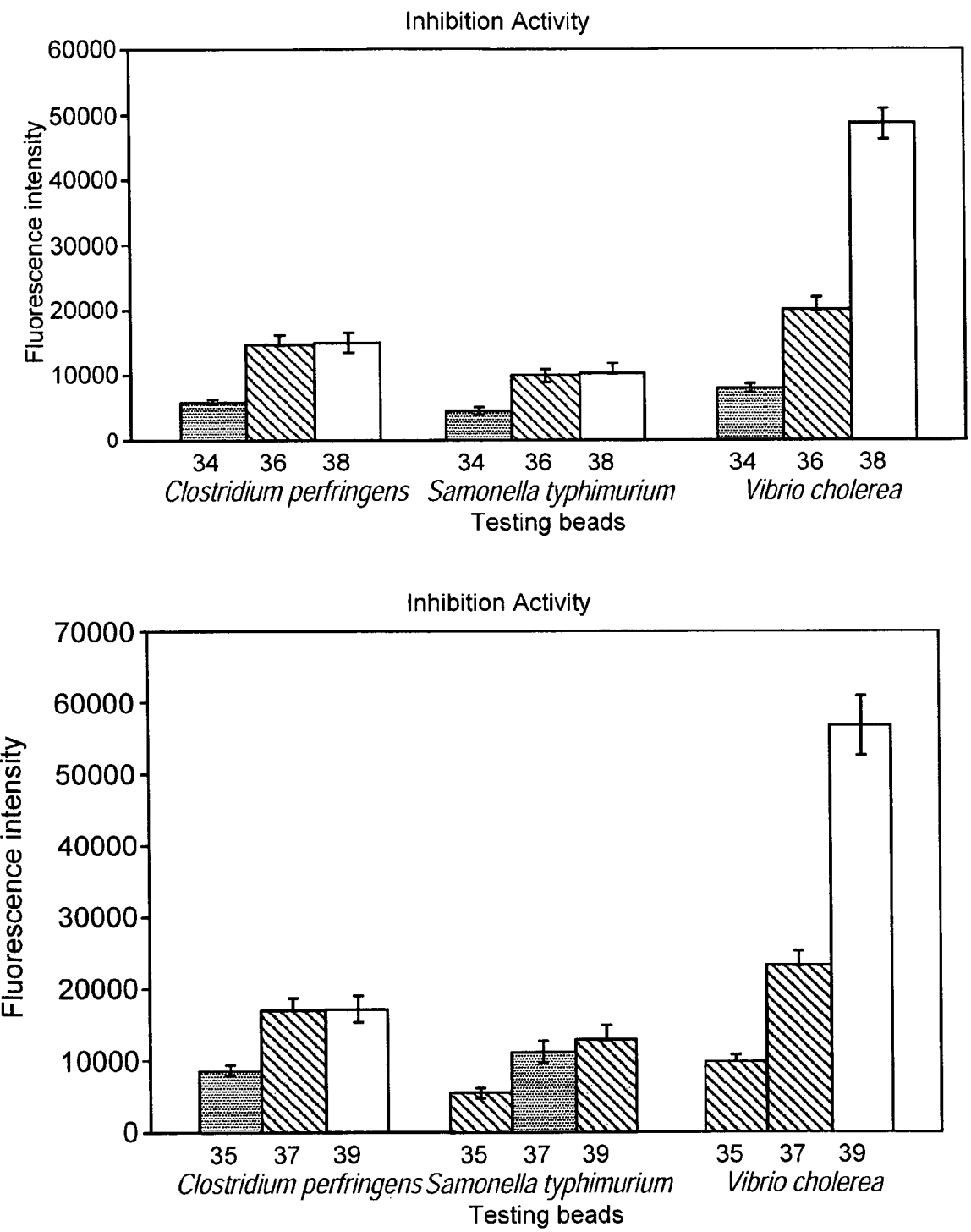
FIG. 13 illustrates the results of an on-bead assay of bacterial neuraminidase. Fluorescence intensities of beads 35-39 incubated with three different neuraminidases.

Screening Test Ligands for Inhibition of Neuraminidase Using Solution Phase Fluorogenic Substrate Assay To test the activity of fluorogenic substrates 15 and 25 in solution, four known inhibitors a-d (0.5 mM) were preincubated with three different neuraminidases (*Clostridium perfringens*, *Salmonella typhimurium*, and *Vibrio cholerae*, 5 mU, SIGMA) in 32.5 mM 2-(N-morpholino)-ethanesulfonic acid (MES) buffer (4 mM $CaCl_2$, pH 6.5) at room temperature for 30 min individually. The substrates 15 and 25 (10 μL) were then added to the solution of each well. The fluorescence intensity was measured after 20 min. incubation using a Perkin-Elmer fluorescence plate reader with an excitation wavelength of 355 nm, emission wavelength of 460 nm for substrate 15 and an excitation wavelength of 485 nm, emission wavelength of 535 nm for substrate 25. As shown in FIG. 12, both substrate 15 and 25 had good activity for bacterial neuraminidases. These results show that the substrates 15 and 25 could be recognized by neuraminidases while still attached to beads. As shown in the $IC_{50}$ results in Table 1,2-deoxy-2,3-dehydro-N-acetylneuraminic acid, DANA, (b) was found to be a good inhibitor for the three bacterial neuraminidases, and 4-guanidino-Neu5Ac2en, ZANAMIVIR™ (d) is an inhibitor for *Vibro cholerae* neuraminidase.

TABLE 1

Solution phase $IC_{50}$ values

| Compound | *Clostridium perfringens* | *Salmonella typhimurium* | *Vibrio cholerae* |
|---|---|---|---|
| Sialic Acid (a) | >2 mM | >2 mM | >2 mM |
| DANA (b) | 4 uM | 0.31 mM (0.35 mM)$^{lit}$ | 20 uM (30 uM)$^{lit}$ |
| 4-Amino DANA (c) | >2 mM | >2 mM | >2 mM |
| Zanamivir (d) | >2 nM | >2 mM | 0.2 mM |

TABLE 1-continued
Solution phase IC$_{50}$ values
| Compound | Clostridium perfringens | Salmonella typhimurium | Vibrio cholerae |
|---|---|---|---|
| 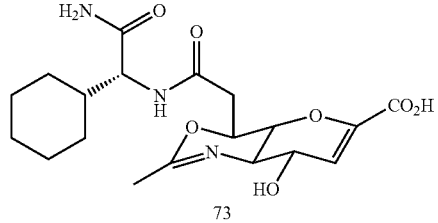 73 | 1.6 mM | >2 mM | >2 mM |
| 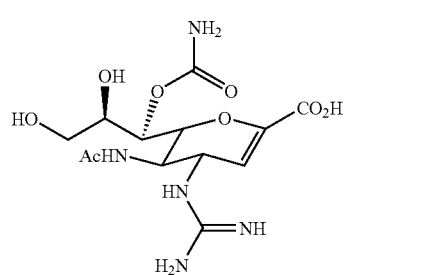 7-Carbamide analog of Zanamivir | >

135.92, 136.50, 151.05, 151.10, 154.94, 160.21, 161.11, 167.63, 172.65. FABHRMS calcd for $C_{20}H_{18}N_3O_8$ $[M+H]^+$ 428.1094. Found 428.1102.

N-[1-Carbamoyl-2-(4-hydroxy-3-nitro-phenyl)-ethyl]-N'-[2-(2-{2-[2-(7-hydroxy-2-oxo-2H-chromen-4-yl)-acetylamino]-ethoxy}-ethoxy)-ethyl]-succinamide (42)

Compound 42 was prepared using rink amide MBHA resin (140 mg, 0.6 mmol/g) as solid support according to standard peptide synthesis (HOBt 3 eq, DIC 3 eq) and isolated by precipitation with diethyl ether to give a yellow solid (42 mg, 75%). mp 115° C. $^1$H NMR (DMSO, 500 MHz) δ 2.24 (m, 4H, 2CH$_2$), 2.85 (m, 2H, CH$_2$), 3.16 (t, J=6.0 Hz, 2H, CH$_2$), 3.22 (t, J=6.0 Hz, 2H, CH$_2$), 3.37 (t, J=6.0 Hz, 2H, CH$_2$), 3.41 (t, J=6.0 Hz, 2H, CH$_2$), 3.50 (m, 4H, 2CH$_2$), 3.65 (s, 2H, CH$_2$), 4.34 (m, 1H), 5.73 (s, 1H), 6.16 (s, 1H), 6.72 (d, J=2.0 Hz, 1H), 6.79 (dd, J=2.0 Hz, 9.0 Hz, 1H), 7.03 (d, J=8.5 Hz, 1H), 7.41 (d, J=8.5 Hz, 1H), 7.60 (d, J=8.5 Hz, 1H), 7.77 (s, 1H). $^{13}$C NMR (DMSO, 125 MHz) δ 30.56, 30.69, 36.10, 38.55, 38.83, 38.89, 53.66, 66.48, 69.01, 69.14, 69.64, 102.35, 111.65, 111.81, 112.94, 118.85, 125.43, 126.84, 129.73, 136.55, 151.42, 155.10, 160.45, 161.09, 167.94, 171.94, 171.58, 171.78, 173.01. FABHRMS calcd for $C_{30}H_{36}N_5O_{12}$ $[M+H]^+$ 658.2360. Found 658.2381.

Methyl (benzyl 5-(7-acetoxy-4-coumarinyl-acetamido)-4,7,8,9-tetra-O-acetyl-3,5-dideoxy-D-glycero-α-D-galacto-2-nonulopyranosid)onate (46)

Phosphorus pentachloride (1.08 g, 5.2 mmol) was added to a solution of 44 (see Ikeda, K. et al. *Chem. Pharm. Bull.* 1991, 39, 1305-1309), (1.51 g, 2.6 mmol) and N,N-dimethylaniline (1.33 mL, 10.4 mmol) in dry DCM (20 mL) at −35° C., and the mixture was stirred for 7 h. Then, MeOH (8 mL) was added to the solution and the mixture was stirred for another 2.5 h at the same temperature. Water (5 mL) was added and the mixture was warmed to room temperature and stirred overnight. The resulting solution was washed with aqueous saturated NaHCO$_3$ and brine. The organic phase was dried over anhydrous Na$_2$SO$_4$ and evaporated to dryness in vacuo. The residue was redissolved in dry THF (15 mL), 45 (see Gerber, S. A. et al. *Bioconjugate Chem.* 2001, 12, 603-615; and Nordlander, J. E. et al. *J. Org. Chem.* 1984, 49, 4107-4111), (2.6 mmol in 5 mL DCM) and DIEA (1.36 mL, 7.8 mmol) were added to the mixture and stirred overnight. The resulting mixture was washed with saturated NaHCO$_3$ and brine. The organic phase was dried over anhydrous Na$_2$SO$_4$ and evaporated to dryness. The residue was purified by column chromatography (hexane/ethyl acetate=1:2) to give 46 as a white solid (0.61 g, 30%). TLC (hexane/ethyl acetate, 1:3): $R_f$=0.36. mp 88° C. $[α]_D^{26}$+39.1° (c 0.5, CHCl$_3$). $^1$H NMR (CHCl$_3$, 500 MHz) δ 1.75-2.33 (m, 16H, 5OAc, H-3a), 2.65 (dd, J=4.5 Hz, 13.0 Hz, 1H, H$_{3e}$), 3.59 (s, 3H, OCH$_3$), 3.61(m, 2H, CH$_2$), 4.16 (m, 3H), 4.32 (m, 1H), 4.41 (d, J=12.0 Hz, 1H), 4.82 (m, 2H), 5.32 (m, 1H), 5.46 (m, 1H), 6.23 (d, J=10.0 Hz, 1H, NH), 6.36 (s, 1H), 7.11 (m, 2H), 7.25 (m, 1H), 7.31 (m, 4H), 7.76 (d, J=8.5 Hz, 1H). $^{13}$C NMR (CHCl$_3$, 125 MHz) δ 20.67, 20.94, 20.99, 21.23, 21.26, 38.23, 40.67, 49.73, 52.75, 62.59, 66.96, 67.57, 68.73, 69.09, 72.27, 98.64, 110.70, 116.45, 116.93, 118.65, 126.56, 127.85, 127.94, 128.37, 137.22, 148.86, 153.57, 154.48, 160.61, 167.70, 168.37, 168.70, 170.26, 170.47, 170.77, 170.82. FABHRMS calcd for $C_{38}H_{41}NO_{17}Na$ $[M+Na]^+$ 806.2267. Found 806.2271. Anal. Calc. for $C_{38}H_{41}NO_{17}$: C, 58.24; H, 5.27; N, 1.79. Found: C, 58.12; H, 5.34; N, 1.76.

Methyl 5-(7-acetoxy-3,4-dihydro-4-coumarinyl-acetamido)-4,7,8,9-tetra-O-acetyl-3,5-dideoxy-D-glycero-β-D-galacto-2-nonulopyranosionate (47)

To a solution of 46 (200 mg, 0.25 mmol) in methanol (20 mL) was added palladium on charcoal (30 mg, 10% Pd). The mixture was stirred overnight under hydrogen at normal pressure. The catalyst was filtered off and washed with methanol. The filtrate was concentrated and the residue was purified by column chromatography (hexane/ethyl acetate=1:3) to give 47 as a white solid (138 mg, 78%). TLC (hexane/ethyl acetate, 1:3): $R_f$=0.25. mp 97° C. $[α]_D^{26}$−5.0° (c 0.5, CHCl$_3$). $^1$H NMR (CHCl$_3$, 500 MHz) δ 2.02-2.29 (m, 19H, 5OAc, H-3a, H-3e, CH$_2$), 2.81 (m, 2H, CH$_2$), 3.70 (s, 3H, OCH$_3$), 4.03 (dd, J=8.0 Hz, 12.5 Hz, 1H, H-9a), 4.20 (m, 2H, H-5, H-9b), 4.53 (m, 1H, H-6), 5.15 (m, 1H), 5.22 (m, 1H), 5.34 (m, 1H), 6.15 (m, 1H), 6.83 (m, 2H), 7.29 (m, 1H). $^{13}$C NMR (CHCl$_3$, 125 MHz) δ 21.06, 21.24, 21.29, 31.08, 31.29, 34.02, 34.26, 36.26, 26.40, 41.00, 41.06, 49.27, 49.60, 67.33, 68.37, 69.54, 71.12, 71.29, 71.56, 71.74, 95.10, 111.17, 118.01, 118.20, 123.20, 123.78, 128.39, 128.69, 150.72, 152.05, 167.34, 169.22, 169.42, 169.47, 170.05, 170.27, 170.54, 170.63, 171.19, 171.25, 171.29, 171.34. FABHRMS calcd for $C_{31}H_{37}NO_{17}Na$ $[M+Na]^+$ 718.1954. Found 718.1934. Anal. Calc. for $C_{31}H_{37}NO_{17}$: C, 53.53; H, 5.36; N, 2.01. Found: C, 53.42; H, 5.39; N, 2.04.

Methyl (benzyl 5-(9H-fluoren-9-ylmethoxycarbonylamino)-4,7,8,9-tetra-O-acetyl-3,5-dideoxy-D-glycero-β-D-galacto-2-nonulopyranosid)onate (48)

Phosphorus pentachloride (500 mg, 2.6 mmol) was added to a solution of 44 (see Ikeda, K. et al. *Chem. Pharm. Bull.* 1991, 39, 1305-1309), (754 mg, 1.3 mmol) and N,N-dimethylaniline (660 μL, 5.2 mmol) in dry DCM (15 mL) at −35° C., and the mixture was stirred for 7 h. Then, MeOH (4 mL) was added to the solution and the mixture was stirred for another 2.5 h at the same temperature. Water (2.5 mL) was added and the mixture was warmed to room temperature and stirred overnight. The resulting mixture was washed with aqueous saturated NaHCO$_3$ and brine. The organic phase was dried over anhydrous Na$_2$SO$_4$ and evaporated to dryness in vacuo. The residue was redissolved in dry THF (10 mL), Fmoc-Cl (336 mg, 1.3 mmol) and DIEA (680 μL, 3.9 mmol) were added to the mixture and stirred overnight. The resulting mixture was washed with saturated NaHCO$_3$ and brine. The organic phase was dried over anhydrous Na$_2$SO$_4$ and evaporated to dryness. The residue was purified by column chromatography (hexane/ethyl acetate=1:1) to give 48 as a white solid (0.49 g, 52%). TLC (hexane/ethyl acetate, 1:3): $R_f$=0.75. mp 92° C. $[α]_D^{26}$+3.1° (c 0.5, CHCl$_3$). $^1$H NMR (CHCl$_3$, 500 MHz) δ 1.94-2.17 (m, 13H, 4OAc, H-3a), 2.71 (dd, J=4.0 Hz, 12.5 Hz, 1H, H$_{3e}$), 3.70 (s, 3H, OCH$_3$), 3.79 (m, 1H, H-5), 4.18 (m, 4H), 4.33 (m, 2H), 4.44 (d, J=12.0 Hz, 1H), 4.63 (d, J=10.0 Hz, 1H, NH), 4.83 (d, J=12.0 Hz, 1H), 4.93 (m, 1H, H-4), 5.48 (s, 2H, OCH$_2$), 7.33 (m, 7H), 7.39 (t, J=7.5 Hz, 2H), 7.58 (m, 2H), 7.75 (d, J=7.5 Hz, 2H). $^{13}$C NMR (CHCl$_3$, 125 MHz) δ 21.03, 21.09, 21.42, 38.56, 47.28, 51.78, 52.91, 62.58, 67.15, 67.35, 67.63, 67.72, 68.65, 69.20, 72.81, 98.76, 120.20, 120.24, 125.25, 125.55, 127.32, 127.90, 127.97, 128.11, 128.50, 141.48, 141.59, 143.79, 156.08, 168.60, 170.32, 170.95. FABHRMS calcd for $C_{40}H_{43}NO_{14}Na$ $[M+Na]^+$ 784.2576. Found 784.2616. Anal. Calc. for $C_{40}H_{43}NO_{14}$: C, 63.07; H, 5.69; N, 1.84. Found: C, 63.02; H, 5.78; N, 1.82.

Methyl (4-methoxybenzyl 5-(7-acetoxy-4-coumarinylacetamido)-4,7,8,9-tetra-O-acetyl-3,5-dideoxy-D-glycero-α-D-galacto-2-nonulopyranosid)onate (50)

Phosphorus pentachloride (70 mg, 0.34 nmol) was added to a solution of 49 (see Ikeda, K. et al. *Bioorg. Med. Chem. Lett.* 2002, 12, 2309-2311), (103 mg, 0.17 mmol) and N,N-dimethylaniline (86 µL, 0.67 mmol) in dry DCM (5 mL) at −35° C., and the mixture was stirred for 7 h. Then, MeOH (2 mL) was added to the solution and the mixture was stirred for another 2.5 h at the same temperature. Water (1 mL) was added and the mixture was warmed to room temperature and stirred overnight. The resulting mixture was washed with aqueous saturated NaHCO$_3$ and brine. The organic phase was dried over anhydrate Na$_2$SO$_4$ and evaporated to dryness in vacuo. The residue was redissolved in dry THF (5 mL), 45 (see Gerber, S. A. et al. *Bioconjugate Chem.* 2001, 12, 603-615); and Nordlander, J. E. et al. *J. Org. Chem.* 1984, 49, 4107-4111), (0.17 mmol in 1 mL DCM) and DIEA (68 µL, 0.39 mmol) were added to the mixture and stirred for overnight. The resulting mixture was washed with saturated NaHCO$_3$ and brine. The organic phase was dried over anhydrous Na$_2$SO$_4$ and evaporated to dryness. The residue was purified by column chromatography (hexane/ethyl acetate=1:3) to give 50 as a white solid (38 mg, 28%). TLC (hexane/ethyl acetate, 1:3): R$_f$=0.29. [α]$_D^{26}$+16.1° (c 0.4, CHCl$_3$). $^1$H NMR (CHCl$_3$, 500 MHz) δ 1.70-2.33 (m, 16H, 5OAc, H-3a), 2.61 (dd, J=4.5 Hz, 13.0 Hz, 1H, H$_{3e}$), 3.53 (m, 2H, CH$_2$) 3.68 (s, 3H, OCH$_3$), 3.79 (s, 3H, OCH$_3$), 4.02 (m, 1H), 4.14 (m, 1H), 4.33 (d, J=11.5 Hz, 1H), 4.73 (d, J=11.5 Hz, 1H), 4.82 (m, 1H), 5.29 (m, 1H), 5.46 (m, 2H), 6.34 (s, 1H), 6.85 (d, J=8.5 Hz, 2H), 7.10 (dd, J=2.5 Hz, 9.0 Hz, 1H), 7.14 (d, J=2.5 Hz, 1H), 7.24 (d, J=8.5 Hz, 2H), 7.69 (d, J=9.0 Hz, 1H). $^{13}$C NMR (CHCl$_3$, 125 MHz) δ 20.80, 21.04, 21.12, 21.35, 21.41, 32.19, 40.67, 50.38, 52.98, 55.54, 62.60, 66.96, 67.66, 68.77, 68.89, 7.46, 98.73, 110.89, 113.96, 116.74, 116.95, 118.70, 126.45, 129.82, 148.36, 153.55, 154.75, 160.20, 167.66, 168.53, 168.77, 170.37, 170.67, 170.89, 171.08. ESIMS calcd for C$_{39}$H$_{43}$NO$_{18}$Na [M+Na]$^+$ 836.2, found 836.2. Anal. Calc. for C$_{39}$H$_{43}$NO$_{18}$: C, 57.56; H, 5.33; N, 1.72. Found: C, 57.50; H, 5.48; N, 1.74.

Methyl 5-(7-acetoxy-4-coumarinyl-acetamido)-4,7,8,9-tetra-O-acetyl-3,5-dideoxy-D-glycero-α-D-galacto-2-nonulopyranosonate (51)

To a solution of 50 (20 mg, 0.025 mmol) in CH$_2$Cl$_2$ (3 mL) and H$_2$O (167 µL) was added DDQ (8.4 mg, 0.037 mmol). The mixture was stirred for 40 h at room temperature. The mixture was washed with saturated NaHCO$_3$, brine, dried with anhydrous Na$_2$SO$_4$, and concentrated. The residue was purified by column chromatography (hexane/ethyl acetate=1:3) to give 51 as a white solid (13.6 mg, 80%). TLC (hexane/ethyl acetate, 1:3): R$_f$=0.20. mp 105° C. [α]$_D^{26}$+7.6° (c 0.5, CHCl$_3$). $^1$H NMR (CHCl$_3$, 500 MHz) δ 1.78-2.33 (m, 17H, 5OAc, H-3a, H-3e), 3.63 (m, 2H, CH$_2$), 3.85 (s, 3H, OCH$_3$), 4.02 (m, 1H), 4.20 (m, 1H), 4.47 (m, 2H), 5.19 (m, 2H), 5.30 (m, 1H), 6.09 (d, J=10.0 Hz, 1H, NH), 6.38 (s, 1H), 7.09 (dd, J=2.5 Hz, 9.0 Hz, 1H), 7.14 (d, J=2.5 Hz, 1H), 7.73 (d, J=9.0 Hz, 1H). $^{13}$C NMR (CHCl$_3$, 125 MHz) δ 20.86, 21.05, 21.23, 21.36, 36.32, 40.55, 50.21, 53.77, 62.87, 68.16, 69.27, 70.87, 71.39, 95.06, 110.80, 116.61, 117.11, 118.61, 126.54, 148.73, 153.63, 154.72, 160.55, 167.80, 168.80, 169.18, 170.63, 171.08, 171.14, 171.23. ESIMS calcd for C$_{31}$H$_{35}$NO$_{17}$Na [M+Na]$^+$ 716.2. Found 716.4. Anal. Calc. for C$_{31}$H$_{35}$NO$_{17}$: C, 53.68; H, 5.09; N, 2.02. Found: C, 53.52; H, 5.16; N, 2.04.

CMP-5-(7-hydroxy-4-coumarinyl-acetamido)-NeuAc (55)

To a solution of 7-hydroxy-4-coumarinylacetic acid N-succinimidyl ester (see Demant, E. J. F. *Biochimica et Biophysica Acta* 1996, 1304, 43-55), (0.5 mg, 1.6 µmol) in DMSO (0.3 mL) was added a solution of 58. Dufner, G. et al. *Eur. J. Org. Chem.* 2000, 1467-1482. (1 mg, 1.6 µmol) in H$_2$O (0.2 mL). Then, a solution of saturated NaHCO$_3$ was added to control the pH 8.59.0. The mixture was stirred for 1 h at room temperature. The mixture was purified by RP-HPLC (H$_2$O/CH$_3$OH=90:10~70:30) to give 55 as a white powder (0.4 mg, 32%). $^1$H NMR (D$_2$O, 500 MHz) δ 1.66 (m, 1H, H-3a), 2.50 (dd, J=4.5 Hz, 13.0 Hz, 1H, H-3e), 3.41 (d, J=10.0 Hz, 1H), 3.54 (dd, J=7.0 Hz, 12.0 Hz, 1H), 3.77 (s, 1H), 3.83 (dd, J=2.0 Hz, 11.5 Hz, 1H), 3.93 (m, 5H), 4.08 (m, 1H), 4.19 (d, J=10.5 Hz, 1H), 4.25 (m, 3H), 4.31 (t, J=4.5 Hz, 1H), 4.35 (m, 1H), 5.99 (d, J=4.5 Hz, 1H), 6.10 (d, J=7.5 Hz, 1H), 6.24 (s, 1H), 6.75 (d, J=2.0 Hz, 1H), 6.84 (dd, J=2.0 Hz, 9.0 Hz, 1H), 7.57 (d, J=9.0 Hz, 1H), 7.97 (d, J=7.5 Hz, 1H). $^{13}$C NMR (D$_2$O, 125 MHz) δ 38.97, 41.25, 43.07, 52.17, 63.21, 65.01, 66.81, 66.91, 69.07, 69.50, 69.89, 71.87, 74.53, 83.09, 89.34, 96.80, 100.28, 103.84, 110.71, 115.77, 126.46, 141.79, 152.13, 155.66, 158.00, 165.10, 166.39, 171.98, 172.37, 174.51. ESIMS calcd for C$_{31}$H$_{38}$N$_5$O$_{20}$P [M−H]$^-$ 830.2. Found 830.2.

Example 10

Synthesis of Detectable Label-Donor Substrate Conjugate CMP-5-fluoresceinylaminoacetyl-Neu (59)

To a solution of fluoresceinyl isothiocyanate (12 mg, 30.8 µmol) in DMF (1 mL) was added a solution of 58 (see Dufner, G. et al. *Eur. J. Org. Chem.* 2000, 1467-1482), (10 mg, 16 µmol) in H$_2$O (1 mL). Then, a solution of saturated NaHCO$_3$ was added to control the pH 8.5~9.0. The mixture was stirred for 30 min at room temperature. The mixture was purified by RP-HPLC (H$_2$O/CH$_3$OH=90:10~60:40) to give 59 as brown powder (15 mg, 92%). [α]$_D^{26}$+8.1° (c 1.0, H$_2$O) $^1$HNMR (D$_2$O, 500 MHz) δ 1.63 (m, 1H, H-3a), 2.47 (dd, J=4.5 Hz, 13.0 Hz, 1H, H-3e), 2.81 (s, 1H), 2.97 (s, 1H), 3.59 (m, 1H), 3.70 (m, 1H), 3.90 (m, 2H), 4.01 (t, J=10.0 Hz, 1H), 4.13 (m, 1H), 4.18 (m, 7H), 5.93 (d, J=4.5 Hz, 1H), 6.05 (d, J=7.5 Hz, 1H), 6.54 (m, 3H), 7.16 (m, 3H), 7.55 (d, J=8.0 Hz, 1H), 7.72 (s, 1H), 7.89 (m, 1H). $^{13}$C NMR (D$_2$O, 125 MHz) δ 37.10, 41.23, 47.81, 52.15, 63.46, 64.98, 66.92, 69.14, 69.52, 70.13, 71.88, 74.41, 83.06, 89.35, 96.78, 100.32, 103.84, 112.57, 123.06, 124.78, 126.00, 129.77, 131.44, 131.62, 141.19, 141.74, 157.94, 158.41, 158.86, 160.84, 165.12, 166.31, 172.62, 174.37, 174.58, 180.70. ESIMS calcd for C$_{41}$H$_{43}$N$_6$O$_{21}$PS [M−H]$^-$ 1017.2. Found 1017.1.

Example 11

Synthesis of Detectable Label-Donor Substrate Conjugate CMP-5-(7-amino-4-methylcoumarinyl-acetamido)-NeuAc (60)

To a solution of 7-amino-4-methyl-3-coumarinylacetic acid N-succinimidyl ester (see Stefanova, H. I. et al. *Biochem.* 1993, 32, 356-62), (0.53 mg, 1.6 µmol) in DMSO (0.3 mL) was added a solution of 58 (see Dufner, G. et al. *Eur. J. Org. Chem.* 2000, 1467-1482), (1 mg, 1.6 µmol) in H$_2$O (0.2 mL). Then, a solution of saturated NaHCO$_3$ was added to control the pH 8.5~9.0. The mixture was stirred for 1 h at room temperature. The mixture was purified by RP-HPLC (H₂O/CH₃OH=90:10~70:30) to give 60 as a white powder (0.5 mg, 36%). $^1$H NMR (D₂O, 500 MHz) δ 1.67 (m, 1H, H-3a), 2.43 (s, 3H, CH₃), 2.51 (dd, J=4.5 Hz, 13.0 Hz, 1H, H-3e), 3.42 (d, J=10.0 Hz, 1H), 3.58-3.77 (m, 3H), 3.87 (m, 1H), 3.93-4.02 (m, 5H), 4.20-4.32 (m, 6H), 4.39 (t, J=5.0 Hz, 1H), 5.96 (d, J=4.5 Hz, 1H), 6.01 (d, J=7.5 Hz, 1H), 6.69 (s, 1H), 6.82 (d, J=8.5 Hz, 1H), 7.62 (m, 1H), 7.89 (d, J=7.5 Hz, 1H). $^{13}$C NMR (D₂O, 125 MHz) δ 15.00, 34.15, 43.04, 52.18, 63.27, 65.01, 66.78, 69.13, 69.64, 69.96, 71.90, 74.54, 83.12, 89.24, 96.66, 100.31, 112.02, 113.47, 113.67, 127.13, 141.63, 151.58, 153.98, 166.23, 172.29, 174.50. ESIMS calcd for C₃₂H₄₁N₆O₁₉P [M–H]⁻ 843.2. Found 843.4.

Example 12

Synthesis of Quencher-Acceptor Substrate Conjugate 2-(3-Nitro-L-tyrosyl-amide)ethyl β-D-galactopyranysl-(1→4)-O-β-D-glucopyranoside (64)

To a solution of 63 (see Hatanaka, Y. et al. *Bioorg. Med. Chem. Lett.* 1995, 5, 2859-2862), (24 mg, 35 μmol) in THF (5 mL) was added N$^α$-Fmoc-Tyr(3-NO₂)-OPfp (44 mg, 71 μmol) and DIEA (12 μL, 71 μmol). The mixture was stirred for overnight at room temperature. The mixture was concentrated and the residue was purified by column chromatography (ethyl acetate). The purified compound was dissolved in 20% piperidine in DMF (2 mL), and stirred for 30 min. The mixture was concentrated and the residue was redissolved in dry methanol (2 mL). NaOMe (0.2 mL, 0.5 M) was added to the solution. The mixture was stirred for 1 h, then neutralized with Dowex 50WX8 (H+) resin, filtered, washed with methanol, and evaporated. The residue was purified by RP-HPLC (H₂O/CH₃OH=90:10~80:20) to give 64 as a yellow solid (4.2 mg, 20%). $^1$H NMR (D₂O, 500 MHz) δ 3.17-3.28 (m, 4H), 3.37-3.39 (m, 2H), 3.55 (m, 2H), 3.61-3.81 (m, 8H), 3.93 (m, 2H), 4.17 (m, 1H), 4.42 (m, 2H), 7.20 (d, J=8.5 Hz, 1H), 7.55 (d, J=8.5 Hz, 1H), 8.02 (s, 1H). $^{13}$C NMR (D₂O, 125 MHz) δ 39.52, 42.75, 54.32, 54.56, 60.24, 61.24, 68.20, 68.73, 71.14, 72.72, 74.53, 74.95, 75.58, 78.57, 102.27, 103.15, 120.57, 126.18, 126.53, 134.32, 138.64, 153.12, 168.82. ESIMS calcd for C₂₃H₃₆N₃O₁₅ [M+H]⁺ 594.2. Found 594.1.

Example 13

Synthesis of Quencher-Acceptor Substrate Conjugate 2-(3-Nitro-L-tyrosyl-amide)ethyl β-D-galactopyranysl-(1→4)-O-2-acetamido-2-deoxy-β-D-glucopyranoside (68)

To a solution of 67 (see Mohan, H. et al. *Synlett* 2003, 9, 1255-1256), (6 mg, 8.5 μmol) in methanol (2 mL) was added palladium on charcoal (5 mg, 10% Pd). The mixture was stirred 4 h under hydrogen at normal pressure. The catalyst was filtered off and washed with methanol. The filtrate was concentrated and redissolved in THF (1 mL), N$^α$-Fmoc-Tyr(3-NO₂)-OPfP (8 mg, 12.9 μmol) and DIEA (3 μL, 18 μmol) was added. The mixture was stirred overnight at room temperature. The mixture was concentrated and the residue was purified by column chromatography (ethyl acetate, R$_f$=0.12). The purified compound was dissolved in 20% piperidine in DMF (1 mL), and stirred for 30 min. The mixture was concentrated and the residue was redissolved in dry methanol (1 mL). NaOMe (0.1 mL, 0.5 M) was added to the solution. The mixture was stirred for 1 h, then neutralized with Dowex 50WX8 (H+) resin, filtered, washed with methanol, and evaporated. The residue was purified by RP-HPLC (H₂O/CH₃OH=90:10~80:20) to give 68 as a yellow solid (0.76 mg, 14%). $^1$H NMR (D₂O, 500 MHz) δ 1.99 (s, 3H, NAc), 3.15 (m, 2H), 3.23 (m, 2H), 3.41 (m, 1H), 3.55 (m, 1H), 3.60 (m, 1H), 3.64-3.77 (m, 8H), 3.82 (dd, J=5.0 Hz, 12.5 Hz, 1H), 3.93 (m, 2H), 4.15 (t, J=8.0 Hz, 1H), 4.46 (d, J=7.5 Hz, 2H), 7.20 (d, J=8.5 Hz, 1H), 7.53 (dd, J=2.0 Hz, 8.5 Hz, 1H), 8.02 (d, J=2.0 Hz, 1H). $^{13}$C NMR (D₂O, 125 MHz) δ 39.62, 44.75, 54.27, 55.13, 60.24, 61.25, 67.97, 68.75, 71.16, 72.65, 72.72, 74.93, 75.60, 78.63, 101.45, 103.11, 120.66, 126.19, 126.45, 138.65, 153.17, 168.76, 174.84. ESIMS calcd for C₂₅H₃₉N₄O₁₅ [M+H]⁺ 635.23. Found 635.15.

Example 14

Synthesis of Quencher-Acceptor Substrate Conjugate 4-Aminophenyl 2,3,4,6-tetra-O-acetyl-β-D-galactopyransyl-(1→3)-O-2-acetamido-2-deoxy-β-D-glucopyranoside (73)

To a solution of 72 (see Matta, K. L. and Barlow, J. J. *Carbohydr. Res.* 1975, 43, 299-304), (46 mg, 60.5 μmol) in methanol (5 mL) was added palladium on charcoal (10 mg, 10% Pd). The mixture was stirred overnight under hydrogen at normal pressure. The catalyst was filtered off and washed with methanol. The filtrate was concentrated and the residue was purified by column chromatography (ethyl acetate/methanol=6:1) to give 73 as a white solid (16.3 mg, 42%). TLC (methanol/ethyl acetate, 1:6): R$_f$=0.20. mp 136° C. [α]$_D^{26}$+12.9° (c 0.7, CH₃OH). $^1$H NMR (CD₃OD, 500 MHz) δ 1.85, 1.92, 1.94, 1.99, 2.06 (5s, 1SH, 4OAc, 1NAc), 3.09 (m, 1H), 3.32 (m, 1H), 3.39 (t, J=9.5 Hz, 1H), 3.64 (m, 1H), 3.81 (m, 1H), 4.08 (m, 3H), 4.68 (d, J=7.0 Hz, 1H), 4.75 (d, J=7.0 Hz, 1H), 5.05 (m, 2H), 5.30 (m, 1H), 6.57 (d, J=8.5 Hz, 1H), 6.73 (d, J=8.5 Hz, 1H). $^{13}$C NMR (CD₃OD, 125 MHz) δ 20.48, 20.56, 20.88, 23.26, 47.88, 56.21, 62.55, 68.75, 70.01, 70.22, 72.14, 72.40, 77.78, 84.60, 102.29, 102.41, 117.67, 119.16, 143.88, 152.23, 171.42, 171.45, 171.89, 172.09, 173.41. ESIMS calcd for C₂₈H₃₉N₂O₁₅ [M+H]⁺ 643.2. Found 643.1.

Example 15

Testing Acceptors 64 and 68 for Substrate Recognition by Sialyltransferases

Figure 15:
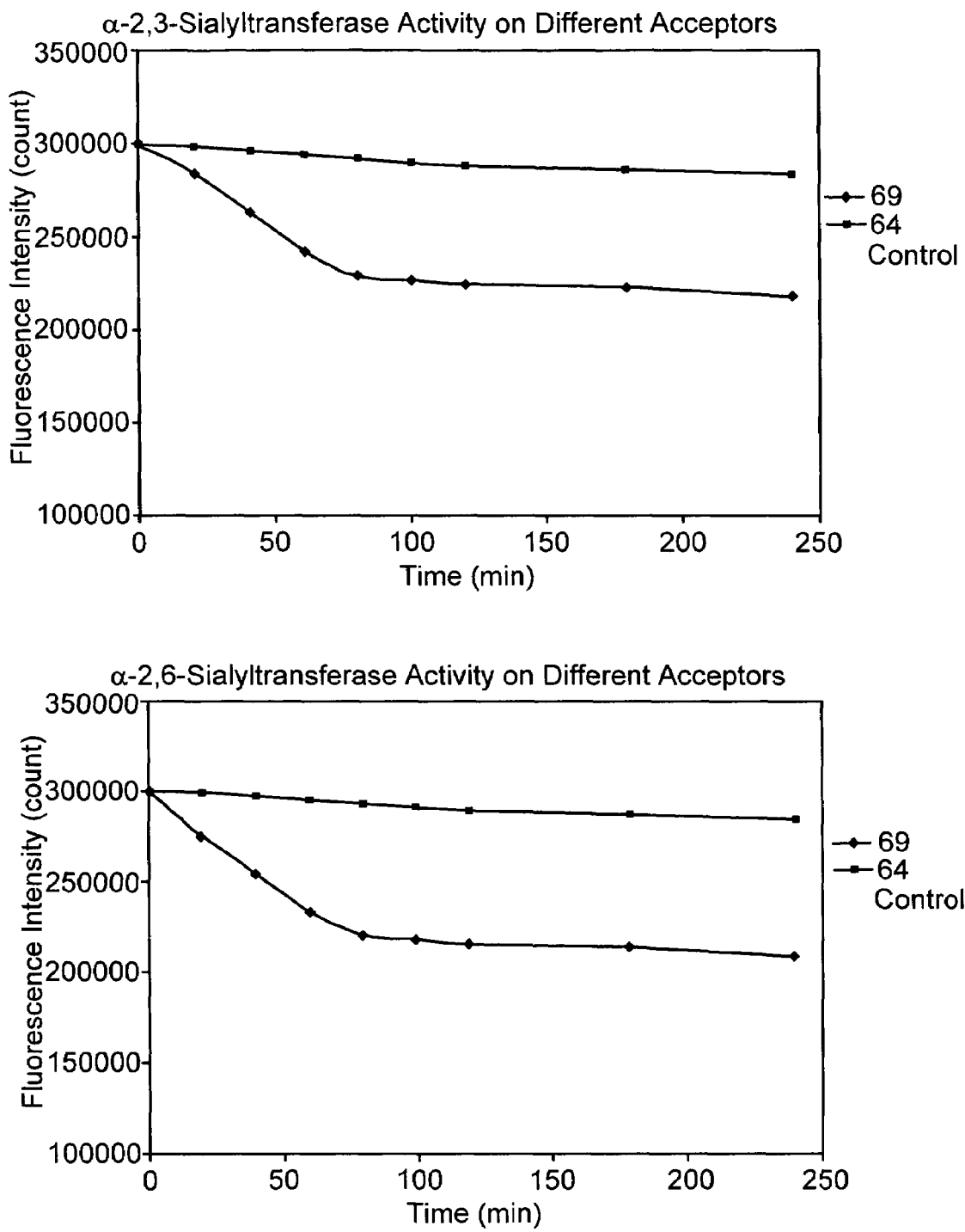
FIG. 15 illustrates the activity of acceptors 64 and 69 for substrate recognition by sialyltransferase.

To test the activity and quenching efficiency of acceptors with fluorescent donors, the acceptors 64 and 69 were chosen to incubate with the fluorescent donor 55 in the presence of sialyltransferase. As a control, the fluorescent donor 55 was also incubated in two blank wells plated with 100 μL sodium cacodylate buffer (pH 6.0) and sialyltransferase in the absence of acceptor. The enzymatic reaction was carried out in a buffer containing 62.5 mM sodium cacodylate (pH=6.0), 1 mg/mL BSA, and 0.5% Triton X 100 (see Gross, H. J. et al. *Anal. Biochem.* 1990, 186, 127-134). The plate was immediately incubated at 37° C. and 1000 rpm in a Jitterburg™ microplate incubator (Boekel). The fluorescence intensity of each well was measured using a PerkinElmer fluorescence plate reader every 20 min in the first 2 h and every 60 min in the next 2 h at an excitation wavelength of 355 nm, emission wavelength of 460 nm. As shown in FIG. 15, under normal incubation conditions (acceptor 0.2 mM, donor 0.1 mM, sialyltransferase 0.2 mU), acceptor 69 and donor 55 are good substrates for both α2,3-sialyltransferase and α2,6-sialyltransferase. Acceptor 64 showed poor substrate recognition by both enzymes. This is consistent results with literature report (see Limberg, G. et al. *Liebigs Ann.* 1996, 1773-1784).

In the first 20% consumption of donor 55, the change of fluorescence intensity gave very good linear response with incubation time on both enzymes. These assays showed that the fluorescent donor 55 and the quenching acceptor 69 are good FRET pair for sialyltransferase assay.

Example 16

Sialyltransferase Competitive Assay

Figure 16:
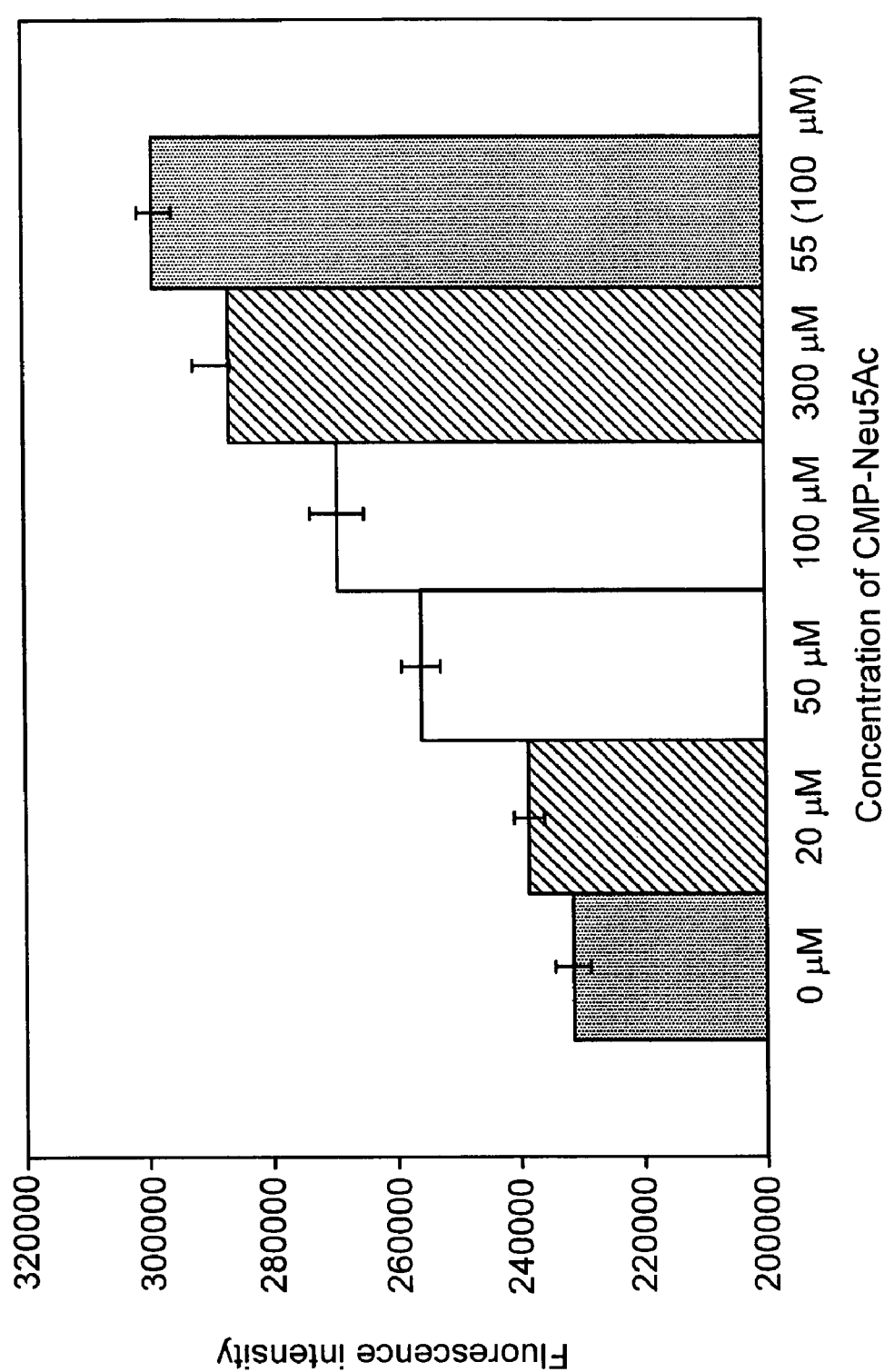
FIG. 16 illustrates the results of a sialyltransferase competitive assay using donor 55 and CMP-Neu5Ac
Figure 17:
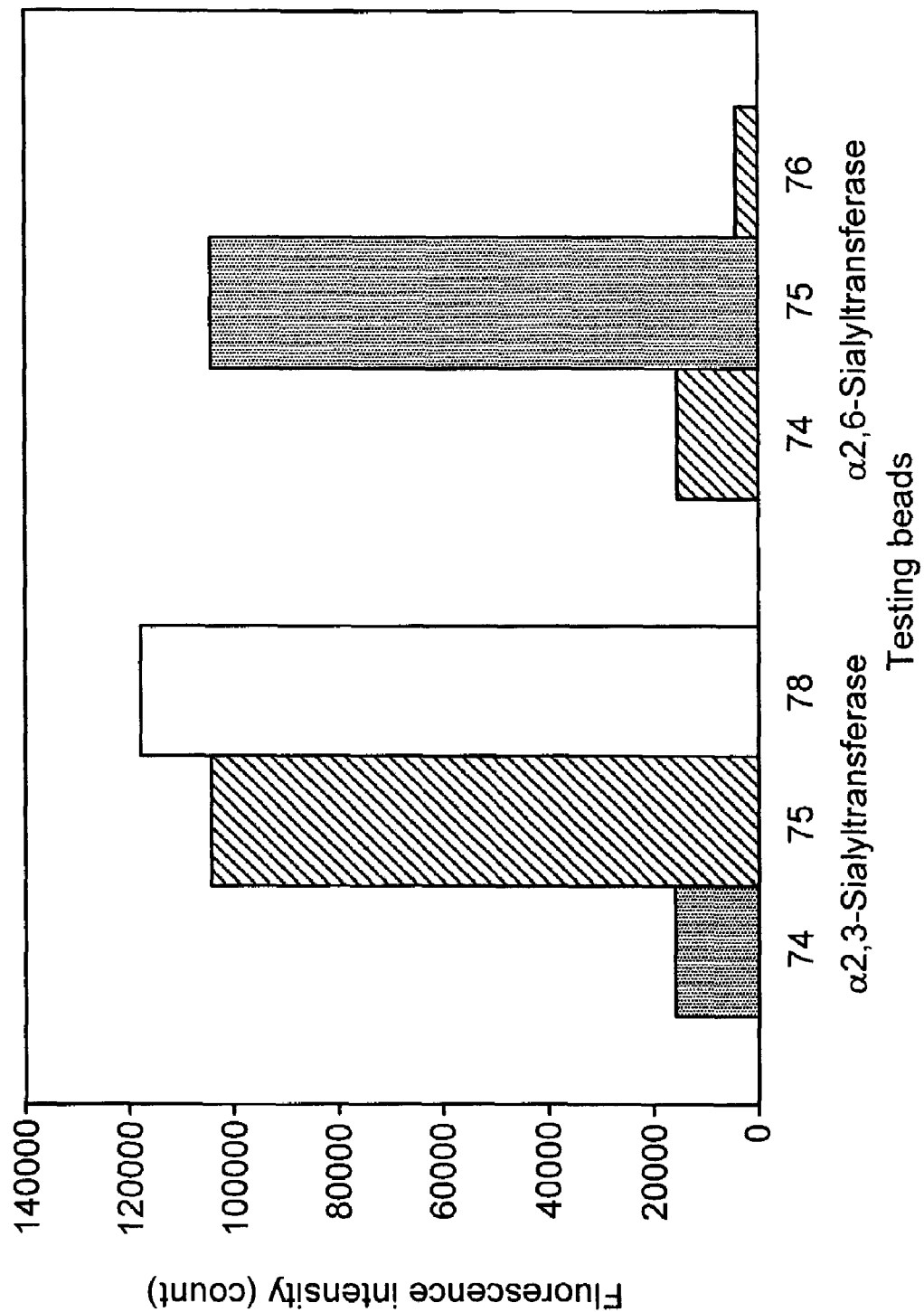
FIG. 17 illustrates the recognition of on-bead acceptors by sialyltransferases.

To test the inhibitory activity of potential inhibitors of sialyltransferases, CMP-Neu5Ac was used as a model testing compound. Various concentrations of CMP-Neu5Ac (0 μM, 20 μM, 50 μM, 100 μM, 300 μM) were first incubated with α2,6-sialyltransferase (0.2 mU) in sodium cacodylate buffer (pH=6.0) for 30 min. Then, the fluorescent donor 55 (0.1 mM) and quenching acceptor 69 (0.2 mM) were added and the reaction mixtures were incubated at 37° C. and 1000 rpm in a Jitterburg™ microplate incubator (Boekel) for 1 h. As a blank control, α2,6-sialyltransferase (0.2 mU) was also incubated with the fluorescent donor 55 (0.1 mM) and quenching acceptor 69 (0.2 mM) without CMP-Neu5Ac for 1 h. The fluorescence intensity of each well was measured using a PerkinElmer fluorescence plate reader at an excitation wavelength of 355 nm, emission wavelength of 460 nm. As shown in FIG. 16, fluorescence intensities showed continual increase with increase of CMP-Neu5Ac concentrations and FIG. 17 illustrates the recognition of on-bead acceptors by sialyltransferases. If one considers the blank as 100% no inhibition, the $IC_{50}$ of CMP-Neu5Ac for α2,6-sialyltransferase is 85 μM, which is consistent with a KM value of 45 μM (see Gross, H. J. et al. *Biochem.* 1989, 28, 7386-7392). Using this competitive assay, one can simply test the inhibitory activity of sialyltransferase inhibitors.

Example 17

Synthesis of On-Bead Acceptors 74, 75, and 76.

PL-PEGA resin (60 mg, 0.4 mmol/g, 150-300 μm) was swelled in DMF overnight. The resin was coupled with Fmoc-Phe(4-$NO_2$)—OH (3 eq) using HOBt (3 eq) and DIC (3 eq) for 3 h. After rinsing resin with DMF (5×3 mL), MeOH (5×3 mL), $CH_2Cl_2$ (5×3 mL), DMF (5×3 mL), the Fmoc protecting group was cleaved by incubation with 20% piperidine in DMF for 30 min. After rinsing resin as described before, the resin was distributed into two portions (20 mg and 40 mg). One portion (40 mg) of the resin was coupled with a mixture of Fmoc/Ac-Gly-OH (1:10, 3 eq) using HOBt (3 eq) and DIC (3 eq) for 3 h. After rinsing resin as described before, the Fmoc protecting group was cleaved with 20% piperidine in DMF for 30 min, the resin was then reacted with succinic anhydride (10 eq) in the presence of DIEA (10 eq) in DMF for 3 h. After rinsing resin as described before, the resin was equally distributed to two portions. One portion was coupled with acceptor 64 (3 eq) using HOBt (3 eq) and DIC (3 eq) for 3 h, followed by removal of acetate group using NaOMe (0.1 mL, 0.5 M) in MeOH (1 mL) for 1 h to give 74. Another portion was activated to acid chloride using oxalyl chloride (0.2 mL) in DCM (1 mL) for 2 h, then reacted with acceptor 73 (3 eq) in the presence of DIEA (10 eq) in DMF for 4 h to give 76. The other portion (20 mg) of resin was coupled with a mixture of 4-pentynoic acid/Ac-Gly-OH (1:10, 3 eq) using HOBt (3 eq) and DIC (3 eq) in DMF for 3 h. After rinsing resin as described before, the resin was reacted with acceptor 68 (2 eq) in the presence $CuSO_4$ (1 eq) and sodium ascorbate (1 eq) in $^tBuOH$ (0.4 mL) and $H_2O$ (0.4 mL) overnight to afford 75.

Example 18

Testing of On-Bead Acceptors 74, 75 and 76 for Substrate Recognition by sialyltransferases The beads 76, 77 and 78 (20 μL) were each plated into two wells containing 100 μL sodium cacodylate buffer (pH 6.0). Fluorescent donor 59 (10 μL, 1 mM) was added to each well, followed by addition of sialyltransferase (0.1 mU). The plate was immediately incubated at 37° C. and 1000 rpm in a Jitterburg™ microplate incubator (Boekel) for 6 h. The beads in each well were rinsed with water (200×5 μL) to remove the remaining fluorescent donor 59. After washing, sodium cacodylate buffer (100 μL) was added to each well. The fluorescence intensity of each well was measured using a PerkinElmer fluorescence plate reader at an excitation wavelength of 485 nm, emission wavelength of 535 nm.

Example 19

Synthesis of Test Ligands 77 and 78

PL-PEGA resin (40 mg, 0.4 mmol/g, 150-300 μm) was swelled in DMF overnight. The resin was coupled with Fmoc-Phe(4-$NO_2$)—OH (3 eq) using HOBt (3 eq) and DIC (3 eq) for 3 h. After rinsing resin with DMF (5×3 mL), MeOH (5×3 mL), $CH_2Cl_2$ (5×3 mL), DMF (5×3 mL), the Fmoc protecting group was cleaved by incubation with 20% piperidine in DMF for 30 min. After rinsing resin as described before, the resin was coupled with a mixture of 4-pentynoic acid/Fmoc-Trp-OH (1:10, 3 eq) using HOBt (3 eq) and DIC (3 eq) in DMF for 3 h. After rinsing resin as described before, the resin was equally distributed to two portions. One portion was constructed with peptide WWWWNG-$NH_2$, another portion was constructed with peptide WWWWWG-$NH_2$ using standard peptide synthesis. Then, the resin was reacted with acceptor 68 (2 eq) in the presence $CuSO_4$ (1 eq) and sodium ascorbate (1 eq) in $^tBuOH$ (0.4 mL) and $H_2O$ (0.4 mL) overnight to give 77 and 78, respectively.

Example 20

Screening Test Ligands for Inhibition of Sialyltransferase Using Solid Phase Fluorogenic Substrate Assay.

Figure 18:
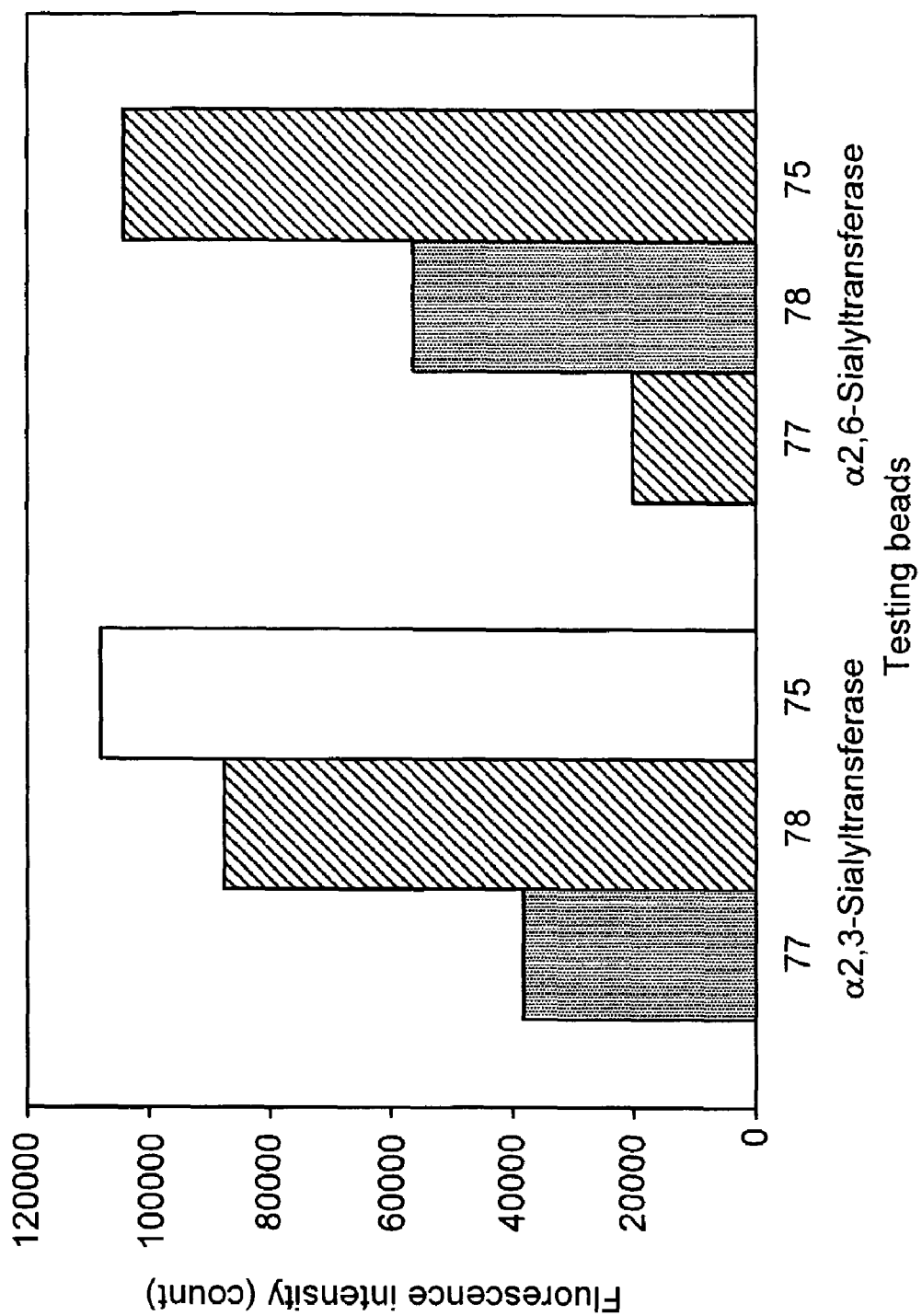
FIG. 18 illustrates the inhibitory activity of 75, 77 and 78 against sialyltransferases.

The beads 77, 78 and 75 (20 μL) were plated into two wells containing 100 μL sodium cacodylate buffer (pH 6.0). Fluorescent donor 59 (10 μL, 1 mM) and sialyltransferase (0.1 mU) were added to each well. The plate was immediately incubated at 37° C. and 1000 rpm in a Jitterburg™ microplate incubator (Boekel) for 6 h. The beads in each well were rinsed with water (200×5 μL) to remove the remaining fluorescent donor 59. After washing, sodium cacodylate buffer (100 mL) was added to each well. The fluorescence intensity of each well was measured using a PerkinElmer fluorescence plate reader at an excitation wavelength of 485 nm, emission wavelength of 535 nm. FIG. 18 illustrates the inhibitory activity of 75, 77 and 78 against sialyltransferases.

The neuraminidase inhibitors identified using the methods of the present invention will be especially effective in treating influenza. Examples of neuraminidase inhibitors which are employed in compositions known in the art to treat influenza include, but are not limited to, ZANAMIVIR™ (2,4-dideoxy-2,3-didehydro-4-guanidino-sialic acid) and OSELTAMIVIR™ (ethyl 4-acetamido-5-amino-3-(1-ethylpropxy)-1- cyclohexene-1-carboxylate) and known, biologically active derivatives of any of the above.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An assay complex comprising at least one test ligand and at least one composition comprising a solid support and a conjugate comprising a detectable label covalently attached to the substrate of a neuraminidase wherein modification of said substrate causes a detectable change in said label, wherein the test ligand is attached by covalent interaction with said solid support.

2. The complex of claim 1, wherein said detectable label is selected from the group consisting of a fluorogenic label and a chromogenic label.

3. The complex of claim 2, wherein said fluorogenic label is selected from the group consisting of 2'-(4-methylumbelliferyl)-α-D-acetyl-neuraminic acid and fluoroscein.

4. The complex of claim 1, wherein the substrate is sialic acid.

5. The complex of claim 1 wherein the conjugate has the formula selected from the group consisting of compounds 10, 15 and 25.

6. The complex of claim 1, wherein said at least one test ligand is a library of test ligands.

7. The complex of claim 1, wherein said substrate is sialic acid.

8. The complex of claim 1, wherein the conjugate is attached by covalent interaction with the solid support.

9. The complex of claim 1, wherein the conjugate is attached by noncovalent interaction with the solid support.

10. The complex of claim 1, wherein the solid support is selected from the group consisting of a bead, a slide and a chip.

11. The complex of claim 1, wherein the solid support is a bead.

12. The complex of claim 7 wherein the conjugate has the formula selected from the group consisting of compounds 10, 15 and 25.

13. An assay complex comprising at least one test ligand attached to a solid support and at least one detectable label-substrate conjugate comprising a detectable label covalently attached to a first substrate of an enzyme and a quencher attached to a second substrate of said enzyme wherein modification of said substrates causes a detectable change in said label and either said detectable label covalently attached to a first substrate of said enzyme or said quencher attached to a second substrate of an enzyme is attached to said solid support.

14. The complex of claim 13, wherein said at least one test ligand is a library of test ligands.

15. The complex of claim 13 wherein the detectable label covalently attached to a first substrate of an enzyme has the formula selected from the group consisting of compounds 55, 59 and 60.

16. The complex of claim 13 wherein the quencher attached to a second substrate of an enzyme having the formula selected from the group consisting of compounds 64, 69, and 73.

17. The complex of claim 13, wherein the conjugate is attached by covalent interaction with the solid support.

18. The complex of claim 13, wherein the conjugate is attached by noncovalent interaction with the solid support.

19. The complex of claim 13, wherein the solid support is selected from the group consisting of a bead, a slide and a chip.

20. The complex of claim 13, wherein the solid support is a bead.

21. A method of identifying an enzyme inhibitor comprising:
    a) combining in an assay mixture the complex of claim 1 and a sufficient quantity of said enzyme to react with the substrate under noninhibitory conditions; and
    b) detecting a change in said label in said assay mixture upon combination with said enzyme; wherein the presence of an enzyme inhibitor prevents said enzyme from modifying said substrate and causing a change in said detectable label; and
    c) identifying the test ligand which prevents said detectable change.

22. The method of claim 21, wherein the enzyme is neuraminidase or sialyltransferase and the natural substrate is sialic acid.

23. The method of claim 21, wherein said change is a fluorescent emission.

24. The method of claim 23, wherein the detecting step is performed by monitoring the change in fluorescence emission of fluoroscein attached to sialic acid.

25. The method of claim 23, wherein the detecting step is performed by monitoring the change in fluorescence emission of 2'-(4-methylumberllifreyl)-α-D-acetyl-neuraminic acid attached to sialic acid.

* * * * *